(12) United States Patent  (10) Patent No.: US 7,809,428 B2
Elmaleh et al.  (45) Date of Patent: Oct. 5, 2010

(54) DEVICES FOR DETECTION AND THERAPY OF ATHEROMATOUS PLAQUE

(75) Inventors: David Elmaleh, Boston, MA (US); Farhad Daghighian, Los Angeles, CA (US)

(73) Assignees: The General Hospital Corporation, Boston, MA (US); IntraMedical Imaging LLC, Los Angeles, CA (US)

( * ) Notice: Subject to any disclaimer, the term of this patent is extended or adjusted under 35 U.S.C. 154(b) by 371 days.

(21) Appl. No.: 10/215,600

(22) Filed: Aug. 9, 2002

(65) Prior Publication Data

US 2003/0055307 A1 Mar. 20, 2003

Related U.S. Application Data

(60) Division of application No. 10/215,958, filed on Aug. 9, 2002, now abandoned, which is a continuation-in-part of application No. 10/163,744, filed on Jun. 4, 2002, now abandoned.

(60) Provisional application No. 60/295,627, filed on Jun. 4, 2001, provisional application No. 60/365,673, filed on Mar. 15, 2002.

(51) Int. Cl.
*A61B 6/00* (2006.01)
*A61F 2/06* (2006.01)

(52) U.S. Cl. ............... 600/436; 600/431; 623/1.42; 623/1.11

(58) Field of Classification Search ............ 600/407, 600/433–435, 473–481, 431, 436; 601/1–4; 623/1.11, 1.13, 1.12, 1.42–1.46
See application file for complete search history.

(56) References Cited

U.S. PATENT DOCUMENTS

| 4,141,347 | A |   | 2/1979 | Green et al. |
| 4,512,762 | A | * | 4/1985 | Spears ................... 604/21 |
| 4,577,636 | A | * | 3/1986 | Spears ................. 424/1.53 |
| 4,995,396 | A |   | 2/1991 | Inaba et al. |
| 5,008,546 | A |   | 4/1991 | Mazziotta et al. |
| 5,046,501 | A |   | 9/1991 | Crilly |
| 5,104,392 | A |   | 4/1992 | Kittrell et al. |

(Continued)

FOREIGN PATENT DOCUMENTS

EP 0352076 A2 1/1990

(Continued)

OTHER PUBLICATIONS

Akhlynina, T., et al., "Insulin-mediated Intracellular Targeting Enhances the Photodynamic Activity of Chlorin $e_6$," *Cancer Research*, 55: 1014-1019, 1995.

(Continued)

*Primary Examiner*—Long V Le
*Assistant Examiner*—Jacqueline Cheng
(74) *Attorney, Agent, or Firm*—Edwards Angell Palmer & dodge LLP; Peter C. Lauro, Esq.; Brian R. Landry, Esq.

(57) ABSTRACT

The present invention relates to devices for detection of active atheromatous plaque and/or thin-capped fibro-atheroma ("vulnerable plaque") using selectively targeted radiolabeled compositions, such as beta-emitting compositions.

26 Claims, 26 Drawing Sheets

U.S. PATENT DOCUMENTS

| | | | |
|---|---|---|---|
| 5,116,864 A | 5/1992 | March et al. | |
| 5,169,395 A | 12/1992 | Narciso, Jr. | |
| 5,197,470 A | 3/1993 | Helfer et al. | |
| 5,298,018 A | 3/1994 | Narciso, Jr. | |
| 5,308,861 A | 5/1994 | Aizawa et al. | |
| 5,364,612 A | 11/1994 | Goldenberg | |
| 5,409,710 A | 4/1995 | Leonard | |
| 5,419,323 A | 5/1995 | Kittrell et al. | |
| 5,422,362 A | 6/1995 | Vincent et al. | |
| 5,424,073 A | 6/1995 | Rahman et al. | |
| 5,484,803 A | 1/1996 | Richter | |
| 5,568,532 A | 10/1996 | Majewski et al. | |
| 5,639,600 A | 6/1997 | McGrath et al. | |
| 5,693,043 A | 12/1997 | Kittrell et al. | |
| 5,716,595 A * | 2/1998 | Goldenberg | 424/1.49 |
| 5,736,563 A | 4/1998 | Richter | |
| 5,744,805 A | 4/1998 | Raylman et al. | |
| 5,773,417 A | 6/1998 | Bonaventura | |
| 5,776,966 A | 7/1998 | North | |
| 5,789,433 A | 8/1998 | Chan et al. | |
| 5,798,349 A | 8/1998 | Levy et al. | |
| 5,807,881 A | 9/1998 | Leong et al. | |
| 5,811,814 A | 9/1998 | Leone et al. | |
| 5,829,448 A | 11/1998 | Fisher et al. | |
| 5,834,503 A | 11/1998 | Kelly et al. | |
| 5,864,141 A | 1/1999 | Majewski et al. | |
| 5,882,335 A * | 3/1999 | Leone et al. | 604/103.02 |
| 5,919,135 A * | 7/1999 | Lemelson | 600/407 |
| 5,924,997 A | 7/1999 | Campbell | |
| 5,932,879 A | 8/1999 | Raylman et al. | |
| 5,952,329 A | 9/1999 | Cincotta et al. | |
| 5,976,496 A | 11/1999 | Dean et al. | |
| 6,033,436 A * | 3/2000 | Steinke et al. | 623/1.15 |
| 6,042,603 A | 3/2000 | Fisher et al. | |
| 6,054,449 A | 4/2000 | Robinson et al. | |
| 6,076,009 A | 6/2000 | Raylman et al. | |
| 6,180,402 B1 | 1/2001 | Granville et al. | |
| 6,211,349 B1 | 4/2001 | Dale et al. | |
| 6,238,348 B1 | 5/2001 | Crowley et al. | |
| 6,246,901 B1 * | 6/2001 | Benaron | 600/431 |
| 6,286,514 B1 * | 9/2001 | Lemelson | 128/899 |
| 6,295,680 B1 * | 10/2001 | Wahl et al. | 600/431 |
| 6,547,812 B1 * | 4/2003 | Hu | 623/1.11 |
| 6,716,410 B1 | 4/2004 | Witztum et al. | |
| 6,764,501 B2 * | 7/2004 | Ganz | 607/92 |
| 6,782,289 B1 | 8/2004 | Strauss | |
| 6,816,743 B2 | 11/2004 | Moreno et al. | |
| 6,869,590 B2 | 3/2005 | Edwards et al. | |
| 6,894,161 B2 * | 5/2005 | Desjardins et al. | 540/125 |
| 6,906,050 B2 | 6/2005 | Robinson | |
| 7,373,197 B2 | 5/2008 | Daighighian et al. | |
| 2002/0115649 A1 | 8/2002 | Woodburn et al. | |
| 2002/0168317 A1 | 11/2002 | Daighighian et al. | |
| 2003/0138411 A1 | 7/2003 | Greaves | |
| 2003/0152513 A1 | 8/2003 | Blankenberg et al. | |
| 2003/0235531 A1 | 12/2003 | Adair | |
| 2004/0057900 A1 | 3/2004 | Edwards et al. | |
| 2004/0086495 A1 | 5/2004 | Kriegelstein et al. | |
| 2005/0244336 A1 | 11/2005 | Low | |
| 2006/0073100 A1 | 4/2006 | Fischman et al. | |
| 2007/0258906 A1 | 11/2007 | Fischman et al. | |
| 2007/0264194 A1 | 11/2007 | Liu et al. | |

FOREIGN PATENT DOCUMENTS

| | | | |
|---|---|---|---|
| WO | 84/02069 A1 | 6/1984 | |
| WO | WO 90/05748 | 5/1990 | |
| WO | 95/00605 A1 | 1/1995 | |
| WO | 99/12579 A1 | 3/1999 | |
| WO | WO 01/32070 | 5/2001 | |
| WO | 03/003975 A2 | 1/2003 | |
| WO | WO 03/020765 | 3/2003 | |
| WO | WO 03/077723 | 9/2003 | |

OTHER PUBLICATIONS

Araki, N., et al., "Macrophage Scavenger Receptor Mediates the Endocytic Uptake and Degradation of Advanced Glycation End Products of the Maillard Reaction," *Eur. J. Biochem.*, 230: 408-415, 1995.

Arbustini, E., et al., "Comparison of Coronary Lesions Obtained By Directional Coronary Atherectomy in Unstable Angina, Stable Angina, and Restenosis After Either Atherectomy or Angioplasty," *The American Journal of Cardiology*, 75: 675-682, 1995.

Arroyo, L.H., et al., "Mechanisms of Plaque Rupture: Mechanical and Biologic Interactions," *Cardiovascular Research*, 41: 369-375, 1999.

Bachor, R., et al., "Photosensitized Destruction of Human Bladder Carcinoma Cells Treated With Chlorin $e_6$-conjugated Microspheres," *Proc. Natl. Acad. Sci. USA*, 88: 1580-1584, 1991.

Ball, D.J., et al., "The Induction of Apoptosis by a Positively Charged Methylene Blue Derivative,"*Journal of Photochemistry and Photobiology B: Biology*, 42: 159-163, 1998.

Basu, S., "Enhanced Intracellular Delivery of Doxorubicin by Scavenger Receptor-Mediated Endocytosis for Preferential Killing of Histiocytic Lymphoma Cells in Culture," *FEBS Letters*, 342: 249-254, 1994.

Basu, S. K., "Receptor-Mediated Endocytosis of Macromolecular Conjugates in Selective Drug Delivery,"*Biochemical Pharmacology*, 40(9): 1941-1946, 1990.

Casscells, W., et al., "Thermal Detection of Cellular Infiltrates in Living Atherosclerotic Plaques: Possible Implications for Plaque Rupture and Thrombosis," *Lancet*, 347: 1447-1451, 1996.

Del Governatore, M., et al., "Targeted Photodestruction of Human Colon Cancer Cells Using Charged 17.1A Chlorin $e_6$ Immunoconjugates," *British Journal of Cancer*, 82(1): 56-64, 2000.

De Smith, P.C., "LDL-Mediated Drug Targeting," *Critical Rev. In Ther. Drug Carrier Syst.*, 7(2): 99-120, 1990.

Dougherty, T.J., et al., "Photodynamic Theory," *Journal of the National Cancer Institute*, 90(12): 889-905, 1998.

Dvorak, H.F., et al., "Identification and Characterization of the Blood Vessels of Solid Tumors that are Leaky to Circulating Macromolecules," *American Journal of Pathology*, 133(1): 95-109, 1988.

Eisenbrand, G., et al., "Modes of Action and Perspectives in the Use of Hormone Receptor Affine Carrier Molecules," *Acta Oncologica*, 28: 203-211, 1989.

Falk, E., "Morphologic Features of Unstable Atherothrombotic Plaques Underlying Acute Coronary Syndromes," *The American Journal Of Cardiology*, 63: 114E-120E,1989.

Farb, A., et al., "Sudden Coronary Death: Frequency of Active Coronary Lesions, Inactive Coronary Lesions, and Myocardial Infarction," *Circulation*, 92(7): 1701-1709, 1995.

Ferrario, A., et al., "Systemic Toxicity in Mice Induced by Localized Porphyrin Photodynamic Therapy," *Cancer Research*, 50: 539-543, 1990.

Gijsens, A., et al., "Photocytotoxic action of EGF-PVA-Sn(IV)chlorin $e_6$ and EGF-dextran-Sn(IV)chlorin $e_6$ in internalizable conjugates on A431 cells," *Int. J. Oncol.*, 13: 1171-1177, 1998.

Gomer, C.J., "Preclinical Examination of First and Second Generation Photosensitizers Used in Photodynamic Therapy," *Photochemistry and Photobiology*, 54(6): 1093-1107, 1991.

Gutstein, D., et al., "Pathophysiology and Clinical Significance of Atherosclerotic Plaque Rupture," *Cardiovascular Research*, 41: 323-333, 1999.

Haberland, M.E., et al., "Malondialdehyde Modification of Lipoprotein(a) Produces Avid Uptake by Human Monocyte-Macrophages," *The Journal of Biological Chemistry*, 267(6): 4143-4151,1992.

Haberland, M.E., et al., "Scavenger Receptor-Mediated Recognition of Maleyl Bovine Plasma Albumin and the Demaleylated Protein in Human Monocyte Macrophages," *Proc. Natl. Acad. Sci. USA*, 82: 2693-2697, 1985.

Haberland, M.E., et al., "Specificity of Receptor-Mediated Recognition of Malondialdehyde Modified Low Density Lipoproteins," *Proc. Natl. Acad. Sci. USA*, 79: 1712-1716, 1982.
Hamblin, M.R., et al., "Biodistribution of Charged 17.1A Photoimmunoconjugates in a Murine Model of Hepatic Metastasis of Colorectal Cancer," *British Journal of Cancer*, 83(11): 1544-1551, 2000.
Hamblin, M.R., et al., "In Vivo Fluorescence Imaging of the Transport of Charged Chlorin $e_6$ Conjugates in a Rat Orthotopic Prostate Tumour," *British Journal of Cancer*, 81(2): 261-268, 1999.
Hamblin, M.R., et al., "On the Mechanism of the Tumour-Localising Effect in Photodynamic Therapy," *J. Photochem. Photobiol. B: Biol.*, 23: 3-8, 1994.
Hamblin, M.R., et al., "Photosensitizer Targeting in Photodynamic Therapy: I. Conjugates of Haematoporphyrin with Albumin and Transferrin," *Journal of Photochemistry and Photobiology B: Biology*, 26: 45-56, 1994.
Hamblin, M.R., et al., "Photosensitizer Targeting in Photodynamic Therapy: II. Conjugates of Haematoporphyrin with Serum Lipoproteins," *Journal of Photochemistry and Photobiology B: Biology*, 26: 147-157, 1994.
Hamblin, M.R., et al., "Scavenger-Receptor Targeted Photodynamic Therapy," *Photochemistry and Photobiology*, 72(4): 533-540, 2000.
Hasan, T., "Photosensitizer Delivery Mediated by Macromolecular Carrier Systems," In: B.W. Henderson and T.J. Dougherty (eds.), *Photodynamic Therapy: Basic Principles and Clinical Applications*, 187-200: Marcel Decker, 1992.
Hayase, M., et al., "Photoangioplasty with Local Motexafin Lutetium Delivery Reduces Macrophages in a Rabbit Post-Balloon Injury Model," *Cardiovascular Research*, 49: 449-455, 2001.
Hunt, D., et al., "Sensitivity of Activated Murine Peritoneal Macrophages to Photodynamic Killing with Benzoporphyrin Derivitative," *Photochemistry and Photobiology*, 61(4): 417-421, 1995.
Joseph, I.B., et al., "Macrophage Role in the Anti-Prostate Cancer Response to One Class of Antiangiogenic Agents," *Journal of the National Cancer Institute*, 90(21): 1648-1653, 1998.
Kessel, D., et al., "The Role of Subcellular Localization in Initiation of Apoptosis by Photodynamic Therapy," *Photochemistry and Photobiology*, 65(3): 422-426,1997.
Kessel, D., et al., "Mitochondrial Photodamage and PDT-Induced Apoptosis," *Journal of Photochemistry and Photobiology B: Biology*, 42: 89-95, 1998.
Korbelik, M., et al., "Photofrin Uptake by Murine Macrophages," *Cancer Research*, 51: 2251-2255, 1991.
Krieger, M., "Molecular Flypaper and Atherosclerosis: Structure of the Macrophage Scavenger Receptor," *Trends Biochem Sci.*, 17: 141-146, 1992.
Krieger, M., "The Other Side of Scavenger Receptors: Pattern Recognition for Host Defense," *Curr. Opin In Lipidiol.*, 8: 275-280, 1997.
Krinick, N.L., "A Polymeric Drug Delivery System for the Simultaneous Delivery of Drugs Activatable by Enzymes and/or Light," *J. Biomater. Sci Polymer Edn.*, 5(4): 303-324, 1994.
Litvack, F., et al., "Effects of Hematoporphyrin Derivative and Photodynamic Therapy on Atherosclerotic Rabbits," *Am. J. Cardiol.*, 56: 667-671, 1985.
Molpus, K., et al., "Intraperitoneal Photoimmunotherapy of Ovarian Carcinoma Xenografts in Nude Mice Using Charged Photoimmunoconjugates," *Gynecologic Oncology*, 76: 397-404, 2000.
Murakami, M., et al., "Scavenger Receptor for Malondialdehyde-Modified High Density Lipoprotein on Rat Sinusoidal Liver Cells," *Biochemical and Biophysical Research Communications*, 137(1): 29-35, 1986.
Mukhopadhyay, B., et al., "Enhancement of Tumouricidal Activity of Daunomycin by Receptor-Mediated Delivery," *Biochemical Pharmacology*, 46(5): 919-924, 1993.
Mukhopadhyay, A., et al., "Scavenger-Receptor-Mediated Delivery of Daunomycin Elicits Selective Toxicity Towards Neoplastic Cells of Macrophage Lineage," *Biochem. J.*, 284: 237-241, 1992.
Nagae, T., "Selective Targeting and Photodynamic Destruction of Intimal Hyperplasia by Scavenger-Receptor Mediated Protein-Chlorin e6 Conjugates," *J. Cardiovasc. Surg.*, 39(6): 709-715, 1998.
Ochsner, M., "Photophysical and Photobiological Processes in the Photodynamic Therapy of Tumours," *Journal of Photochemistry and Photobiology B: Biology*, 39: 1-18, 1997.
Parthasarathy, S., et al., "The Role of Oxidized Low-Density Lipoproteins in the Pathogenesis of Atherosclerosis," *Annu. Rev. Med.*, 43: 219-225, 1992.
Plutzky, J., "Atherosclerotic Plaque Rupture: Emerging Insights and Opportunities," *Am. J. Cardiol.*, 84(1A): 15J-20J, 1999.
Polo, L., et al., "Liposome-Delivered I-Labelled Zn(II)-phthalocyanine as a Radiodiagnostic Agent for Tumours," *Cancer Letters*, 109: 57-61, 1996.
Putman, D.A., et al., "Intracellularly Biorecognizable Derivatives of 5-Fluorouracil: Implications for Site Specific Delivery in the Human Condition," *Biochemical Pharmacology*, 52: 957-962, 1996.
Rabbani, R., et al., "Strategies to Achieve Coronary Arterial Plaque Stabilization," *Cardiovascular Research*, 41: 402-417, 1999.
Resnick, D., et al., "Secreted Extracellular Domains of Macrophage Scavenger Receptors Form Elongated Trimers Which Specifically Bind Crocidolite Asbestos," *The Journal of Biological Chemistry*, 268(5): 3538-3545, 1993.
Rockson, S., et al., "Photoangioplasty: An Emerging Clinical Cardiovascular Role for Photodynamic Therapy," *Circulation*, 102: 591-596, 2000.
Sacks, F.M. et al., "Effect of Pravastatin on Coronary Disease Events in Subgroups Defined by Coronary Risk Factors: The Prospective Pravastatin Pooling Project," *Circulation*, 102(16): 1893-1900, 2000.
Schmidt-Erfurth, U., et al., "Photodynamic Targeting of Human Retinoblastoma Cells Using Covalent Low-Density Lipoprotein Conjugates," *British Journal of Cancer*, 75(1): 54-61, 1997.
Shah, P., et al., "Human Monocyte-Derived Macrophages Induce Collagen Breakdown in Fibrous Caps of Atherosclerotic Plaques: Potential Role of Matrix-Degrading Metalloproteinases and Implications for Plaque Rupture," *Circulation*, 92(6): 1565-1569, 1995.
Shah, P., et al., "Plaque Disruption and Thrombosis: Potential Role of Inflammation and Infection," *Cardiol. In Rev.*, 8(1): 31-39, 2000.
Spokojny, A., et al., "Uptake of Hematoporphyrin Derivative by Atheromatous Plaques: Studies in Human in Vitro and Rabbit in Vivo," *J. Am. Coll. Cardiol.*, 8(6): 1387-1392, 1986.
Svinth, M., et al., "Differences in Cytotoxicity of Native and Engineered RIPs Can Be Used to Assess Their Ability to Reach Cytoplasm," *Biochemical and Biophysical Research Communications*, 249: 637-642, 1998.
Takata, K., et al., "Scavenger Receptor-Mediated Recognition of Maleylated Albumin and its Relation to Subsequent Endocytic Degradation," *Biochimica et Biophysica Acta*, 984: 273-280, 1989.
van der Wal, A.C., et al., "Atherosclerotic Plaque Rupture-Pathologic Basis of Plaque Stability and Instability," *Cardiovascular Research*, 41: 334-344, 1999.
van der Wal, A.C., "Fibrous and Lipid-Rich Atherosclerotic Plaques Are Part of Interchangeable Morphologies Related to Inflammation: a Concept," *Coron. Artery Dis.*, 5(6): 463-469, 1994.
Wood, S., et al., "The Subcellular Localization of Zn(II) Phthalocyanines and Their Redistribution on Exposure to Light," *Photochemistry and Photobiology*, 65(3): 397-402, 1997.
Brasseur, N. et al., "Receptor-Mediated Targeting of Phthalocyanines to Macrophages Via Covalent Bonding Coupling to Native or Maleylated Bovine Serum Albumin," *Photochem. & Photobiol.*, 69(3): 345.52, 1999.
Freeman, M., "Scavenger Receptors in Atherosclerosis," *Curr. Opin. Hematol.*, 4: 41-47, 1997.
Woodburn, K. et al.,"Phototherapy of Cancer and Atheromatous Plaque with Texaphyrins,"*J. Clin. Laser Med. Surg.*, 14(5): 343-48, 1996.
Tawakol, Ahmed et al., "Intravascular detection of inflamed atherosclerotic plaques using a fluorescent photosensitizer targeted to the scavenger receptor"; Photochem. Photobiol. Sci., 2008, 7, 33-39.
Tawakol, Ahmed et al., "Photosensitizer delivery to vulnerable atherosclerotic plaque: comparison of macrophage-targeted conjugate versus free chlorine(e6)"; Journal of Biomedical Optics 11(2), 021008 (Mar./Apr. 2006).
Hamblin et al., "Scavenger-Receptor Targeted Photodynamic Therapy." Photochemistry and Photobiology, 2000, 72(4): 533-540.

Nagae et al. "Selective targeting and photodynamic destruction of intimal hyperplasia by scavenger-receptor mediated protein-chlorin e6 conjugates." J. Cardiovasc Surg 1998: 39: 709-15.

James H. Chesebro et al., "Antithrombotic Therapy & Progression of Coronary Artery Disease: Antiplatelet Versus Antithrombins," 86(6) Circulation III-100-III-110 (1992).

Lynn Corcoran et al., "Differential regulation of CD36 expression in antigen-presenting cells: Oct-2 dependence in B lymphocytes but not dendritic cells or macrophages," 14(10) Int'l Immunology 1099-1104 (2002).

International Search Report, International Application No. PCT/US02/38852 (May 3, 2001).

International Preliminary Examination Report, International Application No. PCT/US02/38852 (Mar. 17, 2010).

Communication, European Patent Application No. 02795747.1-2305 (Jan. 21, 2008).

Communication, European Patent Application No. 02795747.1-2305 (May 15, 2008).

Official Action, Japanese Patent Application No. 2003-575782 (Nov. 19, 2008).

Farhad Daghighian et al., "Intraoperative beta probe: A device for detecting tissue labeled with positron or electron emitting isotopes during surgery," 21 Medical Physics 153 (1994) (doi:10.1118/1.597240).

Valentin Fuster et al., "The Pathogenesis of Coronary Artery Disease & the Acute Coronary Syndromes," 326(4) New England J. Med. 242-50 (Jan. 23, 1992).

Valentin Fuster et al., "The Pathogenesis of Coronary Artery Disease & the Acute Coronary Syndromes," 326(5) New England J. Med. 310-18 (Jan. 30, 1992).

* cited by examiner

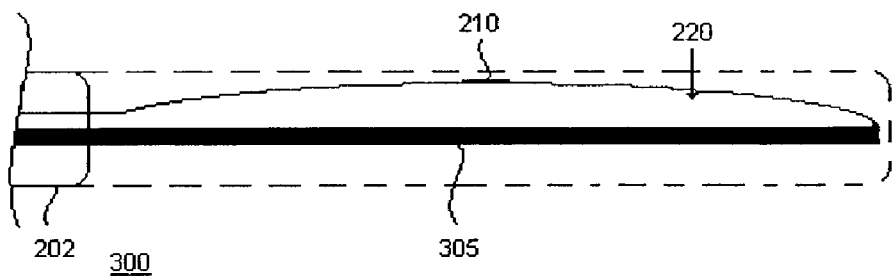
FIG. 3A
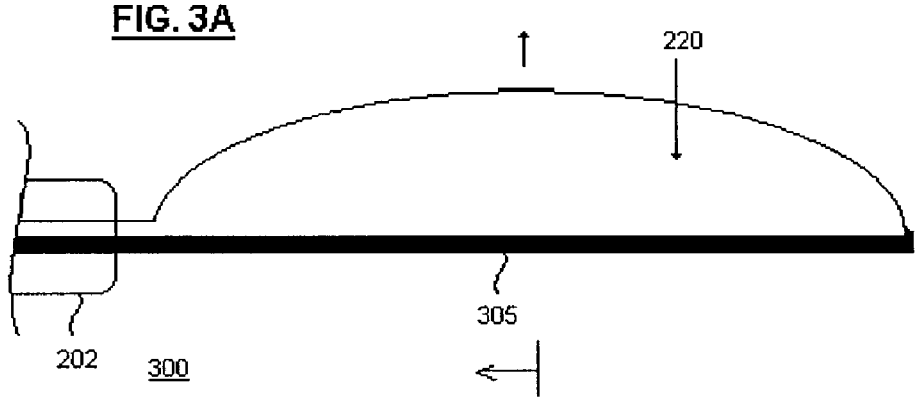
FIG. 3B
FIG. 3C
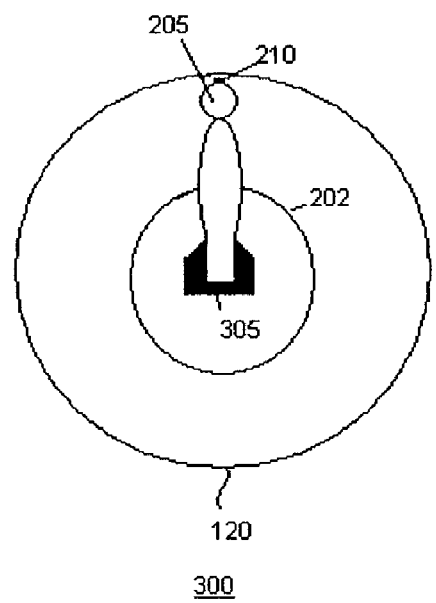
FIG. 3C

400

400

A.

B.

Pilot PDT experiment on 2 atherosclerotic animals (1 PDT treated, 1 that received light but no conjugate)

15 min.　　　　2 hrs.　　　　ex-vivo

DEVICES FOR DETECTION AND THERAPY OF ATHEROMATOUS PLAQUE

RELATED APPLICATIONS/PATENTS & INCORPORATION BY REFERENCE

This application is division of U.S. application Ser. No. 10/215,958, filed Aug. 9, 2002, now abandoned which is a continuation-in-part application of U.S. application Ser. No. 10/163,744, filed on Jun. 4, 2002, now abandoned which claims priority to U.S. Provisional Application No. 60/295,627, filed Jun. 4, 2001, and U.S. Provisional Application No. 60/365,673, filed Mar. 15, 2002, the contents of which are expressly incorporated herein by reference. Reference is also made herein to PCT/US98/18685, published as WO 99/12579 on Mar. 18, 1999, the contents of which are expressly incorporated herein by reference.

Each of the applications and patents cited in this text, as well as each document or reference cited in each of the applications and patents (including during the prosecution of each issued patent; "application cited documents"), and each of the PCT and foreign applications or patents corresponding to and/or claiming priority from any of these applications and patents, and each of the documents cited or referenced in each of the application cited documents, are hereby expressly incorporated herein by reference. More generally, documents or references are cited in this text, either in a Reference List before the claims, or in the text itself; and, each of these documents or references ("herein-cited references"), as well as each document or reference cited in each of the herein-cited references (including any manufacturer's specifications, instructions, etc.), is hereby expressly incorporated herein by reference.

STATEMENT OF RIGHTS TO INVENTIONS MADE UNDER FEDERALLY SPONSORED RESEARCH

This work was supported by the government, in part, by a grant from the United States Department of Defense, Grant No. 17-99-2-9001. The government has certain rights to this invention.

FIELD OF THE INVENTION

The present invention relates to devices for detection and therapy of active atheromatous plaque and/or thin-capped fibro-atheroma ("vulnerable plaque"), using selectively targeted fluorescent, radiolabeled, or fluorescent and radiolabeled compositions. The present invention further relates to methods and devices for detection and therapy of active atheromatous plaques and/or vulnerable plaques, using selectively targeted beta-emitting compositions, optionally comprising fluorescent compositions. Other aspects of the invention are described in or are obvious from the following disclosure (and within the ambit of the invention).

BACKGROUND OF THE INVENTION

Cardiovascular disease remains the leading cause of morbidity and mortality in the United States; approximately 2600 deaths each day are the result of cardiovascular disease. In the United States, 50-60% of heart attacks occur in people without documented cardiovascular disease. A chief contributor to the pathology of the disease is the formation of atherosclerotic or "atheromatous" plaques in the coronary arteries (Farb et al. (1995) Circulation 92:1701-1709). An atheromatous plaque refers to a wide range of coronary lesions, from subtle collections of lipid, to obstructive coronary lesions that cause angina.

Atheromatous plaques can be active, and prone to rupture, or inactive and relatively stable. The progression of coronary atherosclerotic disease can be divided into five phases (Fuster et al. (1992) N Engl J Med 326:242-250). Phase I is represented by a small plaque that is present in most people under the age of 30 years, regardless of their country of origin, and that usually progresses slowly (i.e., type I-III lesions). Phase 2 is represented by a plaque, not necessarily very stenotic, with a high lipid content that is prone to rupture (i.e., type IV and Va lesions). The plaque of phase 3 may have predisposition to change in its geometry and to formation of mural thrombus, these processes by definition represent phase 3 (i.e., type I lesion), with a subsequent increase in stenosis, possibly resulting in angina, or ischemic sudden death. The mural and occlusive thrombi from plaques of phases 3 and 4, being organized by connective tissue, may contribute to the progression of the atherosclerotic process represented by severely stenotic or occlusive plaques of phase 5 (i.e., types Vb and Vc lesions). The severely stenotic plaques of phase 5, by a phenomenon of stasis and/or de-endothelialization, can become complicated by a thrombus and/or rapid myoproliferative response, also leading to an occlusive plaque of phase 5. Of interest is that about two thirds of coronary occlusions are the result of this late stenotic-type of plaque and are unrelated to plaque disruption. Unlike the rupture of less-stenotic lipid-rich plaques, leading to occlusion and subsequent infarction or other acute coronary syndromes, this process of occlusion from late stenotic plaques tends to be silent because the preceding severe stenosis and ischemia enhance protective collateral circulation (Fuster et al., (1992) N Engl J Med 326:242-250; Chesebro et al. (1992) Circulation 86 (suppl. 111)).

In general, atheromatous plaques characteristically comprise a fibrous cap surrounding a central core of extracellular lipids and debris located in the central portion of the thickened vessel intima, which is known as the "atheroma." On the luminal side of the lipid core, the fibrous cap is comprised mainly of connective tissues, typically a dense, fibrous, extracellular matrix made up of collagens, elastins, proteoglycans and other extracellular matrix materials.

At the edges of the fibrous cap overlying an active atheromatous plaque, the lipid core comprises the shoulder region and is enriched with macrophages. The macrophages continually phagocytose oxidized LDL through scavenger receptors, which have a high ligand specificity for oxidized LDL. Continuous phagocytosis results in the formation of foam cells, a hallmark of the atherosclerotic plaque (Parthasarathy et al. (1992) Annu Rev Med 43:219-225). Foam cells, together with the binding of extracellular lipids to collagen fibers and proteoglycans, play an important role in the formation and growth of the lipid-rich atheroma.

Histopathologic examination of atheromatous plaques has revealed substantial variations in the thickness of fibrous caps, the size of the atheromas, the extent of dystrophic calcification and the relative contribution of major cell types (van der Wal et al. (1994) Coron Artery Dis 5:463-469). Resident cells present in active atheromatous plaques include a significant population of inflammatory cells, such as monocytes/macrophages and T lymphocytes. The emigration of monocytes into the arterial wall, and their subsequent differentiation into macrophages and ultimately foam cells, remains one of the earliest steps in plaque formation. Once there, these cells play a critical role in secreting substances that further contribute to atherosclerosis.

New therapies designed to target the genesis of atheromatous plaque and/or thrombus formation, or processes associated with atheromatous plaque and/or thrombus formation, as well as internal inflammation and infection are needed.

Current therapies designed to ameliorate the occlusive effects of atheromatous plaques on coronary blood flow, such as coronary artery bypass surgery and percutaneous transluminal coronary angioplasty, do not always prevent the incidence of acute coronary syndrome. Moreover, at least 50% of patients receiving angioplasty must return for a further procedure between 6 months to one year after the initial procedure. Acute coronary syndrome covers a group of sudden-onset coronary diseases, including unstable angina, acute myocardial infarction and sudden cardiac death. The causative agent of acute coronary syndrome is fissure, erosion or rupture of a specific kind of atheromatous plaque known as a "vulnerable plaque." Vulnerable plaques are responsible for the majority of heart attacks, strokes, and cases of sudden death.

Post-mortem evidence suggests that vulnerable plaque rupture occurs in areas of the coronary arteries that are less than about 50% stenosed. Thus, angioplasty and bypass procedures, which are carried out on severely stenosed arteries, rarely remove vulnerable plaques or reduce the incidence of acute coronary syndrome (Plutzky (1999) Am J Cardiol 84:15J-20J). Even with currently available therapeutic approaches, such as lipid lowering, angioplasty and bypass, an unacceptably high incidence of acute coronary syndrome remains (Sacks et al. (2000) Circulation 102:1893-1900).

A vulnerable plaque is structurally and functionally distinguishable from a stable atheromatous plaque. For example, several histologic features distinguish a vulnerable plaque from a stable atheromatous plaque. A vulnerable plaque is characterized by an abundance of inflammatory cells (e.g., macrophages and/or T cells), a large lipid pool, and a thin fibrous cap.

Pathologic studies have provided a further understanding of why vulnerable plaques have a higher propensity for rupture than other atheromatous plaques. The thickness and integrity of the fibrous cap overlying the lipid-rich core is a principal factor in the stability of the plaque. Vulnerable plaques prone to rupture can be characterized as having thinner fibrous areas, increased numbers of inflammatory cells (e.g., macrophages and T cells), and a relative paucity of vascular smooth muscle cells. Vascular smooth muscle cells are the major source of extra cellular matrix production, and therefore, the absence of vascular smooth muscle cells from a vulnerable plaque contributes to the lack of density in its fibrous cap.

While the fibrous tissue within the cap provides structural integrity to the plaque, the interior of the atheroma is soft, weak and highly thrombogenic. It is rich in extracellular lipids and substantially devoid of living cells, but bordered by a rim of lipid-laden macrophages (van der Wal et al. (1999) Cardiovasc Res 41:334-344). The lipid core is a highly thrombogenic composition, rich in tissue factor, which is one of the most potent procoagulants known. The lesional macrophages and foam cells produce a variety of procoagulant substances, including tissue factor. The fibrous cap is the only barrier separating the circulation from the lipid core and its powerful coagulation system designed to generate thrombus. Essentially, the rapid release of procoagulants into the blood stream at the site of rupture forms an occlusive clot, inducing acute coronary syndrome. Thus, the thinner the fibrous cap, the greater the instability of the thrombogenic lipid core and the greater the propensity for rupture and thrombosis.

Several factors can contribute to the weakened state of the fibrous cap. In particular, inhibition of extracellular matrix production or degradation of extracellular matrix components adversely impacts the structural composition of the fibrous cap. Macrophages and T lymphocytes have been identified as the dominant cell types at the site of plaque rupture or superficial erosion, and each of these inflammatory cells contributes to the inhibitory and/or degradative pathways. Accelerated degradation of collagen and other matrix components is carried out by macrophage proteases, such as matrix metalloproteinases ("MMPs"), which are secreted at the site of the plaque. MMPs constitute an extensive family of enzymes, including interstitial collagenase (e.g., MMP-I), gelatinases (e.g., MMP-2, MMP-9), and stromelysin (e.g., MMP-3). Stromelysins can activate other members of the MMP family, causing degradation among many matrix constituents. The presence of T cells in the plaque can further contribute to weakening of the fibrous cap. Activated T cells produce and secrete interferon-$\gamma$, a potent inhibitor of collagen synthesis. Thus, the T lymphocytes represent a potentially large source of interferon-$\gamma$ that can negatively regulate matrix production. Plaque rupture sites are further characterized by expression of major histocompatibility complex genes, (e.g., human lymphocyte antigen-DR on inflammatory cells and adjacent smooth muscle cells), indicating an active inflammatory reaction that also weakens the fibrous cap.

Present methods of plaque detection, several of which are discussed herein, are inadequate for detecting the genesis of atheromatous plaque and/or thrombus formation, or processes associated with atheromatous plaque and/or thrombus formation, as well as internal inflammation and infection. Present methods of plaque detection are also inadequate for detecting vulnerable plaques.

Common methods of plaque detection include angiography and angioscopy. Except in rare circumstances, angiography gives almost no information about the characteristics of plaque components. Angiography is only sensitive enough to detect hemodynamically significant lesions (>70% stenosis), which account for approximately 33% of acute coronary syndrome cases. Angioscopy is a technique based on fiber-optic transmission of visible light that provides a small field of view with relatively low resolution for visualization of interior surfaces of plaque and thrombus. Because angioscopic visualization is limited to the surface of the plaque, it is insufficient for use in detecting actively forming atheromatous and/or vulnerable plaques.

Several methods are being investigated for their ability to identify atheromatous plaques. However, none has proven to be sufficiently sensitive to identify vulnerable plaques or monitor the formation thereof. One such method, intravascular ultrasound ("IVUS") uses miniaturized crystals incorporated at catheter tips and provides real-time, cross-sectional and longitudinal, high-resolution images of the arterial wall with three-dimensional reconstruction capabilities. IVUS can detect thin caps and distinguish regions of intermediate density (e.g., intima that is rich in smooth muscle cells and fibrous tissue) from echolucent regions, but current technology does not determine which echolucent regions are composed of cholesterol pools rather than thrombosis, hemorrhage, or some combination thereof. Moreover, the spatial resolution (i.e., approximately 2 cm) does not distinguish the moderately thinned cap from the high risk cap (i.e., approximately 25-75 µm) and large dense calcium deposits produce acoustic echoes which "shadow" so that deeper plaque is not imaged.

Intravascular thermography is based on the premise that atheromatous plaques with dense macrophage infiltration give off more heat than non-inflamed plaque (Casscells et al. (1996) Lancet. 347:1447-1451). The temperature of the plaque is inversely correlated to cap thickness. However, thermography may not provide information about eroded but non-inflamed lesions, vulnerable or otherwise, having a propensity to rupture.

Optical coherence tomography ("OCT") measures the intensity of reflected near-infrared light from tissue. It provides images with high resolution that is approximately 10 to 20 times higher than that of IVUS resolution. OCT is primarily used for assessment of atherosclerotic plaque morphology. However, long image acquisition time, high costs, limited penetration and a lack of physiologic data render this approach undesirable for detection of actively forming atheromatous and/or vulnerable plaques.

Raman spectroscopy utilizes Raman effect: a basic principle in photonic spectroscopy named after its inventor. Raman effect arises when an incident light excites molecules in a sample, which subsequently scatter the light. While most of this scattered light is at the same wavelength as the incident light, some is scattered at a different wavelength. This shift in the wavelength of the scattered light is called Raman shift. The amount of the wavelength shift and intensity depends on the size, shape, and strength of the molecule. Each molecule has its own distinct "fingerprint" Raman shift. Raman spectroscopy is a very sensitive technique and is capable of reporting an accurate measurement of chemical compounds. Conceivably, the ratio of lipid to proteins, such as collagen and elastin, might help detect vulnerable plaques with large lipid pools. However, it is unlikely that actively forming and/or vulnerable plaques will be reliably differentiated from stable plaques based solely on this ratio.

All of the existing technologies and methods used to date are structural and therefore may be unable to detect actively forming or vulnerable plaques. All vascular detection agents known in the art involve the use of external imaging devices, such as gamma or positron cameras. The usefulness of such agents is limited and will not accurately detect plaque or thrombus due to the background activity from the surrounding tissue. Although 3D imaging via PET and SPECT is presently in use, the small size of the arteries as compared to the scatter from the large surrounding tissues lowers the utility of these imaging modalities as well.

Radiation-based methods for detection of diseased tissue are known in the art (U.S. Pat. No. 4,995,396). The devices of U.S. Pat. No. 4,995,396 are not designed to identify vulnerable plaques and further, U.S. Pat. No. 4,995,396 does not disclose intra-arterial beta probes. Use of beta-sensitive probes for the detection of plaques has been reviewed (Daghighian et al. Med Phys. 21:153-7(1994); U.S. Pat. Nos. 5,008,546, 5,744,805, 5,932,879, 6,076,009 and 6,295,680). U.S. Pat. No. 5,744,805 relates to an ion-implanted silicon radiation detector located at the tip of a probe with a preamplifier contained within the body of the probe, connected to the detector as well as external electronics for signal handling. U.S. Pat. Nos. 5,744,805 and 5,932,879 provide radiopharmaceuticals for detecting diseased tissue, such as a cancerous tumor, followed by the use of a probe with one or more ion-implanted silicon detectors at its tip to locate the radiolabeled diseased tissue; the detector is preferentially responsive to beta emissions. U.S. Pat. Nos. 6,076,009, 5,568,532 and 5,864,141 relate to further designs for probes containing scintillators and photomultiplier tubes connected thereto. However, these techniques lack the precision of selective targeting as first described herein.

Photodynamic therapy ("PDT") employs photoactivatable compounds known as photosensitizers to selectively target and destroy cells. Therapy involves delivering visible light of the appropriate wavelength to excite the photosensitizer molecule to the excited singlet state. This excited state can then undergo intersystem crossing to the slightly lower energy triplet state, which can then react further by one or both of two pathways, known as Type I and Type II photoprocesses (Ochsner (1997) J Photochem Photobiol B 39:1-18). The Type I pathway involves electron transfer reactions from the photosensitizer triplet to produce radical ions which can then react with oxygen to produce cytotoxic species such as superoxide, hydroxyl and lipid derived radicals. The Type II pathway involves energy transfer from the photosensitizer triplet to ground state molecular oxygen (triplet) to produce the excited state singlet oxygen, which can then oxidize many biological molecules such as proteins, nucleic acids and lipids, and lead to cytotoxicity.

Photodynamic therapy (PDT) has recently gained regulatory approval in the United States for treatment of esophageal cancer and in other countries for several other types of cancers (Dougherty et al. (1998) J Natl Cancer Inst 90:889-905). Certain photosensitizers accumulate preferentially in malignant tissues (Hamblin & Newman (1994) J Photochem Photobiol B 23:38), creating the advantage of dual selectivity: not only is the photosensitizer ideally specific for the target tissue, but the light can also be accurately delivered to the target tissue, thereby limiting the area within which the toxic effects of the photosensitizer are released.

Photodynamic therapy has been applied in cardiovascular medicine for two broad indications: treatment of atherosclerosis ("photoangioplasty") and inhibition of restenosis due to intimal hyperplasia after vascular interventions (Rockson et al. (2000) Circulation 102:591-596, U.S. Pat. Nos. 5,116,864, 5,298,018, 5,308,861, 5,422,362, 5,834,503 and 6,054,449). Hematoporphyrin derivative ("HpD") was the first of a number of photosensitizers with demonstrable, selective accumulation within atheromatous plaques (Litvack et al. (1985) Am J Cardiol 56:667-671). Subsequent studies have underscored the affinity of porphyrin derivatives for atheromatous plaques in rabbits and miniswine. There is maximal photosensitizer accumulation within the arterial intimal surface layers, which is diminished in comparison to the arterial media. Both HpD and Photofrin, a more purified derivative of HpD, also display in vitro preferential uptake by human atheromatous plaques. However, there is generally a relative lack of selectivity of most photosensitizers for atheromatous plaques and more particularly for vulnerable plaques. Moreover, methods known in the art for photodynamic destruction of atherosclerotic plaques generally fail as a result of the inflammatory response that follows PDT.

Recently, interventional strategies leading to vulnerable plaque stabilization have become an active area of research (Rabbani & Topol (1999) Cardiovasc Res 41:402-417). A therapy designed to detect, stabilize and reduce or eliminate active atheromatous and/or vulnerable plaques without inducing an inflammatory response would be highly desirable.

OBJECT AND SUMMARY OF THE INVENTION

The present invention provides methods for selectively targeting radiolabeled compositions, preferably comprising beta-emitting radiolabels, and optionally photodynamic compositions, to inflammatory components (e.g., inflammatory cells, proteases and lipids) of active atheromatous and/or vulnerable plaques as well as devices for the detection and therapy thereof.

In one aspect, detection of active atheromatous and/or vulnerable plaque can be carried out using a specially designed intravascular device that detects a nuclear signal, preferably from a radiolabeled composition, and even more preferably from a beta-emitting composition, localized to the plaque.

It now been determined that intravascular beta-emitting agents can be detected within atheromatous and/or vulnerable plaques by beta detection devices of the present invention. The use of a beta-emitting composition targeted to the active atheromatous and/or vulnerable plaque should improve detection of the same due to the improved sensitivity and reduced distance necessary to accurately observe the area of the plaque. Beta-emission based methods and devices of the present invention provide accurate delineation of plaque areas, which will improve therapy and fosters early detection.

In yet another aspect, detection and/or therapy can be carried out using a specially designed intravascular device that delivers excitation light to the surface of active atheromatous and/or vulnerable plaques, to photoactivate fluorescent compositions therein, and receives emitted fluorescence that is transmitted to an analysis instrument. The same device can optionally be used to deliver therapeutic light activating a similarly located photosensitizer composition when a fluorescent or nuclear signal, preferably from a beta-emitting composition, is first detected.

Additionally, the present invention provides methods for the identification of active atheromatous and/or vulnerable plaques. Methods of the present invention can advantageously differentiate stable atheromatous lesions from active atheromatous and/or vulnerable plaques. Once such a plaque is identified by methods of the present invention, further methods can be employed to stabilize the plaque against rupture while additionally reducing specific populations of cells (e.g., inflammatory cells such as macrophages and T cells) or other components (e.g., lipids and proteases) within or around the plaque, thus reducing the overall size and severity of the plaque.

In one aspect of the invention, photodynamic and/or radiolabeled compositions can be selectively targeted to inflammatory components (e.g., macrophages, T cells, lipids and proteases) within and around the active atheromatous and/or vulnerable plaque. In one embodiment, photodynamic compositions are targeted to macrophages to reduce or eliminate secretion of proteases. Reducing or eliminating protease activity greatly enhances the stability of the fibrous cap. In yet another embodiment, photodynamic compositions are targeted to T cells to reduce or eliminate secretion of factors that reduce or inhibit extracellular matrix production, such as interferon-γ. A carefully controlled application of PDT is administered to induce apoptotic cell death in the target cells. Advantageously, the parameters of PDT, including light dosimetry and amount of photodynamic compound, can be controlled to induce only apoptosis and not necrosis of the targeted cells. Inducing apoptosis rather than necrosis reduces or eliminates the inflammatory response following PDT and enhances the overall therapeutic effect.

In yet another aspect of the invention, application of PDT to the active atheromatous and/or vulnerable plaque will induce cross-linking of extracellular matrix proteins (e.g., collagen) to further stabilize the fibrous cap against rupture. Advantageously, the parameters of PDT, including the sub-cellular location of the photodynamic compounds, can be controlled to optimize clustering of the photodynamic compounds on the cell surface. Under these conditions, PDT induces cell surface cross-linking and not cell necrosis, reducing or eliminating the inflammatory response.

Other aspects of the invention are described in or are obvious from the following disclosure (and within the ambit of the invention).

BRIEF DESCRIPTION OF THE DRAWINGS

FIGS. 3A, 3B and 3C are diagrams showing a probe/catheter in accordance with an embodiment of the invention.

DETAILED DESCRIPTION

Figure 1A:
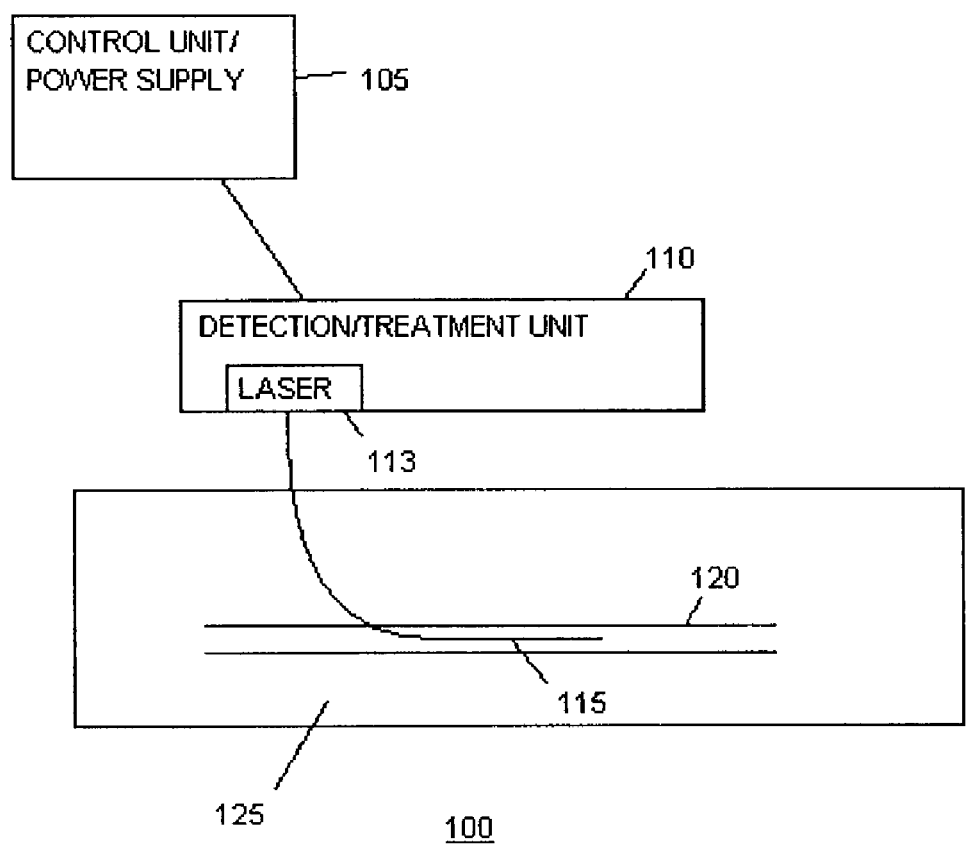
FIG. 1A illustrates a detection/treatment system for detecting and/or targeting and/or treating vulnerable plaque in accordance with an embodiment of the invention.

Methods for Detecting and Treating Vulnerable Plaque

In one aspect, the present invention relates to devices for the detection and/or therapy of active atheromatous and/or vulnerable plaques by identifying and/or activating compositions selectively targeted to the inflammatory components thereof.

An "active atheromatous plaque" comprises a plaque accumulating aggregated platlets and monocytes, such that greater than 50% stenosis is achieved. Preferably, 50% stenosis is achieved within one month of the onset of growth, more preferably 50% stenosis is achieved within six months of the onset of growth, and even more preferably 50% stenosis is achieved within one year of the onset of growth. In a preferred embodiment, the onset of active atheromatous plaque growth follows a procedure to treat atherosclerosis, such as a surgical procedure, e.g., angioplasty.

An "inactive or stable atheromatous plaque" comprises a thick fibrous cap, preferably greater than 200 microns thick, a small lipid pool or the absence thereof, which is only slowly accumulating lipids, if at all, and less than 50% stenosis. Preferably, less than 50% stenosis is maintained for one month, more preferably less than 50% stenosis is maintained for six months and even more preferably less than 50% stenosis is maintained for one year.

A "vulnerable plaque" comprises an abundance of inflammatory cells, a large lipid pool, and a thin fibrous cap. Preferably, a vulnerable plaque comprises a fibrous cap that is less than about 150 microns thick. More preferably, a vulnerable plaque comprises a fibrous cap that is less than about 100 microns thick (e.g., between about 60 and 100 microns thick). Preferably, a vulnerable plaque comprises a macrophage and/or monocyte content that is greater than about 10%. More preferably, a vulnerable plaque comprises a macrophage and/or monocyte content that is greater than about 25%. Preferably, a vulnerable plaque comprises a lipid content that is greater than about 10%. More preferably, a vulnerable plaque comprises a lipid content that is greater than about 25%.

"Inflammatory components" include inflammatory cells, lipids, procoagulants (e.g., tissue factor) and enzymes or other agents that promote inhibition of extracellular matrix production or degradation of extracellular matrix components (e.g., proteases). "Inflammatory cells" include smooth muscle cells, leukocytes, lymphocytes (B-lymphocytes and T-lymphocytes), monocytes, macrophages, foam cells, mast cells, endothelial cells, platelets, erythrocytes and polymorphonuclear cells (e.g., granulocytes and neutrophils).

As used herein, the term, "thrombus" refers to a clot of blood formed within a blood vessel from a ruptured plaque and which remains attached to its place of origin and "stenosis" refers to a constriction or decrease in vascular diameter.

In one aspect, detection of active atheromatous and/or vulnerable plaque can be carried out using a specially designed intravascular device that detects a nuclear signal, preferably from a radiolabeled composition and even more preferably from a beta-emitting composition, localized to the plaque.

As used herein, a "beta-emitting composition" comprises a beta-emitting agent, such as a radionuclide or a paramagnetic contrast agent, that emits electron or positron rays ("beta rays") and is coupled to a molecular carrier. Coupling to the carrier can be either direct or indirect (e.g., through a biotin/avidin or primary/secondary antibody association). Preferably, the beta-emitting agent is $I^{131}$, $^{18}F$-Fluorodeoxyglucose ("FDG"), $Re^{186}$, which is electron-emitting, or $Re^{188}$, which is positron-emitting. Beta-detecting devices of the present invention advantageously distinguish beta rays from gamma rays by a ratio of about 100:1 (i.e., 100:1 beta to gamma), even more preferably by a ratio of 1000:1 (i.e, 1000:1 beta to gamma). Detection of beta-emitting compositions can comprise imaging or standard means known in the art.

A "molecular carrier" refers to a biomolecule with targeting specificity for one or more components comprising the active atheromatous and/or vulnerable plaque.

In yet another aspect, detection and/or therapy can be carried out using a specially designed intravascular device that delivers excitation light to the surface of active atheromatous and/or vulnerable plaques, to photoactivate fluorescent compositions therein, and receives emitted fluorescence that is transmitted to an analysis instrument. The same device can optionally be used to deliver therapeutic light activating a similarly located photosensitizer composition when a fluorescent or nuclear signal, preferably from a beta-emitting composition, is first detected.

As used herein, a "photosensitizer" is a chemical compound, or a biological precursor thereof, that produces a phototoxic or other biological effect on biomolecules upon photoactivation. A "phototoxic species" is an amount or variety of reactive species that is sufficient to produce a phototoxic effect on a cell, cellular component or biomolecule. Preferably, the reactive species is oxygen. As used herein, a "photosensitizer composition" comprises a photosensitizer coupled to a molecular carrier. Coupling to the carrier can be either direct or indirect (e.g., through a biotin/avidin or primary/secondary antibody association).

As used herein, a "fluorescent composition" comprises a photosensitizer, fluorescent dye or photoactive dye coupled to a molecular carrier. Coupling to the carrier can be either direct or indirect (e.g., through a biotin/avidin or primary/secondary antibody association). As used herein, the term "fluorescent dye" refers to dyes that are fluorescent when illuminated with light but do not produce reactive species that are phototoxic or otherwise capable of reacting with biomolecules. A photosensitizer will fluoresce when illuminated with a certain wavelength and power of light and also produce reactive species that is phototoxic under the same or different wavelength and power of light. The term "photoactive dye," as used herein, means that the illuminated photosensitizer produces a fluorescent species, but not necessarily a reactive species in phototoxic amounts (i.e., a phototoxic species). Depending on the wavelength and power of light administered, a photosensitizer can be activated to fluoresce and, therefore, act as a photoactive dye, but not produce a phototoxic species. The wavelength and power of light can be adapted by methods known to those skilled in the art to bring about a phototoxic effect where desired.

In yet another aspect, the present invention further comprises methods to detect and/or identify active atheromatous plaques by targeting beta-emitting compositions to the inflammatory components comprising said plaques.

In one embodiment, a method of detecting an active atheromatous plaque in a subject comprises the steps of:
  a) administering a beta-emitting composition;
  b) localizing the composition to the active atheromatous plaque;
  c) detecting a signal from the beta-emitting composition; and
  d) identifying the active atheromatous plaque.

In yet another embodiment, a method of detecting a vulnerable plaque in a subject comprises the steps of:
  a) administering a beta-emitting composition;
  b) localizing the composition to the vulnerable plaque;
  c) detecting a signal from the beta-emitting composition; and
  d) identifying the vulnerable plaque.

In yet another aspect, methods of the present invention comprise a combination of detection and treatment.

In one embodiment, a method of detecting and treating an active atheromatous plaque in a subject comprises the steps of:
  a) administering a beta-emitting composition;
  b) localizing the composition to the active atheromatous plaque;
  c) detecting a signal from the beta-emitting composition; and
  d) identifying the active atheromatous plaque and administering a suitable treatment thereto.

In yet another embodiment, a method of detecting and treating a vulnerable plaque in a subject comprises the steps of:
  a) administering a beta-emitting composition;
  b) localizing the composition to the vulnerable plaque;
  c) detecting a signal from the beta-emitting composition; and
  d) identifying the vulnerable plaque and administering a suitable treatment thereto.

Suitable therapies comprise all known in the art for the treatment of active atheromatous plaque and/or vulnerable plaque, for example, treatment by statins (e.g., atorvastatin, or pravastatin), cholesterol lowering drugs, aspirin, anti-inflammatory agents, bisphosphonates, eicosapentaenoic acid, docosahexaenoic acid, ACE inhibitors (e.g., ramipril), biomolecules (e.g., thrombin-activatable fibrinolysis inhibitor, Angptl3, or Apo-A1 mimetic peptide,) clot-reducing agents (e.g., TPA), or those described in WO 01/04819 and U.S. Pat. No. 6,183,752.

In yet another aspect, methods of the present invention comprise a combination of detection and treatment, wherein treatment can comprise, for example, photodynamic therapy.

Accordingly, in one embodiment, a method of detecting and treating an active atheromatous plaque in a subject comprises the steps of:
  a) administering a detectable amount of at least one beta-emitting composition, wherein the beta-emitting composition is localized to an active atheromatous plaque;
  b) administering a therapeutically effective amount of at least one photosensitizer composition, wherein the photosensitizer composition is localized to an active atheromatous plaque;
  c) detecting a signal from the beta-emitting composition;
  d) identifying the active atheromatous plaque;
  e) light activating the photosensitizer composition at the site of the active atheromatous plaque to produce a phototoxic species; and
  f) stabilizing the active atheromatous plaque against rupture.

In yet another embodiment, a method of detecting and treating a vulnerable plaque in a subject comprises the steps of:
  a) administering a detectable amount of at least one beta-emitting composition, wherein the fluorescent composition is localized to a vulnerable plaque;
  b) administering a therapeutically effective amount of at least one photosensitizer composition, wherein the photosensitizer composition is localized to a vulnerable plaque;
  c) detecting a signal from the beta-emitting composition;
  d) identifying the vulnerable plaque;
  e) light activating the photosensitizer composition at the site of the vulnerable plaque to produce a phototoxic species; and
  f) stabilizing the vulnerable plaque against rupture.

In yet another embodiment, a method of detecting and treating an active atheromatous plaque in a subject comprises the steps of:
  a) administering a beta-emitting composition comprising a beta-emitting agent coupled to a molecular carrier; wherein the beta-emitting composition is localized to an active atheromatous plaque;
  b) administering a photosensitizer composition comprising a photosensitizer coupled to a molecular carrier; wherein the photosensitizer composition is localized to the active atheromatous plaque;
  c) detecting a signal from the beta-emitting composition;
  d) identifying the active atheromatous plaque;
  e) light activating the photosensitizer at the site of the active atheromatous plaque to produce a phototoxic species; and
  f) stabilizing the active atheromatous plaque against rupture.

In yet another embodiment, a method of detecting and treating a vulnerable plaque in a subject comprises the steps of:
  a) administering a beta-emitting composition comprising a beta-emitting agent coupled to a molecular carrier; wherein the beta-emitting composition is localized to a vulnerable plaque;

b) administering a photosensitizer composition comprising a photosensitizer agent coupled to a molecular carrier; wherein the photosensitizer is localized to the vulnerable plaque c) detecting a signal from the beta-emitting composition;

d) identifying the vulnerable plaque;

e) light activating the photosensitizer at the site of the vulnerable plaque to produce a phototoxic species; and f) stabilizing the vulnerable plaque against rupture.

In yet another embodiment, a method of detecting and treating an active atheromatous plaque in a subject comprises the steps of:

a) administering a composition comprising a beta-emitting agent and a photosensitizer coupled to a molecular carrier; wherein the composition is localized to an active atheromatous plaque;

b) detecting a signal from the beta-emitting composition;

c) identifying the active atheromatous plaque;

d) light activating the photosensitizer at the site of the active atheromatous plaque to produce a phototoxic species; and e) stabilizing the active atheromatous plaque against rupture.

In yet another embodiment, a method of detecting and treating a vulnerable plaque in a subject comprises the steps of:

a) administering a composition comprising a beta-emitting agent and a photosensitizer coupled to a molecular carrier; wherein the composition is localized to an active vulnerable plaque;

b) detecting a signal from the beta-emitting composition;

c) identifying the vulnerable plaque;

d) light activating the photosensitizer at the site of the vulnerable plaque to produce a phototoxic species; and e) stabilizing the vulnerable plaque against rupture.

In yet another embodiment, the present invention further comprises methods to identify active atheromatous and/or vulnerable plaques by targeting beta-emitting compositions to the inflammatory components comprising said plaques and employing one or more additional means to identify said plaques, including, but not limited to thermal detection, OCT, MRI or other detection modalities known in the art.

Accordingly, in one embodiment, a method of detecting an active atheromatous plaque in a subject comprises the steps of:

a) administering a beta-emitting composition;

b) localizing the composition to the active atheromatous plaque;

c) detecting a signal from the beta-emitting composition;

d) employing one or more additional means to identify said plaque; and e) identifying the active atheromatous plaque.

In yet another embodiment, a method of detecting a vulnerable plaque in a subject comprises the steps of:

a) administering a beta-emitting composition;

b) localizing the composition to the vulnerable plaque;

c) detecting a signal from the beta-emitting composition;

d) employing one or more additional means to identify said plaque; and e) identifying the vulnerable plaque.

Radiolabeled Compositions

Radiolabeled compositions of the present invention can comprise any known radioactive agents in the art, including, but not limited to radionuclide or a paramagnetic contrast agents, preferably beta-emitting agents, which are optionally coupled to molecular carriers. Examples of appropriate radionuclides for use in radiolabeling include, but are not limited to $^{131}I$, $^{125}I$, $^{123}I$, $^{99m}Tc$, $^{18}F$, $^{68}Ga$, $^{67}Ga$, $^{72}As$, $^{89}Zr$, $^{62}cu$, $^{111}cu$, $^{203}In$, $^{198}Pb$, $^{198}Hg$, $^{97}Ru$, $^{11}C$, $Re^{188}$ and $^{201}Tl$. Suitable paramagnetic contrast agents include, but are not limited to gadolinium, cobalt, nickel, manganese and iron. Preferred radionuclides or paramagnetic contrast agents are detected by gamma detecting devices of the present invention. Detection of radiolabeled compositions can comprise imaging or standard means known in the art.

Preferably, the radiolabeled composition is a beta-emitting composition, wherein the radionuclide is $^{18}F$-Fluorodeoxyglucose ("FDG"). Other beta-emitting compositions include, but are not limited to $I^{131}$, $Re^{186}$ and $Re^{188}$.

Photosensitizer Compositions

Photosensitizers of the present invention can be any known in the art, including, but not limited to, photofrin.RTM, synthetic diporphyrins and dichlorins, phthalocyanines with or without metal substituents, chloroaluminum phthalocyanine with or without varying substituents, chloroaluminum sulfonated phthalocyanine, O-substituted tetraphenyl porphyrins, 3,1-meso tetrakis (o-propionamido phenyl) porphyrin, verdins, purpurins, tin and zinc derivatives of octaethylpurpurin, etiopurpurin, hydroporphyrins, bacteriochlorins of the tetra(hydroxyphenyl) porphyrin series, chlorins, chlorin$_{e6}$, mono-l-aspartyl derivative of chlorin e6, di-l-aspartyl derivative of chlorin e6, tin(IV) chlorin$_{e6}$, meta-tetrahydroxphenylchlorin, benzoporphyrin derivatives, benzoporphyrin monoacid derivatives, tetracyanoethylene adducts of benzoporphyrin, dimethyl acetylenedicarboxylate adducts of benzoporphyrin, Diels-Adler adducts, monoacid ring "a" derivative of benzoporphyrin, sulfonated aluminum PC, sulfonated AlPc, disulfonated, tetrasulfonated derivative, sulfonated aluminum naphthalocyanines, naphthalocyanines with or without metal substituents and with or without varying substituents, zinc naphthalocyanine, anthracenediones, anthrapyrazoles, aminoanthraquinone, phenoxazine dyes, phenothiazine derivatives, chalcogenapyrylium dyes, cationic selena and tellurapyrylium derivatives, ring-substituted cationic PC, pheophorbide derivative, pheophorbide alpha and ether or ester derivatives, pyropheophorbides and ether or ester derivatives, naturally occurring porphyrins, hematoporphyrin, hematoporphyrin derivatives, hematoporphyrin esters or ethers, protoporphyrin, ALA-induced protoporphyrin IX, endogenous metabolic precursors, 5-aminolevulinic acid benzonaphthoporphyrazines, cationic imminium salts, tetracyclines, lutetium texaphyrin, tin-etio-purpurin, porphycenes, benzophenothiazinium, pentaphyrins, texaphyrins and hexaphyrins, 5-amino levulinic acid, hypericin, pseudohypericin, hypocrellin, terthiophenes, azaporphyrins, azachlorins, rose bengal, phloxine B, erythrosine, iodinated or brominated derivatives of fluorescein, merocyanines, nile blue derivatives, pheophytin and chlorophyll derivatives, bacteriochlorin and bacteriochlorophyll derivatives, porphocyanines, benzochlorins and oxobenzochlorins, sapphyrins, oxasapphyrins, cercosporins and related fungal metabolites and combinations thereof, as well as cationic and/or lipophilic formulations thereof. Several photosensitizers known in the art are FDA approved and commercially available.

Several photosensitizers known in the art are FDA approved and commercially available. In a preferred embodiment, the photosensitizer is a benzoporphyrin derivative ("BPD"), such as BPD-MA, also commercially known as BPD Verteporfin or "BPD" (available from QLT). U.S. Pat. No. 4,883,790 describes BPD compositions. BPD is a second-generation compound, which lacks the prolonged cutaneous phototoxicity of Photofrin® (Levy (1994) Semin Oncol 21: 4-10). BPD has been thoroughly characterized (Richter et al., (1987) JNCI 79:1327-1331), (Aveline et al. (1994) Photochem Photobiol 59:328-35), and it has been found to be a highly potent photosensitizer for PDT. BPD tends to accumulate within atheromatous plaques. Targeting BPD the inflammatory cells comprising vulnerable plaques according to methods of the present invention will increase the specificity of photoactivation.

Photosensitizers known as texaphyrins also tend to accumulate within atherosclerotic plaques. Targeting texaphyrins to the inflammatory cells comprising vulnerable plaques according to methods of the present invention will increase the specificity of photoactivation. In a preferred embodiment, the photosensitizer is a texaphyrin photosensitizer, such as motexafin lutetium, commercially known as Antrin (available from Pharmacyclics, Hayse et al., (2001) Cardiovasc. Res., 2:449-55).

In a preferred embodiment, the photosensitizer is tin ethyl etiopurpurin, commercially known as purlytin (available from Miravant).

Fluorescent Compositions

Fluorescent compositions of the present invention can be any known in the art, including photosensitizers, fluorescent dyes, and photoactive dyes.

The photosensitizers used for detection of vulnerable plaques can be any known in the art, as previously described. For example, hematoporphyrin derivatives have been used as fluorescent probes to investigate the development of human atherosclerotic plaques (Spokojny (1986) J. Am. Coll. Cardiol. 8:1387-1392). Hematoporphyrin derivatives can be used for the detection of vulnerable plaques, particularly plaques with extensive angiogenesis (i.e., new vasa vasorum are leaky, which will prompt accumulation of the hematoporphyrin in the plaque in addition to the selective targeting provided by the molecular carrier).

Fluorescent dyes of the present invention can be any known in the art, including, but not limited to 6-carboxy-4',5'-dichloro-2',7'-dimethoxyfluorescein succinimidyl ester; 5-(and-6)carboxyeosin; 5-carboxyfluorescein; 6-carboxyfluorescein; 5-(and-6)-carboxyfluorescein; 5-carboxyfluorescein-bis-(5-carboxymethoxy-2-nitrobenzyl) ether, -alanine-carboxamide, or succinimidyl ester; 5-carboxyfluorescein succinimidyl ester; 6-carboxyfluorescein succinimidyl ester; 5-(and-6)-carboxyfluorescein succinimidyl ester; 5-(4,6-dichlorotriazinyl) aminofluorescein; 2',7'-difluorofluorescein; eosin-5-isothiocyanate; erythrosin-5-isothiocyanate; 6-(fluorescein-5-carboxamido) hexanoic acid or succinimidyl ester; 6-(fluorescein-5-(and-6)carboxamido) hexanoic acid or succinimidyl ester; fluorescein-5-EX succinimidyl ester; fluorescein-5-isothiocyanate; fluorescein-6-isothiocyanate; Oregon Green® 488 carboxylic acid, or succinimidyl ester; Oregon Green® 488 isothiocyanate; Oregon Green® 488-X succinimidyl ester; Oregon Green® 500 carboxylic acid; Oregon Green® 500 carboxylic acid, succinimidyl ester or triethylammonium salt; Oregon Green® 514 carboxylic acid; Oregon Green® 514 carboxylic acid or succinimidyl ester; Rhodamine Green™ carboxylic acid, succinimidyl ester or hydrochloride; Rhodamine Green™ carboxylic acid, trifluoroacetamide or succinimidyl ester; Rhodamine Green™-X succinimidyl ester or hydrochloride; Rhodol Green™ carboxylic acid, N,O-bis-(trifluoroacetyl) or succinimidyl ester; bis-(4-carboxypiperidinyl) sulfonerhodamine or di(succinimidyl ester); 5-(and-6)-carboxynaphthofluorescein, 5-(and-6)-carboxynaphthofluorescein succinimidyl ester; 5-carboxyrhodamine 6G hydrochloride; 6-carboxyrhodamine 6G hydrochloride, 5-carboxyrhodamine 6G succinimidyl ester; 6-carboxyrhodamine 6G succinimidyl ester; 5-(and-6)-carboxyrhodamine 6G succinimidyl ester; 5-carboxy-2',4',5',7'-tetrabromosulfonefluorescein succinimidyl ester or bis (diisopropylethylammonium) salt; 5-carboxytetramethylrhodamine; 6-carboxytetramethylrhodamine; 5-(and-6)-carboxytetramethylrhodamine; 5-carboxytetramethylrhodamine succinimidyl ester; 6-carboxytetramethylrhodamine succinimidyl ester; 5-(and-6)-carboxytetramethylrhodamine succinimidyl ester; 6-carboxy-X-rhodamine; 5-carboxy-X-rhodamine succinimidyl ester; 6-carboxy-X-rhodamine succinimidyl ester; 5-(and-6)carboxy-X-rhodamine succinimidyl ester; 5-carboxy-X-rhodamine triethylammonium salt; Lissamine™ rhodamine B sulfonyl chloride; malachite green isothiocyanate; NANOGOLD® mono(sulfosuccinimidyl ester); QSY® 21 carboxylic acid or succinimidyl ester; QSY® 7 carboxylic acid or succinimidyl ester; Rhodamine Red™-X succinimidyl ester; 6-(tetramethylrhodamine-5-(and-6)-carboxamido)hexanoic acid succinimidyl ester; tetramethylrhodamine-5-isothiocyanate; tetramethylrhodamine-6-isothiocyanate; tetramethylrhodamine-5-(and-6)-isothiocyanate; Texas Red® sulfonyl; Texas Red® sulfonyl chloride; Texas Red®-X STP ester or sodium salt; Texas Red®-X succinimidyl ester; Texas Red®-X succinimidyl ester; and X-rhodamine-5-(and-6)-isothiocyanate.

Fluorescent dyes of the present invention can be, for example, bodipy dyes commercially available from Molecular Probes, including, but not limited to BODIPY® FL; BODIPY® TMR STP ester; BODIPY® TR-X STP ester; BODIPY® 630/650-X STP ester; BODIPY® 650/665-X STP ester; 6-dibromo-4,4-difluoro-5,7-dimethyl-4-bora-3a,4a-diaza-sindacene-3-propionic acid succinimidyl ester; 4,4-difluoro-4-bora-3a,4a-diaza-s-indacene-3,5-dipropionic acid; 4,4-difluoro-5,7-dimethyl-4-bora-3a,4a-diaza-s-indacene-3-pentanoic acid; 4,4-difluoro-5,7-dimethyl-4-bora-3a,4a-diaza-s-indacene-3-pentanoic acid succinimidyl ester; 4,4-difluoro-5,7-dimethyl-4-bora-3a,4a-diaza-s-indacene-3-propionic acid; 4,4-difluoro-5,7-dimethyl-4-bora-3a,4a-diaza-s-indacene-3-propionic acid succinimidyl ester; 4,4-difluoro-5,7-dimethyl-4-bora-3a,4a-diaza-s-indacene-3-propionic acid sulfosuccinimidyl ester or sodium salt; 6-((4,4-difluoro-5,7-dimethyl-4-bora-3a,4a-diaza-sindacene-3-propionyl)amino)hexanoic acid; 6-((4,4-difluoro-5,7-dimethyl-4-bora-3a,4a-diaza-s-indacene-3-propionyl) amino)hexanoic acid or succinimidyl ester; N-(4,4-difluoro-5,7-dimethyl-4-bora-3a,4a-diaza-s-indacene-3-propionyl) cysteic acid, succinimidyl ester or triethylammonium salt; 6-4,4-difluoro-1,3-dimethyl-5-(4-methoxyphenyl)-4-bora-3a,4a 4,4difluoro-5,7-diphenyl-4-bora-3a,4a-diaza-s-indacene-3-propionic acid; 4,4-difluoro-5,7-diphenyl-4-bora-3a,4a-diaza-s-indacene-3-propionic acid succinimidyl ester; 4,4-difluoro-5-phenyl-4-bora-3a,4a-diaza-s-indacene-3-propionic acid succinimidyl ester; 6-((4,4-difluoro-5-phenyl-4-bora-3a,4a-diaza-s-indacene-3-propionyl)amino)hexanoic acid or succinimidyl ester; 4,4-difluoro-5-(4-phenyl-1,3-butadienyl)-4-bora-3a,4a-diaza-s-indacene-3-propionic acid succinimidyl ester; 4,4-difluoro-5-(2-pyrrolyl)-4-bora-3a, 4a-diaza-s-indacene-3-propionic acid succinimidyl ester; 6-(((4,4-difluoro-5-(2-pyrrolyl)-4-bora-3a,4a-diaza-s-indacene-3-yl)styryloxy)acetyl)aminohexanoic acid or succinimidyl ester; 4,4-difluoro-5-styryl-4-bora3a,4a-diaza-s-indacene-3-propionic acid; 4,4-difluoro-5-styryl-4-bora-3a, 4a-diaza-s-indacene-3-propionic acid succinimidyl ester;

4,4-difluoro-1,3,5,7-tetramethyl-4-bora-3a,4a-diaza-sindacene-8-propionic acid; 4,4-difluoro-1,3,5,7-tetramethyl-4-bora-3a,4a-diaza-s-indacene-8-propionic acid succinimidyl ester; 4,4-difluoro-5-(2-thienyl)-4-bora-3a,4a-diaza-s-indacene-3-propionic acid succinimidyl ester; 6-(((4-(4,4-difluoro-5-(2-thienyl)-4-bora-3a,4a-diaza sindacene-3-yl)phenoxy)acetyl) amino)hexanoic acid or succinimidyl ester; and 6-(((4,4-difluoro-5-(2-thienyl)-4-bora-3a,4a-diaza-s-indacene-3-yl)styryloxy)acetyl)aminohexanoic acid or succinimidyl ester.

Fluorescent dyes the present invention can be, for example, alexa fluor dyes commercially available from Molecular Probes, including but not limited to Alexa Fluor® 350 carboxylic acid; Alexa Fluor® 430 carboxylic acid; Alexa Fluor® 488 carboxylic acid; Alexa Fluor® 532 carboxylic acid; Alexa Fluor® 546 carboxylic acid; Alexa Fluor® 555 carboxylic acid; Alexa Fluor® 568 carboxylic acid; Alexa Fluor® 594 carboxylic acid; Alexa Fluor® 633 carboxylic acid; Alexa Fluor® 647 carboxylic acid; Alexa Fluor® 660 carboxylic acid; and Alexa Fluor® 680 carboxylic acid.

Fluorescent dyes the present invention can be, for example, cy dyes commercially available from Amersham-Pharmacia Biotech, including, but not limited to Cy3 NHS ester; Cy 5 NHS ester; Cy5.5 NHS ester; and Cy 7 NHS ester.

Photoactive dyes of the present invention can be any photosensitizer known in the art which will fluoresce but not necessarily produce a reactive species in phototoxic amounts when illuminated. Depending on the wavelength and power of light administered, a photosensitizer can be activated to fluoresce and, therefore, act as a photoactive dye, but not produce a phototoxic effect unless, in some cases, the wavelength and power of light is suitably adapted to induce a phototoxic effect.

Targeting Compositions

Selectivity for target tissues of the present invention is achieved by using covalent conjugates or non-covalent complexes between molecular carriers with targeting specificity for one or more components comprising the active atheromatous and/or vulnerable plaque. Accordingly, targeting compositions of the present invention comprise one or more photosensitizers, radiolabels, and combinations thereof, "coupled" to molecular carriers. (Hasan, T. (1992) In: B. Henderson and T. Dougherty (eds.), Photodynamic Therapy: Basic Principles and Clinical Applications pp.187-200: Marcel Dekker). Use of molecular carriers advantageously allows, for example, the photosensitizer to be selected according to optical and photophysical properties, without relying on the molecular structure of the photosensitizer to provide a tissue-targeting effect.

Generally, molecular targeting is based on two facets of molecular structure. Firstly features of the molecular carriers such as size, charge, hydrophobicity and biodegradability can be manipulated to increase accumulation or retention in the plaque, and, secondly, the molecular carrier can be designed to recognize antigens, receptors or other cell type specific structures present on inflammatory cells. In a preferred embodiment, the molecular carrier is selected from the group consisting of serum proteins including receptor ligands (Hamblin et al. (1994) J. Photochem. Photobiol. 26:147-157; Hamblin and Newman (1994) J. Photochem. Photobiol. 26:45-56), microspheres (Bachor et al. (1991) Proc. Natl. Acad. Sci. U.S.A. 88:1580-1584), liposomes (Polo et al. (1996) Cancer Lett. 109:57-61), polymers (Hamblin et al. (1999) Br. J. Cancer 81:261-268), monoclonal antibodies (Hamblin et al. (2000) Br. J. Cancer 83:1544-1551), growth factors (Gijsens and De Witte (1998) Int. J. Oncol. 13:1171-1177), peptides (Krinick, (1994) J. Biomater. Sci. Polym. Ed. 5: 303-324), hormones (Akhlynina et al. (1995) Cancer Res. 55:1014-1019) and lipoproteins (Schmidt-Erfurth et al. (1997) Br. J. Cancer 75:54-61).

In a preferred embodiment, targeting compositions of the present invention are coupled to molecular carriers comprising ligands that bind to "scavenger receptors." Scavenger receptors are membrane proteins expressed on the surface of macrophages, monocytes, endothelial cells and smooth muscle cells that recognize a wide range of ligands, both naturally occurring and synthetic (Freeman et al. (1997) Curr. Opin. Hematol. 4:41-47). Presently, there are six members of the scavenger receptor family belonging to three classes (e.g., class A, B or C). After initial binding to the scavenger receptor, the ligands are rapidly internalized and are routed to lysosomes for degradation by proteases and other lysosomal enzymes. The wide and diverse range of structures recognized by these receptors has led to them being termed "molecular flypaper" (Krieger et al. (1992) Trends Biochem. Sci. 17:141-146, 1992). The ligands are all molecules with a pronounced anionic charge that have some common conformational features (Haberland and Fogelman (1985) Proc. Natl. Acad. Sci. U.S.A. 82:2693-2697; Takata (1989) Biochem. Biophys. Acta. 984:273-280). Specific targeting of compositions to J774 and other macrophage-like cells in vitro has been achieved with conjugates of maleylated albumin, daunorubicin and doxorubicin (Mukhopadhyay et al (1992) Biochem J. 284:237-241; Basu et al. (1994) FEBS Lett. 342: 249-254; Hamblin et al. (2000) Photochem Photobiol. 4:533-540).

Numerous scavenger receptor ligands known in the art (either with or without polyethyl glycolization) can be used to localize targeting compositions of the present invention to active atheromatous and/or vulnerable plaques, including, but not limited to maleylated albumin, oxidized low density lipoprotein, acetylated low density lipoprotein, oxidized high density lipoprotein, malondialdehyde treated proteins, lipotechoic acid, formaldehyde treated albumin, glycated albumin, polyinosinic acid, glycated lipoproteins, dextran sulfate, anionic phospholipids (phosphatidyl serine), fucoidin, carrageenan, polyvinyl sulfate, monoclonal antibodies that recognize CD11b or c, CD13, CD14, CD16a, CD32 or CD68.

In a preferred embodiment, targeting compositions of the present invention are coupled to molecular carriers that target macrophages and/or monocytes of active atheromatous and/or vulnerable plaques. These molecular carriers can be targeted to, for example, tenascin C, tissue factor, tissue inhibitor of MMP 1 and 2, oxidized LDL receptor (also known in the art as CD36), heme oxygenase-1, human cartilage gp-39, IL-6, IL-6 receptor, IL-10, IL-10 receptor, lectin-like oxidized LDL-receptor ("LOX-1"), bacterial chemotactic peptide receptor agonists, preferably For—Met—Leu—Phe ("F-MLK"), macrophage chemoattractant protein-1 receptor ("CCR-9") and monocyte inflammatory protein-1 and receptors thereof (including "CCR-5"). Such molecular carriers can be, for example, antibodies against these biomolecules, ligands binding the same or analogs thereof.

In a preferred embodiment, targeting compositions of the present invention are coupled to molecular carriers that target T cells of active atheromatous and/or vulnerable plaques. These molecular carriers can be targeted to, for example, IL-10, IL-10 receptor, monocyte inflammatory protein-1 and receptors thereof and transferrin. Such molecular carriers can be, for example, antibodies against these biomolecules, ligands binding the same or analogs thereof, including, but not limited to monoclonal antibodies that recognize CD1, CD2, CD3, CD4, CD5, CD6, CD7, CD8, CD25, CD28, CD44, CD71 or transferrin.

In a preferred embodiment, targeting compositions of the present invention are delivered via molecular carriers that target the lipid pool of the atheroma, including but not limited to hydrophobic photosensitizers or photosensitizers delivered in hydrophobic vehicles such as liposomes (with positive, neutral or negatively charged and optionally containing cholesterol or cardiolipin) cremaphor EL, PEG/solvent mixtures, iodized castor oil, and various nanoparticles and micellar preparations.

In a preferred embodiment, targeting compositions of the present invention are coupled to molecular carriers that target proteases that degrade extracellular matrix (e.g., metalloproteinases), including but not limited to monoclonal antibodies against the protease and proteinase substrates.

In a preferred embodiment, targeting compositions of the present invention are coupled to molecular carriers that target the endothelial cells of active atheromatous and/or vulnerable plaques. These molecular carriers can be targeted to, for example, endothelial adhesion molecules including, but not limited to, ICAM (also known in the art as CD54) and VCAM (also known in the art as CD106), angiotensin II, angiotensin converting enzyme (also known in the art as CD143), endothelial derived lipase, tissue factor, heme oxygenase-1, LOX-1, low density lipoprotein ("LDL"), high density lipoprotein, ("HDL"), P-selectin, L-selectin and E-selectin. Such molecular carriers can be, for example, antibodies against these biomolecules, ligands binding the same or analogs thereof. Targeting compositions of the present invention can be coupled to molecular carriers that target the subendothelial matrix of active atheromatous and/or vulnerable plaques.

In a preferred embodiment, targeting compositions of the present invention are coupled to molecular carriers that target neutrophils of active atheromatous and/or vulnerable plaques. These molecular carriers can be targeted to, for example, myeloperoxidase. Such molecular carriers can be, for example, antibodies against these biomolecules, ligands binding the same or analogs thereof.

In a preferred embodiment, targeting compositions of the present invention are coupled to molecular carriers that target B cells of active atheromatous and/or vulnerable plaques. These molecular carriers can be targeted to, for example, IL-6, IL-6 receptor, IL-10 and IL-10 receptor. Such molecular carriers can be, for example, antibodies against these biomolecules, ligands binding the same or analogs thereof.

In a preferred embodiment, targeting compositions of the present invention are coupled to molecular carriers that target smooth muscle cells of active atheromatous and/or vulnerable plaques. These molecular carriers can be targeted to, for example, LOX-1. Such molecular carriers can be, for example, antibodies against these biomolecules, ligands binding the same or analogs thereof.

In a preferred embodiment, targeting compositions of the present invention are coupled to molecular carriers that either directly or indirectly associate with the target. For example, indirect targeting can be achieved by first localizing a biotinylated molecular carrier to a target, followed by administration of a streptavidin-linked composition comprising a photoactive dye, fluorescent dye, photosensitizer or radioactive agent.

The features of an active atheromatous and/or vulnerable plaque that are distinguishable from stable atheromatous plaques advantageously distinguish active atheromatous and/or vulnerable plaques from stable atheromatous plaques according to methods of the present invention.

An "active atheromatous plaque" comprises a plaque accumulating aggregated platlets and monocytes, such that greater than 50% stenosis is achieved. Preferably, 50% stenosis is achieved within one month of the onset of growth, more preferably 50% stenosis is achieved within six months of the onset of growth, and even more preferably 50% stenosis is achieved within one year of the onset of growth. In a preferred embodiment, the onset of active atheromatous plaque growth follows a surgical procedure, such as angioplasty.

An "inactive or stable atheromatous plaque" comprises a thick fibrous cap, preferably greater than 200 microns thick, a small lipid pool or the absence thereof, which is only slowly accumulating lipids, if at all, and less than 50% stenosis. Preferably, less than 50% stenosis is maintained for one month, more preferably less than 50% stenosis is maintained for six months and even more preferably less than 50% stenosis is maintained for one year.

Vulnerable plaques comprise an abundance of inflammatory cells, a large lipid pool, and a thin fibrous cap. Preferably, a vulnerable plaque comprises a fibrous cap that is less than about 150 microns thick. More preferably, a vulnerable plaque comprises a fibrous cap that is less than about 100 microns thick (e.g., between about 60 and 100 microns thick). Preferably, a vulnerable plaque comprises a macrophage and/or monocyte content that is greater than about 10%. More preferably, a vulnerable plaque comprises a macrophage and/or monocyte content that is greater than about 25%. Preferably, a vulnerable plaque comprises a lipid content that is greater than about 10%. More preferably, a vulnerable plaque comprises a lipid content that is greater than about 25%.

Thus, localizing a targeting composition to activated macrophages or proteases that degrade extracellular matrix via a molecular carrier, for example, confers a selective advantage on an active atheromatous and/or vulnerable plaque, such that uptake of the composition is far greater than in a stable atheromatous plaque. Moreover, where the targeting compositions comprise fluorescent compositions, photodetection or photoactivation of the vulnerable plaque can be carried out at a wavelength and power of light that has an insubstantial or negligible effect on stable atheromatous plaques. Thus, the methods and devices of the present invention are advantageously suited for detection and therapy of active atheromatous and/or vulnerable plaques and not merely commonplace stable atheromatous plaques.

The practice of the present invention employs, unless otherwise indicated, conventional techniques of molecular biology (including recombinant techniques), microbiology, cell biology, biochemistry and immunology, which are within the skill of the art. Such techniques are explained fully in the literature, such as, "Molecular Cloning: A Laboratory Manual", second edition (Sambrook, 1989); "Oligonucleotide Synthesis" (Gait, 1984); "Animal Cell Culture" (Freshney, 1987); "Methods in Enzymology" "Handbook of Experimental Immunology" (Weir, 1996); "Gene Transfer Vectors for Mammalian Cells" (Miller and Calos, 1987); "Current Protocols in Molecular Biology" (Ausubel, 1987); "PCR: The Polymerase Chain Reaction", (Mullis, 1994); "Current Protocols in Immunology" (Coligan, 1991). These techniques are applicable to the production of the polynucleotides and polypeptides of the invention, and, as such, may be considered in making and practicing the invention. Particularly useful techniques for particular embodiments will be discussed in the sections that follow.

Compositions of the present invention that are useful for detection of active atheromatous and/or vulnerable plaques of can comprise molecular carriers that are radiolabeled. For example, photosensitizer compositions of the present invention can comprise radiolabeled molecular carriers coupled to photosensitizers. A number of radiolabeled molecular carriers have been tested for their ability to bind to and permit scintigraphic detection of atherothrombotic materials. These include labeled antibodies to oxidized LDL, fibrinogen, autologous platelets, fibrin fragment E1, plasminogen activators, and 99mTc-conjugated antibodies against modified LDL (Tsimikas et al. (1999) J. Nucl. Cardiol. 6: 41-53).

Highly specific and sensitive labels are provided by radionuclides, which can then be detected using positron emission tomography (PET) or Single Photon Emission Computed Tomography (SPECT) imaging. Alternatively, devices of the present invention can be employed for intravascular detection of beta waves.

Such radiolabels may be associated with the molecular carrier by ionic association or covalent bonding directly to an atom of the carrier. The radiolabel may be non-covalently or covalently associated with the carrier through a chelating structure. A "chelating structure" refers to any molecule or complex of molecules which bind to both the label and targeting moiety. Many such chelating structures are known in the art. Chelating structures include, but are not limited to —$N_2S_2$, —$NS_3$, —$N_4$, dota derivatives [1,4,7,10-tetrakis (carboxymethyl)-1,4,7,10-tetrazacyclododecane], an isonitrile, a hydrazine, a HYNIC (hydrazinonicotinic acid), 2-methylthiolnicotinic acid, phosphorus, or a carboxylate containing group; or through an auxiliary molecule such as mannitol, gluconate, glucoheptonate, tartrate, and the like. In some cases, chelation can be achieved without including a separate chelating structure, because the radionuclide chelates directly to atom(s) in the molecular carrier, for example to oxygen atoms in vanous moieties.

The chelating structure, auxiliary molecule, or radionuclide may be placed in spatial proximity to any position of the molecular carrier which does not interfere with the interaction of the targeting molecule with its target site in cardiovascular tissue. Accordingly, the chelating structure, auxiliary molecule, or radionuclide may be covalently or non-covalently associated with any moiety of the molecular carrier (except the receptor-binding moiety where the molecular carrier is a receptor and the epitope binding region where the molecular carrier is an antibody).

Radionuclides may be placed in spatial proximity to the molecular carrier using known procedures that effect or optimize chelation, association, or attachment of the specific radionuclide to ligands. For example, when $^{123}I$ is the radionuclide, the imaging agent may be labeled in accordance with the known radioiodination procedures such as direct radioiodination with chloramine T, radioiodination exchange for a halogen or an organometallic group, and the like. When the radionuclide is $^{99m}Tc$, the imaging agent may be labeled using any method suitable for attaching $^{99m}Tc$ to a ligand molecule. Preferably, when the radionuclide is $^{99m}Tc$, an auxiliary molecule such as mannitol, gluconate, glucoheptonate, or tartrate is included in the labeling reaction mixture, with or without a chelating structure. More preferably, $^{99m}Tc$ is placed in spatial proximity to carrier by reducing $^{99m}TcO_4$, with tin in the presence of mannitol and the targeting molecule. Other reducing agents, including tin tartrate or non-tin reductants such as sodium dithionite, may also be used to make radiolabeled compositions of the present invention.

In general, labeling methodologies vary with the choice of radionuclide and the carrier to be labeled. Labeling methods are described for example in Peters et al. (1986) Lancet 2:946-949; Srivastava et al. (1984) Semin. Nucl. Med 14:68-82; Sinn et al. (1984) J. Nucl. Med. 13:180; McAfee et al. (1976) J. Nucl. Med. 17:480-487; Welch et al., (1977) J. Nucl. Med. 18:558-562; Thakuret et al. (1984) Semin. Nucl. Med. 14:107; Danpure et al. (1981) Br. J. Radiol. 54:597-601; Danpure et al. (1982) Br. J. Radiol. 55:247-249; Peters et al. (1982) J. Nucl. Med. 24:39-44; Gunter et al. (1983) Radiology 149:563-566 and Thakur et al. (1985) J. Nucl. Med. 26:518-523.

After the labeling reaction is complete, the reaction mixture may optionally be purified using one or more chromatography steps such as Sep Pack or high performance liquid chromatography (HPLC). Any suitable HPLC system may be used if a purification step is performed, and the yield of cardiovascular imaging agent obtained from the HPLC step may be optimized by varying the parameters of the HPLC system, as is known in the art. Any HPLC parameter may be varied to optimize the yield of the cardiovascular imaging agent of the invention. For example, the pH may be varied, e.g., raised to decrease the elution time of the peak corresponding to the radiolabeled carrier.

The term "coupling agent" as used herein, refers to a reagent capable of coupling a composition (e.g., photoactive dye, fluorescent dye, photosensitizer or radioactive agent) to a molecular carrier, or to a "backbone" or "bridge" moiety. Any bond which is capable of linking the components such that they are stable under physiological conditions for the time needed for administration and treatment is suitable, but covalent linkages are preferred. The link between two components may be direct, e.g., where a photosensitizer is linked directly to a molecular carrier, or indirect, e.g., where a photosensitizer is linked to an intermediate, e.g., linked to a backbone, and that intermediate being linked to the molecular carrier. A coupling agent should function under conditions of temperature, pH, salt, solvent system, and other reactants that substantially retain the chemical stability of the photosensitizer, the backbone (if present), and the molecular carrier.

A coupling agent is not always required, for example, where the fluorescent compound is in the form of a sulfonyl chloride, isothiocyanate or succinimidyl ester, no coupling agent is necessary.

A coupling agent can link components without the addition to the linked components of elements of the coupling agent. Other coupling agents result in the addition of elements of the coupling agent to the linked components. For example, coupling agents can be cross-linking agents that are homo- or hetero-bifunctional, and wherein one or more atomic components of the agent can be retained in the composition. A coupling agent that is not a cross-linking agent can be removed entirely during the coupling reaction, so that the molecular product can be composed entirely of the photosensitizer, the targeting moiety, and a backbone moiety (if present).

Many coupling agents react with an amine and a carboxylate, to form an amide, or an alcohol and.a carboxylate to form an ester. Coupling agents are known in the art, see, e.g., M. Bodansky, "Principles of Peptide Synthesis", 2nd ed., referenced herein, and T. Greene and P. Wuts, "Protective Groups in Organic Synthesis," 2nd Ed, 1991, John Wiley, N.Y. Coupling agents should link component moieties stably, but such that there is only minimal or no denaturation or deactivation of the photosensitizer or the molecular carrier.

The photosensitizer compositions of the invention can be prepared by coupling the photosensitizer to molecular carriers using methods described in the following Examples, or by methods known in the art. A variety of coupling agents, including cross-linking agents, can be used for covalent conjugation. Examples of cross-linking agents include N,N'-dicyclohexylcarbodiimide (DCC), N-succinimidyl-S-acetylthioacetate (SATA), N-succinimidyl-3-(2-pyridyldithio)

propionate (SPDP), orthophenylenedimaleimide (o-PDM), and sulfosuccinimidyl 4-(N-maleimidomethyl) cyclohexane-1-carboxylate (sulfo-SMCC) (Karpovsky et al. (1984) J. Exp. Med. 160:1686; Liu, MA et al. (1985) Proc. Natl. Acad. Sci. USA 82:8648). Other methods include those described by Paulus and Behring (1985) Ins. Mitt., 78:118-132; Brennan et al. (1985) Science 229:81-83 and Glennie et al., (1987) J. Immunol, 139:2367-2375. A large number of coupling agents for peptides and proteins, along with buffers, solvents, and methods of use, are described in the Pierce Chemical Co. catalog, pages T155-T-200, 1994 (3747 N. Meridian Rd., Rockford Ill., 61105, U.S.A.; Pierce Europe B.V., P.O. Box 1512, 3260 BA Oud Beijerland, The Netherlands), the contents of which are hereby incorporated by reference.

DCC is a useful coupling agent (Pierce #20320; Rockland, Ill.). It promotes coupling of the alcohol NHS to chlorin e6 in DMSO (Pierce #20684), forming an activated ester which can be cross-linked to polylysine. DCC (N,N'dicyclohexylcarbodiimide) is a carboxy-reactive cross-linker commonly used as a coupling agent in peptide synthesis, and has a molecular weight of 206.32. Another useful cross-linking agent is SPDP (Pierce #21557), a heterobifunctional cross-linker for use with primary amines and sulfhydryl groups. SPDP has a molecular weight of 312.4, a spacer arm length of 6.8 angstroms, is reactive to NHS-esters and pyridyldithio groups, and produces cleavable cross-linking such that, upon further reaction, the agent is eliminated so the photosensitizer can be linked directly to a backbone or molecular carrier. Other useful conjugating agents are SATA (Pierce #26102) for introduction of blocked SH groups for two-step cross-linking, which is deblocked with hydroxylamine-25-HCl (Pierce #26103), and sulfo-SMCC (Pierce #22322), reactive towards amines and sulfhydryls. Other cross-linking and coupling agents are also available from Pierce Chemical Co. (Rockford, Ill.). Additional compounds and processes, particularly those involving a Schiff base as an intermediate, for conjugation of proteins to other proteins or to other compositions, for example to reporter groups or to chelators for metal ion labeling of a protein, are disclosed in EPO 243,929 A2 (published Nov. 4, 1987 ).

Photosensitizers which contain carboxyl groups can be joined to lysine s-amino groups in the target polypeptides either by preformed reactive esters (such as N-hydroxy succinimide ester) or esters conjugated in situ by a carbodiimide-mediated reaction. The same applies to photosensitizers that contain sulfonic acid groups, which can be transformed to sulfonyl chlorides, which react with amino groups. Photosensitizers that have carboxyl groups can be joined to amino groups on the polypeptide by an in situ carbodiimide method. Photosensitizers can also be attached to hydroxyl groups, of serine or threonine residues or to sulfhydryl groups, of serine or threonine residues or to sulfhydryl groups of cysteine residues.

Methods of joining components of a composition, e.g., coupling polyamino acid chains bearing photosensitizers to antibacterial polypeptides, can use heterobifunctional cross linking reagents. These agents bind a functional group in one chain and to a different functional group in the second chain. These functional groups typically are amino, carboxyl, sulfhydryl, and aldehyde. There are many permutations of appropriate moieties that will react with these groups and with differently formulated structures, to join them together (described in the Pierce Catalog and Merrifield et al. (1994) Ciba Found Symp. 186:5-20).

The production and purification of photosensitizers coupled to molecular carriers can be practiced by methods known in the art. Yield from coupling reactions can be assessed by spectroscopy of product eluting from a chromatographic fractionation in the final step of purification. The presence of uncoupled photosensitizer and reaction products containing the photosensitizer can be followed by the physical property that the photosensitizer moiety absorbs light at a characteristic wavelength and extinction coefficient, so incorporation into products can be monitored by absorbance at that wavelength or a similar wavelength. Coupling of one or more photosensitizer molecules to a molecular carrier or to a backbone shifts the peak of absorbance in the elution profile in fractions eluted using sizing gel chromatography, e.g., with the appropriate choice of Sephadex G50, 6100, or 6200 or other such matrices (Pharmacia-Biotech, Piscataway N.J.). Choice of appropriate sizing gel, for example Sephadex gel, can be determined by that gel in which the photosensitizer elutes in a fraction beyond the excluded volume of material too large to interact with the bead, i.e., the uncoupled starting photosensitizer composition interacts to some extent with the fractionation bead and is concomitantly retarded to some extent. The correct useful gel can be predicted from the molecular weight of the uncoupled photosensitizer. The successful reaction products of photosensitizer compositions coupled to additional moieties generally have characteristic higher molecular weights, causing them to interact with the chromatographic bead to a lesser extent, and thus appear in fractions eluting earlier than fractions containing the uncoupled photosensitizer substrate. Unreacted photosensitizer substrate generally appears in fractions characteristic of the starting material, and the yield from each reaction can thus be assessed both from size of the peak of larger molecular weight material, and the decrease in the peak of characteristic starting material. The area under the peak of the product fractions is converted to the size of the yield using the molar extinction coefficient.

The product can be analyzed using NMR, integrating areas of appropriate product peaks, to determine relative yields with different coupling agents. A red shift in absorption of a photosensitizer has often been observed following coupling to a polyamino acid. Coupling to a larger carrier such as a protein might produce a comparable shift, as coupling to an antibody resulted in a shift of about 3-5 nm in that direction compared to absorption of the free photosensitizer. Relevant absorption maxima and extinction coefficients in 0.1M NaOH/1% SDS are, for chlorin$_{e6}$, 400 nm and 150,000 $M^{-1}$, $cm^{-1}$, and for benzoporphyrin derivative, 430 nm and 61,000 $M^{-1}$, $cm^{-1}$.

Photosensitizers compositions of the invention include those in which a photosensitizer is coupled directly to a molecular carrier, such as a scavenger receptor ligand. Other photosensitizer compositions of the invention include a "backbone" or "bridge" moiety, such as a polyamino acid, in which the backbone is coupled both to a photosensitizer and to a molecular carrier.

Inclusion of a backbone in a composition with a photosensitizer and a molecular carrier can provide a number of advantages, including the provision of greater stoichiometric ranges of photosensitizer and molecular carriers coupled per backbone. If the backbone possesses intrinsic affinity for a target organism, the affinity of the composition can be enhanced by coupling to the backbone. The specific range of organisms that can be targeted with one composition can be expanded by coupling two or more different molecular carriers to a single photosensitizer-backbone composition.

Peptides useful in the methods and compounds of the invention for design and characterization of backbone moieties include poly-amino acids which can be homo- and hetero-polymers of L-, D-, racemic DL- or mixed L- and D-amino acid composition, and which can be of defined or random mixed composition and sequence. These peptides can be modeled after particular natural peptides, and optimized by the technique of phage display and selection for enhanced binding to a chosen target, so that the selected peptide of highest affinity is characterized and then produced synthetically. Further modifications of functional groups can be introduced for purposes, for example, of increased solubility, decreased aggregation, and altered extent of hydrophobicity. Examples of nonpeptide backbones include nucleic acids and derivatives of nucleic acids such as DNA, RNA and peptide nucleic acids; polysaccharides and derivatives such as starch, pectin, chitins, celluloses and hemimethylated celluloses; lipids such as triglyceride derivatives and cerebrosides; synthetic polymers such as polyethylene glycols (PEGS) and PEG star polymers; dextran derivatives, polyvinyl alcohols, N-(2-hydroxypropyl)-methacrylamide copolymers, poly (DL-glycolic acid-lactic acid); and compositions containing elements of any of these classes of compounds.

The affinity of a photosensitizer composition can be refined by modifying the charge of a component of the composition. Conjugates such as poly-L-lysine chlorin$_{e6}$ can be made in varying sizes and charges (cationic, neutral, and anionic), for example, free NH2 groups of the polylysine are capped with acetyl, succinyl, or other R groups to alter the charge of the final composition. Net charge of a composition of the present invention can be determined by isoelectric focusing (IEF). This technique uses applied voltage to generate a pH gradient in a non-sieving acrylamide or agarose gel by the use of a system of ampholytes (synthetic buffering components). When charged polypeptides are applied to the gel they will migrate either to higher pH or to lower pH regions of the gel according to the position at which they become non-charged and hence unable to move further. This position can be determined by reference to the positions of a series of known IEF marker proteins.

Photosensitizer compositions of the present invention can comprise photosensitizers coupled to antibodies, which are known in the art as "photoimmunoconjugates." The antibody component of the photoimmunoconjugate can bind with specificity to an epitope present on the surface of a cell comprising the vulnerable plaque. As used herein, the term "binding with specificity" means that cells that do not express the epitope are only poorly recognized by the antibody.

The term "antibody" as used in this invention includes intact molecules as well as fragments thereof, such as Fab and Fab', which are capable of binding the epitopic determinant. Fab fragments retain an entire light chain, as well as one-half of a heavy chain, with both chains covalently linked by the carboxy terminal disulfide bond. Fab fragments are monovalent with respect to the antigen-binding site. The antibodies of the invention comprise whole native antibodies, bispecific antibodies; chimeric antibodies; Fab, Fab', single chain variable region fragments (scFv) and fusion polypeptides. Preferably, the antibodies of the invention are monoclonal.

The antibodies of this invention can be prepared in several ways. Methods of producing and isolating whole native antibodies, bispecific antibodies; chimeric antibodies; Fab, Fab', single chain V region fragments (scFv) and fusion polypeptides are known in the art. See, for example, Harlow and Lane (1988) *Antibodies: A Laboratory Manual*, Cold Spring Harbor Laboratory, New York (Harlow and Lane, 1988).

Antibodies are most conveniently obtained from hybridoma cells engineered to express an antibody. Methods of making hybridomas are well known in the art. The hybridoma cells can be cultured in a suitable medium, and spent medium can be used as an antibody source. Polynucleotides encoding the antibody can in turn be obtained from the hybridoma that produces the antibody, and then the antibody may be produced synthetically or recombinantly from these DNA sequences. For the production of large amounts of antibody, it is generally more convenient to obtain an ascites fluid. The method of raising ascites generally comprises injecting hybridoma cells into an immunologically naive histocompatible or immunotolerant mammal, especially a mouse. The mammal may be primed for ascites production by prior administration of a suitable composition, e.g., Pristane.

Another method of obtaining antibodies is to immunize suitable host animals with an antigen and to follow standard procedures for polyclonal or monoclonal production. Monoclonal antibodies (Mabs) thus produced can be "humanized" by methods known in the art. Examples of humanized antibodies are provided, for instance, in U.S. Pat. Nos. 5,530,101 and 5,585,089.

"Humanized" antibodies are antibodies in which at least part of the sequence has been altered from its initial form to render it more like human immunoglobulins. In one version, the heavy chain and light chain C regions are replaced with human sequence. In another version, the CDR regions comprise amino acid sequences for recognition of antigen of interest, while the variable framework regions have also been converted to human sequences. See, for example, EP 0329400. In a third version, variable regions are humanized by designing consensus sequences of human and mouse variable regions, and converting residues outside the CDRs that are different between the consensus sequences. The invention encompasses humanized Mabs.

The invention also encompasses hybrid antibodies, in which one pair of heavy and light chains is obtained from a first antibody, while the other pair of heavy and light chains is obtained from a different second antibody. Such hybrids may also be formed using humanized heavy and light chains.

Construction of phage display libraries for expression of antibodies, particularly the Fab or scFv portion of antibodies, is well known in the art (Heitner et al. (2001) J Immunol Methods 248:17-30). The phage display antibody libraries that express antibodies can be prepared according to the methods described in U.S. Pat. No. 5,223,409 incorporated herein by reference. Procedures of the general methodology can be adapted using the present disclosure to produce antibodies of the present invention. The method for producing a human monoclonal antibody generally involves (1) preparing separate heavy and light chain-encoding gene libraries in cloning vectors using human immunoglobulin genes as a source for the libraries, (2) combining the heavy and light chain encoding gene libraries into a single dicistronic expression vector capable of expressing and assembling a heterodimeric antibody molecule, (3) expressing the assembled heterodimeric antibody molecule on the surface of a filamentous phage particle, (4) isolating the surface-expressed phage particle using immunoaffinity techniques such as panning of phage particles against a preselected antigen, thereby isolating one or more species of phagemid containing particular heavy and light chain-encoding genes and antibody molecules that immunoreact with the preselected antigen.

Single chain variable region fragments are made by linking light and heavy chain variable regions by using a short linking peptide. Any peptide having sufficient flexibility and length can be used as a linker in a scFv. Usually the linker is selected to have little to no immunogenicity. An example of a linking peptide is (GGGGS)$_3$, which bridges approximately 3.5 nm between the carboxy terminus of one variable region and the amino terminus of another variable region. Other linker sequences can also be used. All or any portion of the heavy or light chain can be used in any combination. Typically, the entire variable regions are included in the scFv. For instance, the light chain variable region can be linked to the heavy chain variable region. Alternatively, a portion of the light chain variable region can be linked to the heavy chain variable region, or a portion thereof. Also contemplated are compositions comprising a biphasic scFv in which one component is a polypeptide that recognizes an antigen and another component is a different polypeptide that recognizes a different antigen, such as a T cell epitope.

ScFvs can be produced either recombinantly or synthetically. For synthetic production of scFv, an automated synthesizer can be used. For recombinant production of scFv, a suitable plasmid containing a polynucleotide that encodes the scFv can be introduced into a suitable host cell, either eukaryotic, such as yeast, plant, insect or mammalian cells, or prokaryotic, such as *Escherichia coli*, and the protein expressed by the polynucleotide can be isolated using standard protein purification techniques.

A particularly useful system for the production of scFvs is plasmid pET-22b(+) (Novagen, Madison, Wis.) in *E. coli*. pET-22b(+) contains a nickel ion binding domain consisting of 6 sequential histidine residues, which allows the expressed protein to be purified on a suitable affinity resin. Another example of a suitable vector is pcDNA3 (Invitrogen, San Diego, Calif.), described above.

Expression conditions should ensure that the scFv assumes functional and, preferably, optimal tertiary structure. Depending on the plasmid used (especially the activity of the promoter) and the host cell, it may be necessary or useful to modulate the rate of production. For instance, use of a weaker promoter, or expression at lower temperatures, may be necessary or useful to optimize production of properly folded scFv in prokaryotic systems; or, it may be preferable to express scFv in eukaryotic cells. Antibody purification methods may include salt precipitation (for example, with ammonium sulfate), ion exchange chromatography (for example, on a cationic or anionic exchange column run at neutral pH and eluted with step gradients of increasing ionic strength), gel filtration chromatography (including gel filtration HPLC), and chromatography on affinity resins such as protein A, protein G, hydroxyapatite, and anti-immunoglobulin.

Photosensitizers can be linked to antibodies according to any method known in the art. For example, the antibody can be directly linked to the photosensitizer through a polymer or a polypeptide linkage. Polymers of interest include, but are not limited to polyamines, polyethers, polyamine alcohols, derivitized to components by means of ketones, acids, aldehydes, isocyanates or a variety of other groups. Polypeptide linkages can comprise, for example polyL-lysine linkages (Del Govematore et al.(2000) Br. J. Cancer 82:56-64; Hamblin et al. (2000) Br. J. Cancer 83:1544-41; Molpus et al. (2000) Gynecol Oncol 76:397-404). The antibody can be linked to a photosensitizer and at least one solubilizing agent each of which are independently bound to the antibody through a direct covalent linkage. The direct covalent linkage can be, for example, an amide linkage to a lysine residue of the antibody, as described in U.S. application serial No. 10/137,029, the contents of which are herein incorporated by reference.

Photosensitizer compositions of the present invention can comprise photosensitizers linked to molecular carriers comprising the sequences of naturally occurring proteins and peptides, from variants or fragments of these peptides, and from biologically or chemically synthesized peptides or peptide fragments. Naturally occurring peptides which have affinity for one or more target cells can provide sequences from which additional peptides with desired properties, e.g., increased affinity or specificity, can be synthesized individually or as members of a library of related peptides. Such peptides can be selected on the basis of affinity for the target cell.

The term "or (a) fragment(s) thereof" as employed in the present invention and in context with polypeptides of the invention, comprises specific peptides, amino acid stretches of the polypeptides as disclosed herein. It is preferred that said "fragment(s) thereof" is/are functional fragment(s). The term "functional fragment" denotes a part of the above identified polypeptide of the invention which fulfills, at least in part, physiologically and/or structurally related activities of the polypeptide of the invention. The polypeptides of the present invention can be recombinant polypeptides expressed in eukaryotic cells, like mammalian cells.

Generally, recombinant DNA technology has enabled the expression of foreign (heterologous) proteins in cell lines of choice. In this process, a vector containing genetic material directing a cell to produce a protein encoded by a portion of a heterologous DNA sequence is introduced into the host, and the transformed host cells can be fermented, cultured or otherwise subjected to conditions which facilitate the expression of the heterologous DNA, leading to the formation of large quantities of the desired protein. Plasmids are extensively used as vectors to clone DNA molecules. Most plasmid vectors are made by taking DNA from a variety of replicons (plasmids, bacteriophage chromosomes and bacterial chromosomes) and joining the DNA together (using restriction enzymes and DNA ligase) to form a plasmid that has an origin of replication, a selection marker (usually an antibiotic-resistance gene) and a promoter for expressing genes of interest in the required host cell. A vector can be, for example, as in U.S. Pat. Nos. 5,990,091 and 6,004,777, and as in PCT/US00/04203. Methods for generation and use of recombinant vectors in vitro are well known in the art. See Sambrook, Fritsch and Maniatis, Molecular Cloning, A Laboratory Manual, 2nd Ed., Cold Spring Harbor Laboratory Press, 1989 (e.g., procedures for isolating DNA, constructing recombinant vectors, transfecting and transforming cells and producing heterologous peptides).

Furthermore, the recombinant vector can, in addition to the nucleic acid sequences of the invention (e.g., those encoding the targeting peptide or functional fragments thereof), comprise expression control elements, allowing proper expression of the coding regions in suitable hosts. Such control elements are known in the art and can include a promoter, a splice cassette, translation initiation codon, translation and insertion site for introducing an insert into the vector. Preferably, the nucleic acid molecule is operatively linked to expression control sequences allowing expression in eukaryotic or prokaryotic cells.

Control elements ensuring expression in eukaryotic and prokaryotic cells are well known to those skilled in the art. As mentioned herein above, they usually comprise regulatory sequences ensuring initiation of transcription and optionally poly-A signals ensuring termination of transcription and stabilization of the transcript. Additional regulatory elements can include transcriptional as well as translational enhancers, and/or naturally-associated or heterologous promoter regions. Possible regulatory elements permitting expression in for example mammalian cells comprise the CMV-HSV thymikine kinase promoter, SV40, RSV-promoter (Rous sarcoma virus), human elongation factor 1α-promoter, aPM-I promoter (Schaffer et al. (1999) Biochem. Biophys. Res. Commun. 260:416-425), or inducible promoter(s), like, metallothionein or tetracyclin, or enhancers, like CMV enhancer or SV40-enhancer. For the expression in prokaryotic cells, a multitude of promoters including, for example, the tac-lac-promoter or the trp promoter, has been described. Besides elements that are responsible for the initiation of transcription, such regulatory elements can also comprise transcription termination signals, such as SV40-poly-A site or the tk-poly-A site, downstream of the polynucleotide. In this context, suitable expression vectors are known in the art such as Okayama-Berg cDNA expression vector pcDV1 (Pharmacia), pRc/CMV, pcDNA1, pcDNA3 (Invitrogen), pSPORT1 (GIBCO BRL), Casper, Casper-HS43, pUAST, or prokaryotic expression vectors, such as lambda gt11.

Furthermore, depending on the expression system, leader sequences capable of directing the polypeptide to a cellular compartment can be added to the coding sequence of the nucleic acid molecules of the invention and are well known in the art. The leader sequence(s) is assembled in appropriate phase with translation, initiation and termination sequences, and preferably, a leader sequence capable of directing secretion of translated protein, or a protein thereof, into the periplasmic space or extracellular medium. Optionally, the heterologous sequence can encode a fusion protein including an C- or N-terminal identification peptide imparting desired characteristics, e.g., stabilization of expressed recombinant products. Once the vector has been incorporated into the appropriate cell line, the cells are maintained under conditions suitable for high level expression of the nucleotide sequences.

A cell can be transfected or transformed with a recombinant vector encoding the targeting peptide of the present invention. Methods of transformation and transfection are well known in the art. The transformed cells can be grown in fermentors and cultured according to techniques known in the art to achieve optimal cell growth. The resulting transformed or transfected cell lines are genetically modified with a nucleic acid molecule according to the invention or with a vector comprising such a nucleic acid molecule. The term "genetically modified" means that the cell comprises in addition to its natural genome a nucleic acid molecule or vector according to the invention which was introduced into the cell or host or into one of its predecessors/parents. The nucleic acid molecule or vector can be present in the genetically modified cell either as an independent molecule outside the genome, preferably as a molecule that is capable of replication, or it can be stably integrated into the genome of the cell.

The present invention can utilize any suitable prokaryotic or eukaryotic cell. Suitable prokaryotic cells are those generally used for cloning like *Escherichia coli* or *Bacillus subtilis*. Eukaryotic cells comprise, for example, fungal or animal cells, and are generally used for conducting the specificity assay. Animal cells are preferably used for conducting the specificity assay. Suitable animal cells are, for instance, insect cells, vertebrate cells, preferably mammalian cells. Further suitable cell lines known in the art are obtainable from cell line depositories, like the American Type Culture Collection (ATCC) and the AIDS Research and Reference Reagent Program Catalog. Derivation of primary cells from an animal, preferably a mammal, and even more preferably a human, can also be undertaken for the purposes of establishing a suitable cell line.

Targeting Composition Administration

Targeting compositions of the invention can be administered in a pharmaceutically acceptable excipient, such as water, saline, aqueous dextrose, glycerol, or ethanol. The compositions can also contain other medicinal agents, pharmaceutical agents, carriers, and auxiliary substances such as wetting or emulsifying agents, and pH buffering agents.

Standard texts, such as Remington: The Science and Practice of Pharmacy, 17th edition, Mack Publishing Company, incorporated herein by reference, can be consulted to prepare suitable compositions and formulations for administration, without undue experimentation. Suitable dosages can also be based upon the text and documents cited herein. A determination of the appropriate dosages is within the skill of one in the art given the parameters herein.

A "therapeutically effective amount" is an amount sufficient to effect a beneficial or desired clinical result. A therapeutically effective amount can be administered in one or more doses. In terms of treatment, an effective amount is an amount that is sufficient to palliate, ameliorate, stabilize, reverse or slow the progression of a cardiovascular disease characterized by the presence of vulnerable plaques or otherwise reduce the pathological consequences of the impending rupture. A therapeutically effective amount can be provided in one or a series of administrations. The effective amount is generally determined by the physician on a case-by-case basis and is within the skill of one in the art.

As a rule, the dosage for in vivo therapeutics or diagnostics will vary. Several factors are typically taken into account when determining an appropriate dosage. These factors include age, sex and weight of the patient, the condition being treated, the severity of the condition and the form of the antibody being administered.

Radiolabeled compositions of the present invention, optionally coupled to molecular carriers or molecular carriers and photosensitizers, can comprise, for example, from about 1 to about 30 mCi of the radionuclide in combination with a pharmaceutically acceptable carrier. Such compositions may be provided in solution or in lyophilized form. Suitable sterile and physiologically acceptable reconstitution medium include water, saline, buffered saline, and the like. Radionuclides can be combined with the unlabeled molecular carrier/chelating agent and a reducing agent for a sufficient period of time and at a temperature sufficient to chelate the radionuclide to the molecular carrier prior to injection into the patient.

Radiolabeled compositions of the invention can be used in accordance with the methods of the invention by those of skill in the art, e.g., by specialists in nuclear medicine, to image plaque in the cardiovascular system of a subject. Images are generated by virtue of differences in the spatial distribution of the compositions which accumulate in the various tissues and organs of the subject. The spatial distribution of the imaging agent accumulated can be measured using devices of the present invention. Stable atheromatous plaques are evident when a less intense signal is detected, indicating the presence of tissue in which a lower concentration of a radiolabeled composition accumulates relative to the concentration of the same which accumulates in the active atheromatous plaque and/or vulnerable plaque. Alternatively, an active atheromatous plaque and/or vulnerable plaque can be detected as a more intense signal, indicating a region of enhanced concentration of the radiolabeled composition at the site relative to the concentration of the same which accumulates in stable atheromatous plaques. The extent of accumulation of the radiolabeled composition can be quantified using known methods for quantifying radioactive emissions. A particularly useful imaging approach to employs more than one imaging agent to perform simultaneous studies. For example, simultaneous studies of perfusion and metabolic function would allow study of coupling and uncoupling of flow of metabolism, thus facilitating determinations of tissue viability after a cardiac injury. Such determinations are useful in diagnosis of cardiac ischemia, cardiomyopathy, tissue viability, hibernating heart, and other heart abnormalities.

An effective amount of a radiolabeled composition comprising at least one molecular carrier and a radiolabel (e.g. from about 1 to about 50 mCi of a radionuclide), or molecular carrier, photosensitizer and radiolabel, can be combined with a pharmaceutically acceptable carrier for use in detection and/or therapeutic methods. In accordance with the invention, "an effective amount of the radiolabeled composition" of the invention is defined as an amount sufficient to yield an acceptable signal using equipment which is available for clinical use. An effective amount of the radiolabeled composition of the invention can be administered in more than one dose. Effective amounts of the radiolabeled composition of the invention will vary according to factors such as the degree of susceptibility of the individual, the age, sex, and weight of the individual, idiosyncratic responses of the individual, and the dosimetry. Effective amounts of the imaging agent of the invention will also vary according to instrument and film-related factors.

Optimization of such factors is well within the level of skill in the art. In general, the effective amount will be in the range of from about 0.1 to about 10 mg by injection or from about 5 to about 100 mg orally.

The radiolabeled compositions, optionally comprising molecular carriers or molecular carriers and photosensitizers, can be administered to a subject in accordance with any means that facilitates accumulation of the agent in a subject's cardiovascular system. Preferably, the radiolabeled composition of the invention is administered by arterial or venous injection, and has been formulated as a sterile, pyrogen-free, parenterally acceptable aqueous solution. The preparation of such parenterally acceptable solutions, having due regard to pH, isotonicity, stability, and the like, is within the skill in the art. A preferred formulation for intravenous injection should contain an isotonic vehicle such as Sodium Chloride Injection, Ringer's Injection, Dextrose Injection, Dextrose and Sodium Chloride Injection, Lactated Ringer's Injection, or other vehicle as known in the art.

The amount of radiolabeled composition used for diagnostic purposes and the duration of the study will depend upon the nature and severity of the condition being treated, on the nature of therapeutic treatments which the patient has undergone, and on the idiosyncratic responses of the patient. Ultimately, the attending physician will decide the amount of radiolabeled composition to administer to each individual patient and the duration of the imaging study.

The dosage of fluorescent compositions, which include, for example, photosensitizer compositions, can range from about 0.1 to about 10 mg/kg. Methods for administering fluorescent compositions are known in the art, and are described, for example, in U.S. Pat. Nos. 5,952,329, 5,807,881, 5,798,349, 5,776,966, 5,789,433, 5,736,563, 5,484,803 and by (Sperduto et al. (1991) Int. J. Radiat. Oncol. Biol. Phys. 21:441-6; Walther et al. (1997) Urology 50:199-206). Such dosages may vary, for example, depending on whether multiple administrations are given, tissue type and route of administration, the condition of the individual, the desired objective and other factors known to those of skill in the art. Where the fluorescent compositions comprises a photosensitizer conjugated to an antibody, or a "photoimmunoconjugate," dosages can vary from about 0.01 $mg/m^2$ to about 500 $mg/m^2$, preferably about 0.1 $mg/m^2$ to about 200 $mg/m^2$, most preferably about 0.1 $mg/m^2$ to about 10 $mg/m^2$. Ascertaining dosage ranges is well within the skill of one in the art. For instance, the concentration of scFv typically need not be as high as that of native antibodies in order to be therapeutically effective. Administrations can be conducted infrequently, or on a regular weekly basis until a desired, measurable parameter is detected, such as diminution of disease symptoms. Administration can then be diminished, such as to a biweekly or monthly basis, as appropriate.

Compositions of the present invention are administered by a mode appropriate for the form of composition. Available routes of administration include subcutaneous, intramuscular, intraperitoneal, intradermal, oral, intranasal, intrapulmonary (i.e., by aerosol), intravenously, intramuscularly, subcutaneously, intracavity, intrathecally or transdermally, alone or in combination with other pharmaceutical agents. Therapeutic compositions of photosensitizers are often administered by injection or by gradual perfusion.

Compositions for oral, intranasal, or topical administration can be supplied in solid, semisolid or liquid forms, including tablets, capsules, powders, liquids, and suspensions. Compositions for injection can be supplied as liquid solutions or suspensions, as emulsions, or as solid forms suitable for dissolution or suspension in liquid prior to injection. For administration via the respiratory tract, a preferred composition is one that provides a solid, powder, or liquid aerosol when used with an appropriate aerosolizer device. Although not required, compositions are preferably supplied in unit dosage form suitable for administration of a precise amount. Also contemplated by this invention are slow release or sustained release forms, whereby a relatively consistent level of the active compound are provided over an extended period.

Another method of administration is intravascular, for instance by direct injection into the blood vessel, plaque or surrounding area.

Further, it may be desirable to administer the compositions locally to the area in need of treatment; this can be achieved, for example, by local infusion during surgery, by injection, by means of a catheter, or by means of an implant, said implant being of a porous, non-porous, or gelatinous material, including membranes, such as silastic membranes, or fibers. A suitable such membrane is Gliadel® provided by Guilford Pharmaceuticals Inc.

Following administration of the fluorescent composition, it is necessary to wait for the fluorescent composition to reach an effective tissue concentration at the site of the plaque before light activation. Duration of the waiting step varies, depending on factors such as route of administration, tumor location, and speed of photosensitizer movement in the body. In addition, where fluorescent composition target receptors or receptor binding epitopes, the rate of photosensitizer uptake can vary, depending on the level of receptor expression on the surface of the cells. For example, where there is a high level of receptor expression, the rate of binding and uptake is increased. Determining a useful range of waiting step duration is within ordinary skill in the art and may be optimized by utilizing fluorescence optical imaging techniques.

Devices and Methods for Photosensitizer Composition Activation

Following the waiting step, the fluorescent composition is activated by photoactivating light applied to the site of the plaque. This is accomplished by applying light of a suitable wavelength and intensity, for an effective length of time, at the site of the plaque. As used herein, "photoactivation" means a light-induced chemical reaction of a photosensitizer, which produces a biological effect.

Target tissues are illuminated, preferably with red light. Given that red and/or near infrared light best penetrates mammalian tissues, photosensitizers with strong absorbances in the 600 nm to 900 nm range are optimal for PDT. The suitable wavelength, or range of wavelengths, will depend on the particular photosensitizer(s) used. Wavelength specificity for photoactivation depends on the molecular structure of the photosensitizer. Photoactivation occurs with sub-ablative light doses. Determination of suitable wavelength, light intensity, and duration of illumination is within ordinary skill in the art.

For photoactivation, the wavelength of light is matched to the electronic absorption spectrum of the photosensitizer so that photons are absorbed by the photosensitizer and the desired photochemistry can occur. Except where the vessels being treated are very superficial, the range of activating light is typically between 600 and 900 nm. This is because endogenous molecules, in particular hemoglobin, strongly absorb light below 600 nm and therefore capture most of the incoming photons (Parrish et al., (1978) Optical properties of the skin and eyes. New York, N.Y.: Plenum). The net effect would be the impairment of penetration of the activating light through the tissue. The reason for the 900 nm upper limit is that energetics at this wavelength may not be sufficient to produce $^1O_2$, the activated state of oxygen which, without wishing to necessarily be bound by any one theory, is perhaps critical for successful PDT. In addition, water begins to absorb at wavelengths greater than about 900 nm.

The effective penetration depth, $\delta_{eff}$, of a given wavelength of light is a function of the optical properties of the tissue, such as absorption and scatter. The fluence (light dose) in a tissue is related to the depth, d, as: $e^{-d/\delta_{eff}}$. Typically, the effective penetration depth is about 2 to 3 mm at 630 nm and increases to about 5 to 6 nm at longer wavelengths (700-800 nm)(Svaasand and Ellingsen, (1983) Photochem Photobiol. 38:293-299). These values can be altered by altering the biologic interactions and physical characteristics of the photosensitizer. In general, photosensitizers with longer absorbing wavelengths and higher molar absorption coefficients at these wavelengths are more effective photodynamic agents.

PDT dosage depends on various factors, including the amount of the photosensitizer administered, the wavelength of the photoactivating light, the intensity of the photoactivating light, and the duration of illumination by the photoactivating light. Thus, the dose of PDT can be adjusted to a therapeutically effective dose by adjusting one or more of these factors. Such adjustments are within ordinary skill in the art.

The light for photoactivation can be produced and delivered to the plaque site by any suitable means known in the art. Photoactivating light can be delivered to the plaque site from a light source, such as a laser or optical fiber. Preferably, the photoactivating light is delivered by optical fiber devices that directly illuminate the plaque site. For example, the light can be delivered by optical fibers threaded through small gauge hypodermic needles. Light can be delivered by an appropriate intravascular catheter, such as those described in U.S. Pat. Nos. 6,246,901 and 6,096,289, which can contain an optical fiber. Optical fibers can also be passed through arthroscopes. In addition, light can be transmitted by percutaneous instrumentation using optical fibers or cannulated waveguides. For open surgical sites, suitable light sources include broadband conventional light sources, broad arrays of LEDs, and defocused laser beams.

Delivery can be by all methods known in the art, including transillumination. Some photosensitizers can be activated by near infrared light, which penetrates more deeply into biological tissue than other wavelengths. Thus, near infrared light is advantageous for transillumination. Transillumination can be performed using a variety of devices. The devices can utilize laser or non-laser sources, (e.g., lightboxes or convergent light beams).

Where treatment is desired, the dosage of photosensitizer composition, and light activating the photosensitizer composition, is administered in an amount sufficient to produce a phototoxic species. For example, where the photosensitizer composition includes chlorin$_{e6}$, administration to humans is in a dosage range of about 0.5-10 mg/kg, preferably about 1-5 mg/kg more preferably about 2-4 mg/kg and the light delivery time is spaced in intervals of about 30 minutes to about 3 days, preferably about 12 hours to about 48 hours, and more preferably about 24 hours. The light dose administered is in the range of about 20-500 J/cm, preferably about 50-300 J/cm and more preferably about 100-200 J/cm. The fluence rate is in the range of about 20-500 mw/cm, preferably about 50-300 mw/cm and more preferably about 100-200 mw/cm. There is a reciprocal relationship between photosensitizer compositions and light dose, thus, determination of suitable wavelength, light intensity, and duration of illumination is within ordinary skill in the art.

Preferably, the phototoxic species induces apoptosis and not necrosis of the cells comprising the vulnerable plaque. Lowering the fluence rate will favor apoptosis (e.g., less than 100 mw/cm, e.g., 10-60 mw/cm, for chlorin$_{e6}$). Determination of a suitable fluence rate for a photosensitizer composition is within ordinary skill in the art.

Where the fluorescent composition comprises a photoactive dye, the wavelength and power of light can be adjusted according to standard methods known in the art to control the production of phototoxic species. Thus, under certain conditions (e.g., low power, low fluence rate, shorter wavelength of light or some combination thereof), a fluorescent species is produced from the photoactive dye and any reactive species produced has a negligible effect. These conditions are easily adapted to bring about the production of a phototoxic species. For example, where the photoactive dye comprises chlorin$_{e6}$, the light dose administered to produce a fluorescent species and an insubstantial reactive species is less than about 10 J/cm, preferably less than about 5 J/cm and more preferably less than about 1 J/cm. Determination of suitable wavelength, light intensity, and duration of illumination is within ordinary skill in the art.

In a preferred embodiment, photoactivation can be carried out using by a specially designed intravascular device that delivers excitation light to the plaque surface inside the artery and receives emitted fluorescence or other detectable signals (e.g., heat or radioactivity) that are transmitted to an analysis instrument. The same device can optionally be used to deliver therapeutic light when a fluorescent signal, or other measurable signal (e.g., heat or radioactivity) is detected.

FIG. 1A illustrates a detection/treatment system 100 for detecting and/or targeting and/or treating vulnerable plaque in accordance with an embodiment of the invention. As shown in FIG. 1A, detection/treatment system 100 may include a control unit 105 and a detection/treatment unit 110, which may include a light source/laser 113, and a detection/treatment device 115, which may include a probe, a catheter, and so forth.

Control unit 105 may include a power supply, for example, control unit may be coupled to a power source, for supplying power to detection/treatment unit 110. Control unit 105 may also include a computing device having control hardware and/or software for controlling, based on inputted parameters and/or detected properties, detection/treatment unit 110, light source/laser 113 and detection/treatment device 115.

Figure 1B:
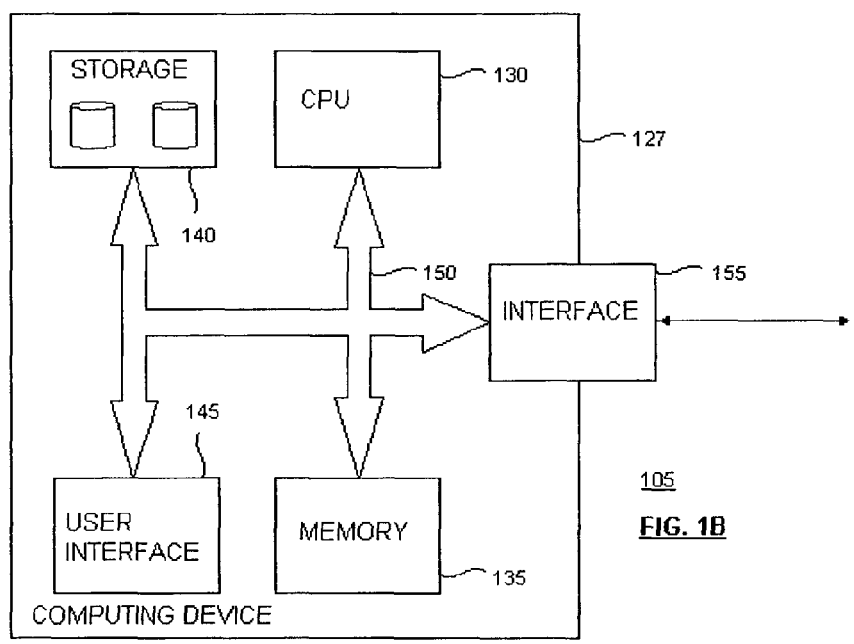
FIG. 1B is a diagram illustrating a configuration of the control unit of FIG. 1A.

FIG. 1B is a diagram illustrating a configuration of control unit 105 in accordance with an embodiment of the invention. As shown in FIG. 1B, control unit 105 may comprise a computing device 125, which may be a general purpose computer (such as a PC), workstation, mainframe computer system, and so forth. Computing device 125 may include a processor device (or central processing unit "CPU") 130, a memory device 135, a storage device 140, a user interface 145, a system bus 150, and a communication interface 155. CPU 130 may be any type of processing device for carrying out instructions, processing data, and so forth. Memory device 135 may be any type of memory device including any one or more of random access memory ("RAM"), read-only memory ("ROM"), Flash memory, Electrically Erasable Programmable Read Only Memory ("EEPROM"), and so forth. Storage device 140 may be any data storage device for reading/writing from/to any removable and/or integrated optical, magnetic, and/or optical-magneto storage medium, and the like (e.g., a hard disk, a compact disc-read-only memory "CD-ROM", CD-ReWritable "CD-RW", Digital Versatile Disc-ROM "DVD-ROM", DVD-RW, and so forth). Storage device 140 may also include a controller/interface (not shown) for connecting to system bus 150. Thus, memory device 135 and storage device 140 are suitable for storing data as well as instructions for programmed processes for execution on CPU 130. User interface 145 may include a touch screen, control panel, keyboard, keypad, display or any other type of interface, which may be connected to system bus 150 through a corresponding input/output device interface/adapter (not shown). Communication interface 155 maybe adapted to communicate with any type of external device, including detection/treatment unit 110. Communication interface 155 may further be adapted to communicate with any system or network (not shown), such as one or more computing devices on a local area network ("LAN"), wide area network ("WAN"), the internet, and so forth. Interface 155 may be connected directly to system bus 150, or may be connected through a suitable interface (not shown). Control unit 105 may, thus, provide for executing processes, by itself and/or in cooperation with one or more additional devices, that may include algorithms for controlling detection/treatment unit 110 in accordance with the present invention. Control unit 105 may be programmed or instructed to perform these processes according to any communication protocol, or programming language on any platform. Thus, the processes may be embodied in data as well as instructions stored in memory device 135 and/or storage device 140 or received at interface 155 and/or user interface 145 for execution on CPU 130.

Referring back to FIG. 1A, detection/treatment unit 110 may be a handheld device, an automated apparatus, and the like. As shown in FIG. 1A, detection/treatment device 115 may be inserted and extended into a blood vessel 120, such as an artery, in tissue 125. Detection/treatment device 115 may be a handheld device, an automated apparatus, and the like. It is further noted that the elements of detection/treatment system 100 may be integrated into a single physical unit or may comprise any number of discrete units, such that any number of these elements or the functionality thereof, may be incorporated into a physical device. As will be described in further detail below, detection/treatment device 115 may include a number of light delivery elements for delivering detected light from targeted plaque, delivering therapeutic light, and/or delivering detection/excitation light.

In accordance with an embodiment of the invention, light source 113 may include a pulse blue laser for delivering detection or excitation light via detection/treatment device 115. Depending on the dye and/or excitation effect on target plaque as described above, reflected and/or emitted light from the target plaque may include light with a particular wavelength and/or frequency, which may then be detected through detection/treatment device 115. A large number of fluorescent probes (e.g., photosensitizers, fluorescent dyes or photoactive dyes) and methods of use thereof (e.g., excitation and emission wavelengths), are described in the Molecular Probes, Inc. catalog, (Handbook of Fluorescent Probes and Research Chemicals, $6^{th}$ Edition by Richard Haugland), the contents of which are hereby incorporated by reference.

In accordance with an embodiment of the invention where in the fluorescent composition or photosensitizer composition includes chlorin$_{e6}$, detection/excitation light may include a wavelength of 337 nm (for example, nitrogen laser), therapeutic light may include a wavelength of 405 nm (for example, pump dye laser), and light or fluorescence emitted from target plaque as a result of excitation by detection/excitation light may include a wavelength of 666-668 nm. The power of detection/excitation light may, for example, be adjusted in accordance with the specific excitation or emission wavelength of the particular fluorescent or photosensitizer composition used. The power of detection/excitation light may, for example, be adjusted in accordance with a size and/or dimension of blood vessel 120. The power of therapeutic light may, for example, be adjusted in accordance with a size and/or dimension of blood vessel 120, and/or the level of light detected from target plaque.

In accordance with an embodiment of the invention, detection/treatment system 100 may include a number of configurations and instruments. Algorithms that are designed for different types of procedures, configurations and/or instruments may be included for control unit 105.

It is noted that detection/treatment system 100 may be controlled remotely. For example, the link between control unit 105 and detection/treatment unit 110 may be a remote link (wired or wireless) providing control unit 105 remote control over light source 113 and detection/treatment device 115.

While the above exemplary detection/treatment system 100 is illustrative of the basic components of a system suitable for use with the present invention, the architecture shown should not be considered limiting since many variations of the hardware configuration are possible without departing from the present invention.

The present invention is additionally described by way of the following illustrative, non-limiting Examples, that provide a better understanding of the present invention and of its many advantages.

As described before, target plaque may accumulate on the wall of blood vessels, e.g. arteries, and the like. Thus, detection/treatment device 115 embodying the present invention may include a probe/catheter and the like, as described below, which may include a number of elements for detecting the target plaque on the wall of these blood vessels, distinguishing the target plaque from non-target plaque and/or treating the target plaque without obstructing the blood flow through these vessels.

Figure 2A:
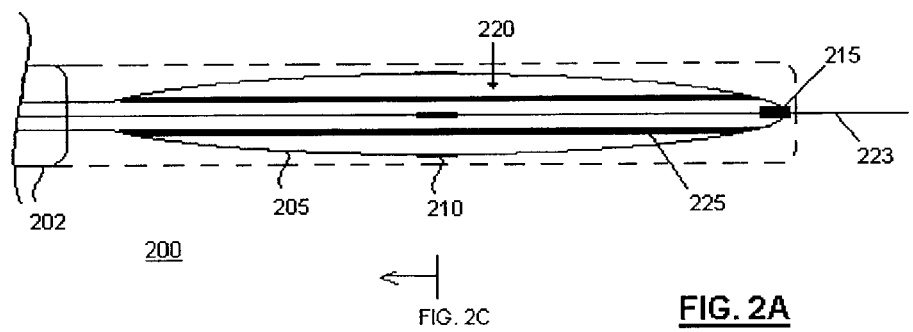
FIGS. 2A and 2B are diagrams showing a probe/catheter in accordance with an embodiment with the present invention.
Figure 2B:
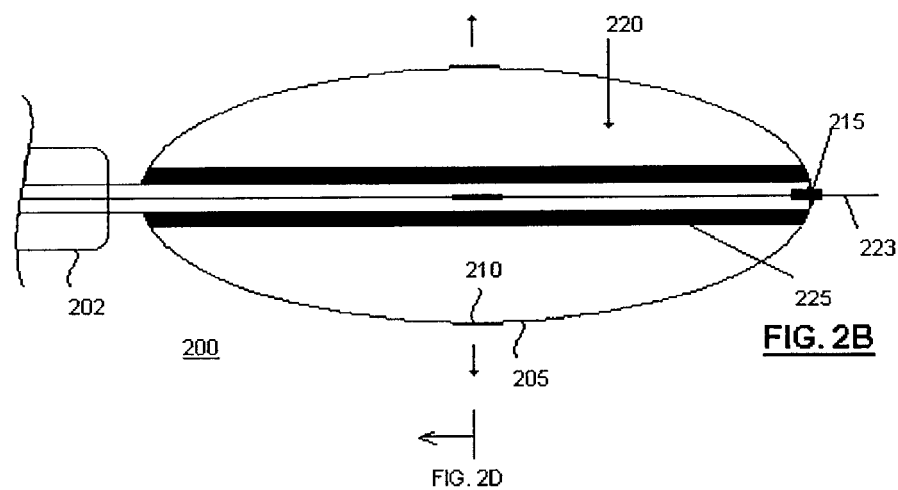

FIGS. 2A, 2B, 2C, 2D, 2E and 2F are diagrams showing a probe/catheter 200 in accordance with an embodiment with the present invention. As shown in FIG. 2A, probe/catheter 200 may include an external unit 202 and an extendible internal unit, which may include a number of light delivery element(s) 205 and light deflection element(s) 210 and a tip 215. As an example, external unit 202 may include any plastic and/or metallic material (e.g., nitinol alloy) and the like. FIG. 2A illustrates probe/catheter 200 with its internal unit retracted within and extended from external unit 202, and FIG. 2B illustrates probe/catheter 200 with its internal unit extended and deployed. In accordance with an embodiment of the invention, the internal unit may be extended and deployed to detect target plaque, then retracted to move probe/catheter 200 to a different area within, say, blood vessel 120. For example, probe/catheter 200 may be used to scan blood vessel 120 where probe/catheter 200 is moved along blood vessel 120 and the internal unit is extended every one to six millimeters to make a detection. A guidewire 223 may be used to guide probe/catheter 200 along blood vessel 120 and/or extend/retract the internal unit (e.g., light delivery element(s) 205 and light deflection elements 210, and so forth) from/into external unit 202. As an example, guidewire 223 may include any plastic and/or metallic material (e.g., nitinol alloy) and the like. Light deflection element(s) 210 may include a smooth surface for contacting the wall of blood vessel 120, thus allowing detection while probe/catheter 200 is being moved. Detection may be made without contacting the wall or probe/catheter 200 may also be stopped to make such a detection. Probe/catheter 200 may include four light delivery elements 205, each including a light deflection element 210. Each of the four light delivery elements 205 may be disposed such that the corresponding light deflection elements 210 form a circumference separated by 90 degrees, as shown by the cross-sectional views in FIGS. 2C and 2D. It is noted that probe/catheter 200 may include any number of light delivery element(s) 205 (and light deflection element(s) 210) separated by a corresponding angle around a circumference for covering a divided area of the surrounding wall of blood vessel 120. Probe/catheter 200 may also be rotatable to cover the circumference of blood vessel 120. In accordance with a preferred embodiment of the invention, probe/catheter 200 may include three to six light delivery elements 205 (and light deflection elements 210). It is noted, of course, that light delivery elements 205 may be split from a single element connected to detection/treatment unit 110 or they may be separately connected to detection/treatment unit 110.

As will be described in further detail below, light deflection element(s) 210 may deflect external light received from blood vessel 120 into light delivery element(s) 205, which may then deliver the received light to detection/treatment unit 110 and/or control unit 105 for analysis. Light deflection element(s) 210 may also deflect detection/excitation light, which may be delivered from detection/treatment unit 110 through light delivery element(s) 205, and shine the detection/excitation light onto a target area in blood vessel 120. And so, reflected light and/or light emitted from excited target plaque may be received as described above. Depending on the dye and/or excitation effect on target plaque as described before, the target plaque may reflect and/or emit light having a particular wavelength and/or frequency. Thus, target plaque may be identified and located by detecting and identifying light having such a particular wavelength and/or frequency from the light received from blood vessel 120.

Light delivery element(s) 205 may include an optical fiber for delivering light received at its corresponding light deflection element(s) 210 to treatment unit 110 and/or control unit 105. Light delivery element(s) 205 may also deliver detection/excitation light from light source 113 to its corresponding light deflection element(s) 210 where it is deflected and shone onto blood vessel 120. As shown in FIG. 2A, light delivery element(s) 205 may extend to and joined at a tip 215.

As shown in FIG. 2B, light delivery element(s) 205 may move outward so that light deflection element(s) 210 are moved towards the surrounding wall of blood vessel 120, thus allowing better plaque detection. In accordance with an embodiment of the invention, light delivery element(s) 205 may include a rigid and/or spring-like structure, for example, a plastic structure, such that the structure expands when extended, as shown in FIG. 2B, and may be compressed within external unit 202 when retracted, as shown in FIG. 2A. The rigid structure may include any elastic material so that the structure expands to substantially the same size and shape every time it is extended as shown in FIG. 2B.

In accordance with an embodiment of the invention, probe/catheter 200 may include a vessel (or "balloon") 220 that may be expanded by filling it with a fluid. Thus, when extended as shown in FIG. 2B, vessel 220 may be filled with fluid and expanded, pushing light deflection element(s) 210 towards the surrounding wall of blood vessel 120. The fluid may be any nontoxic fluid, such as saline and so forth. As an example, vessel 220 may include any elastic material, such as rubber or latex, and the like. Control unit 105 and/or detection/treatment unit 110 may control fluid flow to and from vessel 220 so that fluid is delivered thereto when probe/catheter 200 is extended, and drained when probe/catheter 200 is retracted. Advantageously, the amount of fluid may be controlled so as to fit the size of the surrounding blood vessel 120. In other words, less fluid may be delivered if blood vessel 120 is relatively small and more fluid may be delivered if blood vessel 120 is relatively large. Thus, light deflection element(s) 210 may be moved towards the wall of a blood vessel 120 of any size, while preventing light deflection element(s) 210 from being pressed against the wall of a smaller blood vessel 120.

Figure 2C:
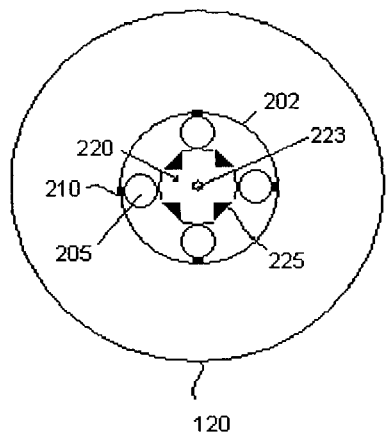
FIGS. 2C and 2D are diagrams showing alternative views of FIGS. 2A and 2B, respectively.
Figure 2D:
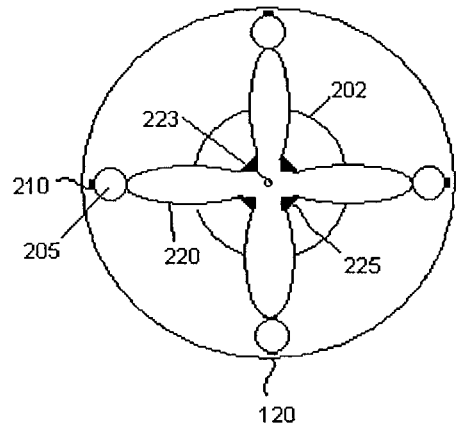

FIGS. 2C and 2D are diagrams showing cross-sectional views of FIGS. 2A and 2B, respectively. When expanding vessel 220 or otherwise moving light deflection element(s) 210 towards the wall of blood vessel 120, it is important that blood flow through blood vessel 120 be unhindered. Therefore, in accordance with an embodiment of the invention, vessel 220 may include a number of rigid element(s) 225 so that only a particular portion of vessel 220 expands when filled with fluid. As an example, rigid element(s) 225 may include a rigid material, for instance any plastic and/or metallic material (e.g., nitinol alloy), and the like. As shown in FIGS. 2C and 2D, vessel 220 may include four rigid element(s) 225, such as plastic ribbings, and the like. As shown in FIG. 2D, rigid element(s) 225 may hold vessel 220 in place where only regions of vessel 220 that are adjacent light delivery element(s) 205 and light deflection element(s) 210 may expand outward. Therefore, vessel 220 does not substantially block blood vessel 120 when it is expanded. Light deflection element(s) 210 may, thus, be moved outward to the wall of blood vessel 120 without obstructing blood flow.

Figure 2E:
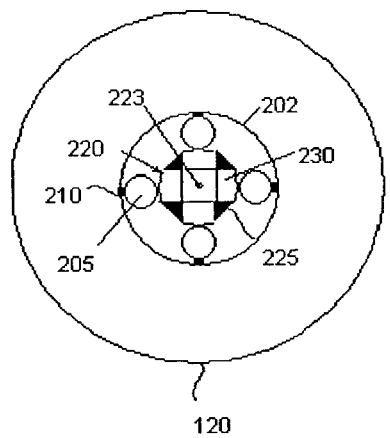
FIGS. 2E and 2F illustrate a probe/catheter in accordance with an embodiment of the invention.
Figure 2F:
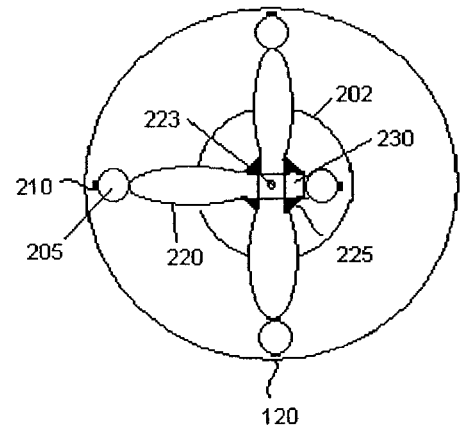

FIGS. 2E and 2F illustrate cross-sectional views of probe/catheter 200 in accordance with an embodiment of the invention. As shown in FIGS. 2E and 2F, vessel 220 may include an isolated chamber corresponding to a particular light deflection element 210. Therefore, each of any number of particular light deflection element(s) 210 may correspond to such a chamber in vessel 220 so that element(s) 210 can be individually moved towards and away from the wall of blood vessel 120, by individually inflating and deflating each chamber. For example, as shown in FIG. 2F, a chamber 230 may be individually deflated (i.e., drained of fluid), in the event that therapeutic light may be directed to the corresponding region on blood vessel 120, say, from tip 215, in the event that the corresponding region need not be detected or monitored for any reason, or to fit to a particular dimension of a blood vessel.

FIGS. 3A, 3B and 3C are diagrams illustrating a probe/catheter 300 in accordance with an embodiment of the invention. Probe/catheter 300 as shown in FIGS. 3A and 3B is similar to probe/catheter 200 shown in FIGS. 2A and 2B, respectively, except that probe/catheter 300 may include only one light delivery element 205 and corresponding light deflection element 210. Advantageously, the cross-sectional area of probe/catheter 300, when extended and deployed, may be further reduced. For example, as shown in FIG. 3C, probe/catheter 300 may include only one prong compared to the four prongs shown in FIG. 2D for probe/catheter 200. As a result, blood flow obstruction may be further reduced. Probe/catheter 200 may include a platform 305 for supporting, say, vessel 220. As an example, platform 305 may include a rigid material, for instance any plastic and/or metallic material (e.g., nitinol alloy), and the like, so that it is held in place while vessel 220 expands and pushes light deflection element 210 outward. As mentioned before, light delivery element 205 may include a rigid structure that pushes outward when extended from external unit 202. Platform 305 may support such a structure.

Figure 4A:
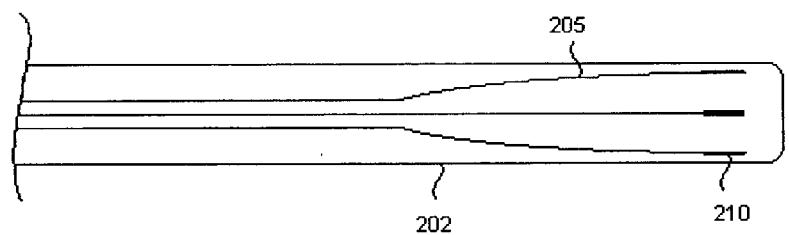
FIGS. 4A and 4B show a probe/catheter in accordance with an embodiment of the invention.
Figure 4B:
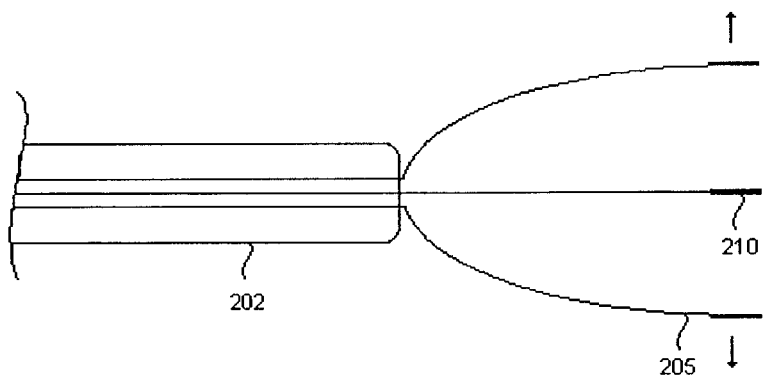

FIGS. 4A and 4B show a probe/catheter 400 in accordance with an embodiment of the invention. As shown in FIGS. 4A and 4B, probe/catheter 400 may include light delivery elements 205 disposed on a rigid structure that is compressed when enclosed in external unit 202, as shown in FIG. 4A, and expands when extended, as shown in FIG. 4B. As described before, the rigid structure may include any elastic material so that the structure expands to substantially the same size and shape every time it is extended as shown in FIG. 4B. As an example, the rigid structure may include any plastic and/or metallic material (e.g., nitinol alloy) and the like.

Figure 5A:
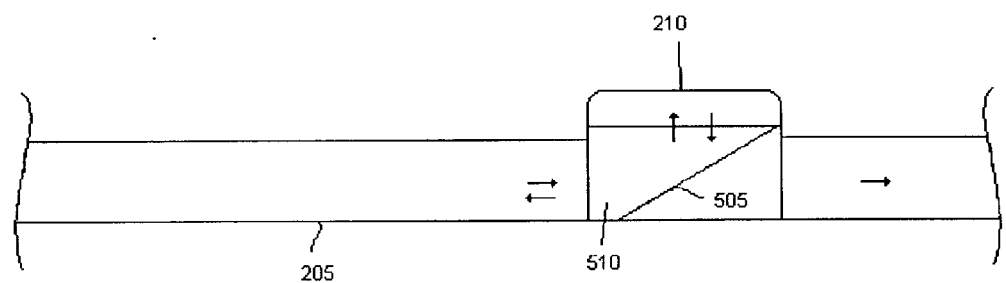
FIGS. 5A and 5B are diagrams illustrating a light delivery element and a light deflection element in accordance with respective embodiments of the invention.
Figure 5B:
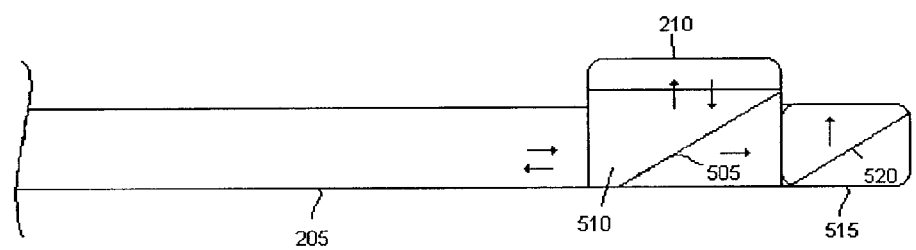

FIGS. 5A and 5B are diagrams illustrating light delivery element 205 and light deflection element 210 in accordance with respective embodiments of the invention. As shown in FIG. 5A, light deflection element 210 may include a reflective surface 505 and/or a refractive element 510 for deflecting light from a target area back to detection/treatment unit 110 through light delivery element 205, and/or deflecting detection/excitation light from light source 113 to the target area. In accordance with an embodiment of the invention, light source 113 may include a light source for therapeutic light having a difference wavelength and/or frequency. Thus, light deflection element 210 may deflect only detection/excitation light, while allowing therapeutic light to pass through. Referring back to FIGS. 2A and 2B, the passed through therapeutic light may be deflected out at tip 215 for effecting treatment on the surrounding wall of blood vessel 120. Probe/catheter 200 may further be extended and/or retracted partially when effecting treatment so as to ensure that therapeutic light from tip 215 reaches the areas covered by light deflection element(s) 210.

FIGS. 5B illustrates light deflection element 210 that may be used in probe/catheter 400, as shown in FIGS. 4A and 4B, in accordance an embodiment of the invention. As shown in FIG. 5B, a therapeutic light deflection unit 515 may be placed adjacent light deflection element 210. Since it is advantageous to target therapeutic light more broadly to cover tissue surrounding the detected plaque, therapeutic light deflection unit 515 may include a refractive material for spreading or diffusing the therapeutic light in all directions to cover the surrounding wall of blood vessel 120. In accordance with an embodiment of the invention, therapeutic light deflection unit 515 may also include a reflective element 520 for targeting the therapeutic light to a general direction or a particular area. Thus, referring back to FIGS. 4A and 4B, a therapeutic light deflection unit 515 may be disposed at the end, or tip, of each light deflection element 210. In accordance with an embodiment of the invention, detection/excitation light and therapeutic light may be carried on separate light delivery elements.

Figure 6A:
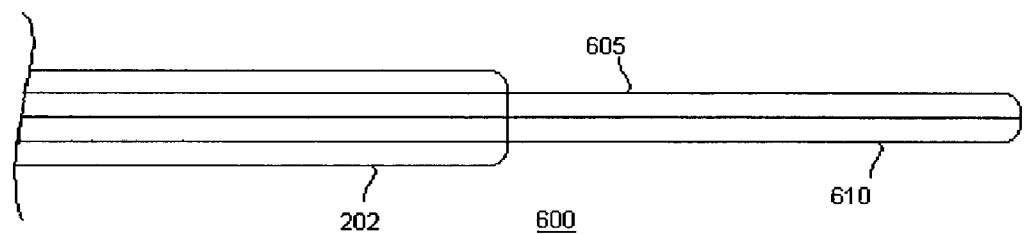
FIGS. 6A, 6B and 6C illustrate a probe/catheter in accordance with an embodiment of the present invention.
Figure 6B:
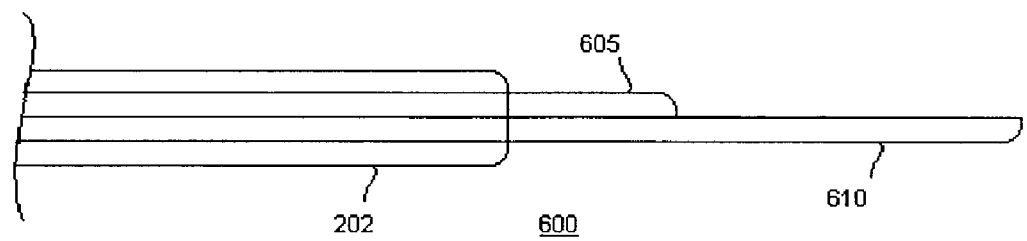
Figure 6C:
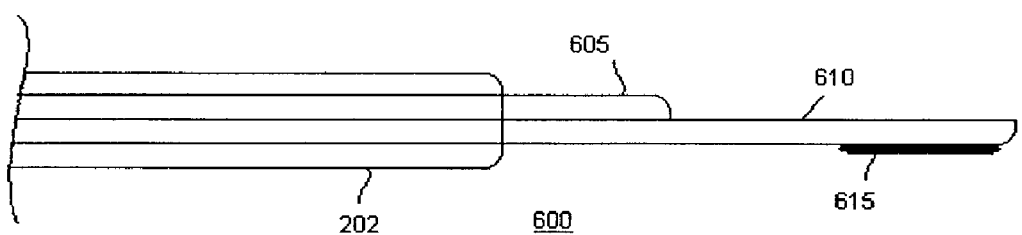

FIGS. 6A, 6B, and 6C illustrate a probe/catheter 600 in accordance with an embodiment of the present invention. As shown in FIG. 6A, probe/catheter 600 may include a detector 605, such as a scintillation detector, and the like, for detecting emitted and/or reflected light, radioactive signals (e.g., gamma rays, beta rays, and so forth), nuclear isotopes, radio frequency/microwave signals, magnetic fields, electric fields, temperature (e.g., heat), vibration, and so forth. By detecting any one or more of the foregoing, target plaque may be identified and/or located from surrounding plaque/tissue. As further shown in FIG. 6A, probe/catheter 600 may also include a therapeutic light deflector 610, such as a diffusing fiber, and the like, for diffusing therapeutic light to surrounding plaque/tissue. As shown in FIG. 6B, detector 605 may be independently retracted so that therapeutic light may be directed to the general direction or particular area where target plaque/tissue is detected. Furthermore, as shown in FIG. 6C, therapeutic light deflector 610 may include a reflective element 615, such as a shield, and the like, to block therapeutic light from diffusing to a non-target direction. For example, after detector 605 detects target plaque/tissue, it may be retracted and therapeutic light deflector 610 and reflective element 615 may diffuse therapeutic light only to the general direction and/or target area covered by detector 605. In accordance with an embodiment of the invention, probe/catheter 600 may be rotatable in, say, blood vessel 120 so that detector 605 and therapeutic light may be directed in any direction therewithin.

Figure 16A:
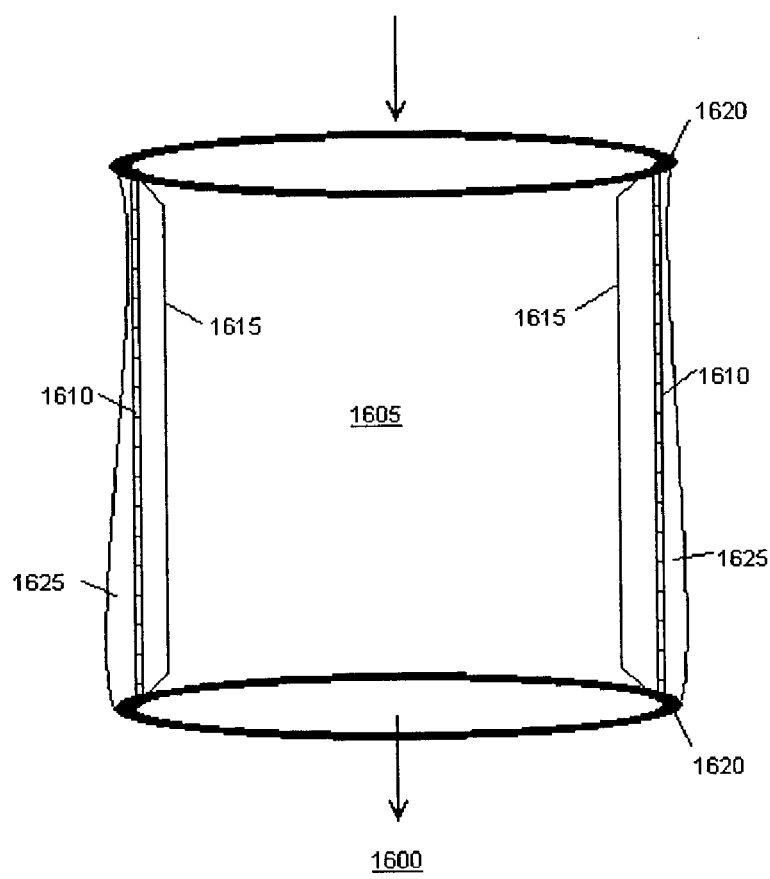
FIGS. 16A and 16B are diagrams illustrating a probe/catheter 1600 in accordance with an embodiment of the invention.
Figure 16B:
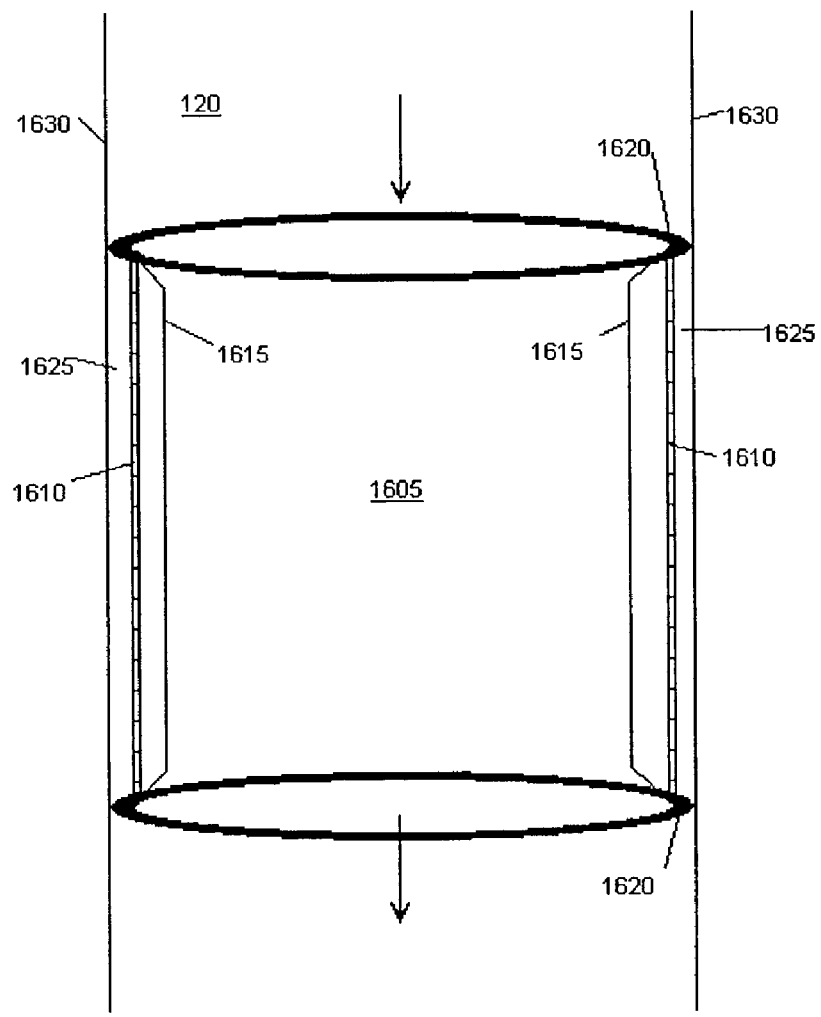

FIGS. 16A and 16B are diagrams illustrating a probe/catheter 1600 in accordance with an embodiment of the invention. Probe/catheter 1600 may include a cylindrical structure with an open, or hollow, center region 1605, so that when probe/catheter 1600 is deploy in blood vessel 120, blood can flow through center region 1605, as shown in FIG. 16B. One or more light delivery and/or deflection elements 1610 may be disposed along the outer surface of the cylindrical structure. Light delivery/deflection elements 1610 may deliver detection/excitation light and/or therapeutic light from light source 113 and shine the detection/excitation light and/or therapeutic light outward from the circumference of the cylindrical structure towards the surrounding wall of blood vessel 120. Probe/catheter 1600 may include a corresponding black seal mash 1615 for each light delivery/deflection element 1610. Black seal mash 1615 may be placed around an inner portion of the cylindrical structure of probe/catheter 1600 from light delivery/deflection elements 1610. Probe/catheter 1600 may also include a pair of black seal rings 1620 on either end of the cylindrical structure. Preferably, as shown in FIG. 16B, black seal rings 1620 engage the wall 1630 of blood vessel 120. Black seal rings 1620 and black seal mash 1615 may include light absorbing and/or outward reflecting material. As a result, black seal rings 1620 and black seal mash 1615 may form a light seal around a region on vessel wall 1635 where detection/excitation light and/or therapeutic light would be targeted. Thus, black seal rings 1620 and black seal mash 1615 may absorb or deflect outward any stray detection/excitation light and/or therapeutic light. Advantageously, blood flowing through center region 1605 would be protected from any stray detection/excitation light and/or therapeutic light. Probe/catheter 1600 may further include a vessel (or "balloon") 1625 that may be expanded by filling it with a fluid. The fluid may be any non-toxic fluid but is preferably a transparent fluid. Vessel 1625 may include any elastic material, such as rubber or latex, and the like, and includes preferably a transparent material.

Control unit 105 and/or detection/treatment unit 110 may control fluid flow to and from vessel 1625 so that fluid is delivered thereto when, as shown in FIG. 16B, vessel 1625 is filled with fluid and expanded, engaging the surrounding wall 1635 of blood vessel 120. Consequently, black seal rings 1620 and vessel 1625 may form a seal between light delivery/deflection elements 1610 and the surrounding wall 1635 of blood vessel 120. In other words, this seal prevents blood in vessel 120 from flowing between light delivery/deflection elements 1610 and the surrounding wall 1635 of blood vessel 120. Advantageously, detection/excitation light and/or therapeutic light may be delivered/deflected from light delivery/deflection elements 1610 to the surrounding wall 1635 without any interference from the blood flowing through blood vessel 120.

Figure 17A:
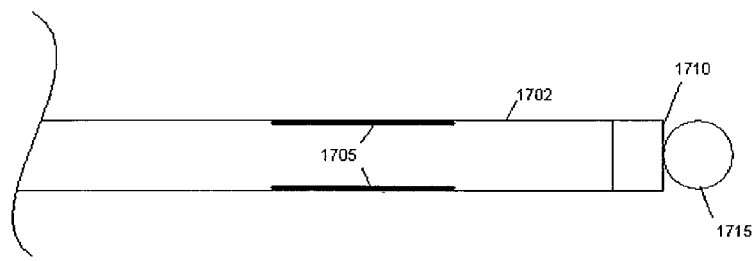
FIGS. 17A and 17B show a probe/catheter 1700 in accordance with an embodiment of the present invention.
Figure 17B:
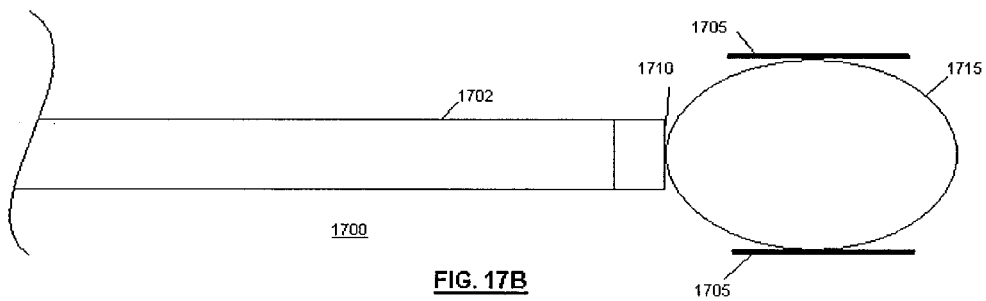

FIGS. 17A and 17B show a probe/catheter 1700 in accordance with an embodiment of the present invention. As shown in FIGS. 17A and 17B, probe/catheter 1700 may include an external unit 1702, a therapeutic structure 1705, a detector 1710 and a vessel 1715. External unit 1702, detector 1710 and vessel 1715 may operate in a similar manner to external unit 202, detector 605 and vessel 220, respectively, as described above. Description of such operations will not be repeated here.

Probe/catheter 1700 advantageously includes a therapy release system allowing more accurate medication delivery to an artherosclerotic injury. The device and methods allow deposition of a therapy regiment in the immediate area of a plaque-diagnosed region. Detector 1710 may include a fluorescence, temperature, or beta detection probe and therapeutic structure 1705 may include a medicated stent.

As shown in FIGS. 17A and 17B, detector 1710 and stent 1705 may be mounted on the catheter type used for balloon catheterisation. Probe/catheter 1700 may be inserted into the femoral or carotid artery as used by catheterisation physicians. Probe/catheter may be moved through the artery until vulnerable plaque or plaque zone is detected by their elevated amount of beta radiation, temperature, or fluorescence emission on the arterial wall. As describe above, the detection may be determined by an increased beta emitting signal or fluorescence color of a preinjected plaque-targeted diagnostic agent, or increased temperature due to inflammatory process. After the location of the plaque formation region, plaque or vulnerable plaque, is detected, stent 1705 may be pushed forward out from external unit 1702, as shown in FIG. 17B. Stent 1705 may thus be move to the exact location on or near the arterial wall by inflating vessel 1715. Stent 1705 may be attached to a lower part of probe/catheter 1700 and after the correct location of plaque has been determined, stent 1705 may be deposited by an action, which resembles that of a sleeve. In accordance with another embodiment, stent 1705 may be a cover of probe/catheter 1700 and be deployed by inflating vessel 1715 at the area of the diagnosed plaque. Probe/catheter 1700 may then be disconnected from the inflated stent 1705.

The therapeutic compounds that heal or prevent the formation of the internal hyperplasia or vulnerable plaque are incorporated in the coating of stent 1705, or as integral part of a porous support on stent 1705, may be released in the exact location where vulnerable plaque or restinosis may occur. The medication or radiation treatment may be assembled or absorbed on tiny porous cavities on stent 1705 and slowly released directly or via the delivery of a second drug to the body of the patient. Furthermore, the drugs, peptides, glycopeptides protein glycoproteins, antisense, DNA or their modifications may be attached or fixed on stent 1705. A biodegradable polymer or a specifically modified delivery polymer, and drugs may be enclosed in an organic or inorganic chemical matrix and be fixed on stent 1705. Stent 1705 may be coated or attached by other forms to antibody or ligand or compound which may attract and/or bind the medication, chosen from anti-infective or other plaque-preventing drugs which are in combination with stent 1705 given systemically from time to time to control, prevent or treat plaque formation or thrombus. Stent 1705 may have a trapped enzyme in forms such as sol gel, fulrenes, or other inert inorganic or organic matrix.

In the case where detector 1710 is a beta emitting radioactive detector, stent 1705 may be pulled back a distance that is far enough from detector 1710 while it is working to find the location of the plaque. This may prevent false readings from the radioactive accumulation in the vulnerable plaque. Since beta rays have short ranges in the order of a few millimeters, any affect on the readings of detector 1710 may be prevented by retracting stent 1705 such distances.

Examples of treatment compounds include: for brachytherapy, an appropriate treatment radionuclide may be enclosed in the matrix without the tissue being physically exposed to the radionuclide that is able to emit the radiation necessary to treat the tissue; and an enzyme such as NTPase like 6CD39 or similar structure in the matrix, without the enzyme or the polymeric derived enzyme being in contact with the tissue. The chemical precursors may move freely through the matrix and be transformed to the plaque prevention form. In the case of NTPase the degradation of ADP may prevent the plaque internal hyperplasia formation.

The present invention is additionally described by way of the following illustrative, non-limiting Examples, that provide a better understanding of the present invention and of its many advantages.

EXAMPLES

Example 1

Preparation and Purification of Photosensitizer Compositions

A photosensitizer composition comprising chlorin$_{e6}$ ("$c_{e6}$") coupled to maleylated-albumin) was prepared for optimal targeting to macrophages of a vulnerable plaque animal model system.

Results

Figure 7:
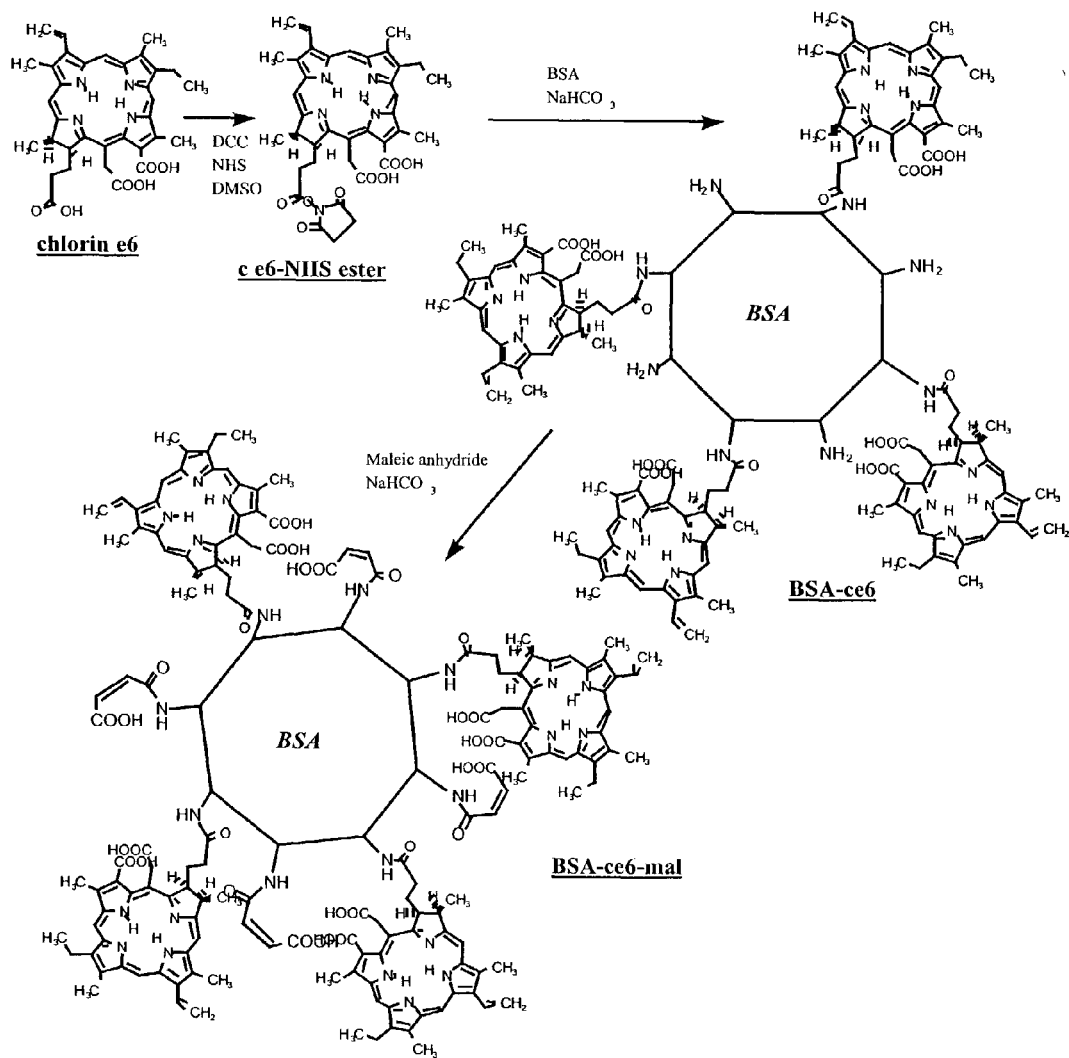
FIG. 7 shows the scheme for preparing chlorin e6 photosensitizer conjugates.

Four photosensitizer compositions were studied (i.e., two BSA-$c_{e6}$ conjugates and their maleylated counterparts). The N-hydroxy succinimide (NHS) ester of $c_{e6}$ was prepared by reacting approximately 1.5 equivalents of dicyclohexylcarbodiimide and approximately 1.5 equivalents of NHS with approximately 1 equivalent of $c_{e6}$ (Porphyrin Products, Logan, Utah) in dry DMSO. After standing in the dark at room temperature for approximately 24 hours, the NHS ester was frozen in aliquots for further use. BSA (Sigma Chemical Co, St Louis, Mo.) (approximately 2×50 mg) was dissolved in NaHCO$_3$ buffer (0.1 M, pH 9.3, approximately 3 ml), and approximately 30 µl and approximately 120 µl of $c_{e6}$-NHS ester added to respective tubes with vortex mixing. After standing in the dark at room temperature for approximately 6 hours, the crude conjugate preparations were each divided into two approximately equal parts. One portion of each of the conjugate preparations was maleylated by adding solid maleic anhydride (approximately 20 mg) to the protein preparation in portions and with vortex mixing, and by adding saturated NaHCO$_3$ solution as needed to keep the pH above approximately 7.0 (Takata et al. (1989) Biochim. Biophys. Acta 984:273). The reaction mixture was allowed to stand at room temp in the dark for approximately 3 hours (FIG. 7). Unmodified BSA was also maleylated to act as a control and as a competitor for the cellular uptake of conjugates.

Crude conjugate preparations (approximately 5 mg/ml) were added to approximately 10× volume of acetone (ACS grade) slowly at approximately 4° C., and were kept at approximately 4° C. for approximately 6 hours, followed by centrifugation at about 4000×g for approximately 15 minutes at about 4° C. The supernatant was removed and the pellet again suspended in approximately the same volume of acetone and the centrifugation repeated. After each precipitation step the preparation was monitored by thin layer chromatography (TLC). Approximately five precipitation steps were necessary to completely remove non-covalently bound chlorin species. Finally, the pellet was dissolved in approximately 2 ml PBS and dialyzed approximately twice against 20 L PBS overnight to remove traces of acetone.

Sephadex G50 column chromatography was carried out by applying the reaction mixture from conjugation of approximately 50 mg BSA with approximately 5 mg $c_{e6}$-NHS ester to a 50×1 cm Sephadex column that was eluted with PBS at about 4° C. The absorbance of the eluted fractions was monitored at 400 nm and at 280 nm.

Figure 8:
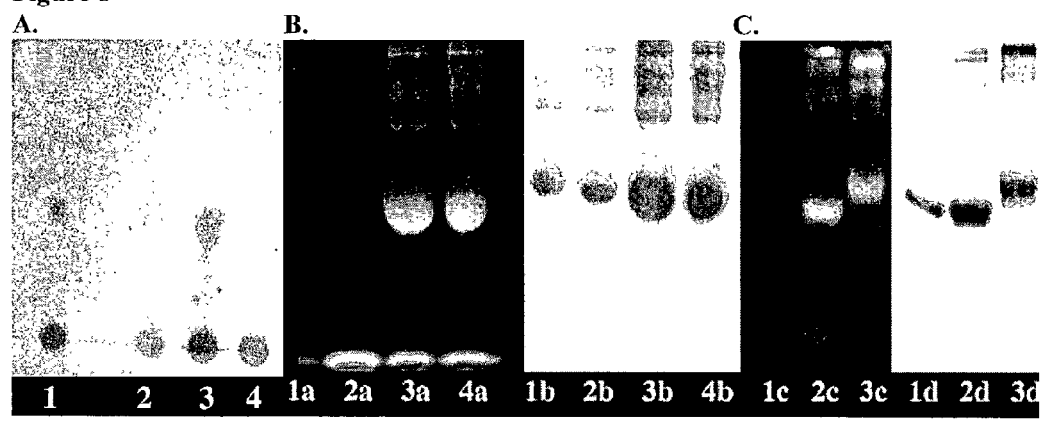
FIG. 8 shows BSA-$c_{e6}$ purified from unreacted $c_{e6}$-NHS ester using a Sephadex G50 column and acetone precipitation (8A: Thin Layer Chromatography; 8B: SDS-PAGE gel visualized by fluorescence (left) and Coomassie stain (right) before acetone precipitation; 8C: SDS-PAGE gel visualized by fluorescence (left) and Coomassie stain (right) after acetone precipitation)

A problem that can be encountered in the preparation of covalent conjugates of tetrapyrrole photosensitizer (PS) with proteins is the tendency of the dye to form tightly bound non-covalent complexes, as well as conjugates. These mixtures can be difficult to separate into pure conjugate and non-bound dye. This is illustrated by the attempted use of a Sephadex G50 column to separate the BSA-$c_{e6}$ conjugate from unreacted $c_{e6}$-NHS ester and its subsequent reaction products. Monitoring of the eluted fractions at 400 nm and at 280 nm showed a single peak that contained both $c_{e6}$ and protein. However, when the material obtained from combining the fractions was examined by TLC, as shown in FIG. 8A, it was apparent that there was a considerable amount of unbound dye present. Lane 1 on the TLC shows the single peak isolated from the size exclusion column and demonstrates that there was still considerable unbound $c_{e6}$ present as a fast running spot. When this material was used in cell-uptake experiments, it was difficult to distinguish receptor targeting between J774 and EMT-6 cell due to indiscriminate uptake of unbound $c_{e6}$ by both receptor-positive and receptor-negative cells. Likewise, lane 3 shows the crude mixture after maleylation and that there was unbound $c_{e6}$ present.

Therefore, the conjugates were purified using an acetone precipitation that allowed the lipophilic $c_{e6}$ species to be retained in the acetone supernatant and the precipitated conjugates to be redissolved in a purified form. The sodium dodecyl sulfate polyacrylamide (SDS-PAGE) gels were viewed by fluorescence imaging to localize the $c_{e6}$ after staining with Coomassie Blue. FIG. 8B shows the corresponding fluorescence and Coomassie images of BSA, BSA mixed with free $c_{e6}$ and conjugates (BSA-$c_{e6}$ 1 and mal-BSA-$c_{e6}$ 1) after Sepahadex column chromatography, but before acetone precipitation. The mixture of BSA and $c_{e6}$ (lanes 2a and 2b) showed that no fluorescence is retained by the protein band on the gel, thus demonstrating that a fluorescent band localizing with the protein is evidence of covalent conjugation. The lanes of the conjugates (3a and 3b, 4a and 4b) show that a fluorescent band running at the gel front remained after Sephadex chromatography.

The efficiency of the purification by acetone precipitation of the conjugates was confirmed by the gel electrophoresis images shown in FIG. 8C. It can be seen that the fast running fluorescent band disappeared from both the BSA-$c_{e6}$ and the mal-BSA-$c_{e6}$ (lanes 2c and 2d, 3c and 3d), while the TLC also showed the disappearance of the fast running spot (FIG. 8A, lanes 2 and 4)

The concentrations of the constituents in the conjugates and, hence the substitution ratios, were measured by absorbance spectroscopy. An aliquot of the conjugate was diluted in approximately 0.1 M NaOH/1% SDS and absorbance between 240 nm and 700 nm scanned. The extinction coefficient of BSA at 280 nm is approximately 47000 cm$^{-1}$M$^{-1}$ (Markwell et al. (1978) Anal Biochem 87:206) while the extinction coefficient of $c_{e6}$ at 400 nm is approximately 150000 cm$^{-1}$M$^{-1}$. Thin layer chromatography was performed on silica gel plates (Polygram SIL G/UV254, Macherey Nagel, Duren, Germany). The chromatograms were developed with an approximately 1:1 mixture of approximately 10% aqueous ammonium chloride and methanol, and spots were observed with fluorescence and absorbance imaging. SDS-PAGE was carried out essentially according to the methods known in the art (Laemmli (1970) Nature 227:680). Gradients of 4-10% acrylamide were used in a non-reducing gel and $c_{e6}$ was localized on the gel by a fluorometer (excitation at 400-440 nm bandpass filter, emission scanned from 580-720 nm longpass filter (Chemilmager 4000, Alpha Innotech Corp, San Leandro, Calif.). Proteins were localized by Coomassie blue staining.

Figure 9:
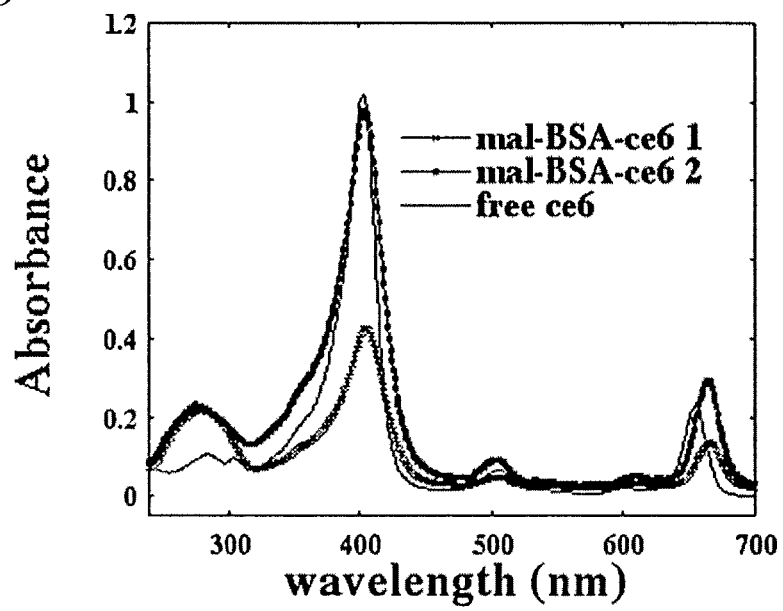
FIG. 9 shows the UV-visible absorption spectra of the purified mal-BSA-$c_{e6}$ conjugates and free $c_{e6}$.

The UV-visible absorption spectra of the purified mal-BSA-$_{e6}$ conjugates with the two substitution ratios measured at approximately equal protein concentrations are shown in FIG. 9, together with free $c_{e6}$ at approximately the same concentration as was present in mal-BSA-$c_{e6}$ 2. Similar spectra were obtained for BSA-$c_{e6}$ 1 and 2. Using the values for molar extinction coefficients of BSA at 280 nm of approximately 47000 cm$^{-1}$M$^{-1}$ (Markwell et al (1978) Anal Biochem 87:206) and $c_{e6}$ at 400 nm of approximately 150000 cm$^{-1}$M$^{-1}$, and correcting for the small absorbance of $c_{e6}$ at 280 nm, then the substitution ratios can be calculated to be mal-BSA-$c_{c6}$ 1 ratio equals approximately 1 protein to approximately 1 dye, and mal-BSA-$c_{e6}$ 2, ratio equals approximately 1 protein to approximately 3 dye.

Example 2

Macrophage-Targeting of Photo Sensitizers

The photosensitizer composition comprising chlorin$_{e6}$ coupled to maleylated-albumin described in Example 1 was shown to accumulate in the macrophage-rich plaques of an animal model system that are analogous to vulnerable plaques in humans. Thus, methods of the present invention provide highly specific intravascular detection and therapy of vulnerable plaques.

Cell Culture

J774.A1 (J774) and RAW 264.7 mouse macrophage-like cell lines, together with EMT-6 mouse mammary fibrosarcoma cells, were obtained from ATCC (Rockville, Md.). Cells were grown in RPMI 1640 media containing HEPES, glutamine, 10% fetal calf serum (FCS), 100 U/ml penicillin and 100 µg/ml streptomycin. They were passaged by washing with phosphate buffered saline (PBS) without Ca$^{2+}$ and Mg$^{2+}$ and by adding trypsin-EDTA to the plate for 10 minutes at 37° C.

Rabbits

Male New Zealand white rabbits weight 2.5-3.0 kg (Charles River Breeding Lab) were maintained on a 2% cholesterol-6% peanut oil diet (ICN) for 6 weeks.

Results

For cellular uptake studies, cells were grown to approximately 90% confluency in twenty-four well plates and the conjugate or photosensitizer was added in about 1 ml medium containing approximately 10% serum to each well. The concentration range for the conjugates and free $c_{e6}$ was between approximately 0.5 and 4 μM $C_{e6}$ equivalent and the incubation time was approximately 3 hours. After incubation at 37° C., the medium was removed and cells were washed about three times with approximately 1 ml sterile PBS and incubated with approximately 1 ml trypsin-EDTA for about 20 minutes (OVCAR-5) or 60 minutes (J774). The cell suspension was then removed and centrifuged (about 5 minutes at approximately 250×g). The trypsin supernatant was aspirated and retained and the pellets (frequently visibly fluorescent under long wave UV) were dissolved in about 1.5 ml of approximately 0.1M NaOH/1% SDS for at least about 24 hours to give a homogenous solution. The trypsin supernatant was checked for the presence of fluorescence to quantify any surface binding which might easily be removed by trypsin. The fluorescence was measured using an excitation wavelength of 400 nm and the emission scanned from 580 to 700 nm in order to calculate the peak area ($\lambda_{max}$=664 nm). A series of dilutions in approximately 1.5 ml 0.1M NaOH/1% SDS of known concentrations of each separate conjugate and photosensitizer was scanned for fluorescence as above in order to prepare calibration curves to allow for quantitation of the $c_{e6}$ by conversion of the measured peak areas into mol $c_{e6}$ equivalent. The protein content of the entire cell extract was then determined by a modified Lowry method (Marwell et al (1978) Anal Biochem 87:296) using BSA dissolved in approximately 0.1M NaOH/1% SDS to construct calibration curves. Results were expressed as mol of $c_{e6}$ per mg cell protein. For measuring the cellular uptake at 4° C., pre-cooled growth media was used and the plates with cells were cooled to about 4° C. in an ice-bath for approximately 20 minutes before the addition of photosensitizer solutions as well as after the addition. The incubation was carried out in the normal atmosphere in the dark (e.g., plates wrapped in aluminum foil).

Cells were seeded in 24 well plates, at densities of approximately 100,000 cells in about 1 ml medium. After about 24 hours, the cells were given about 1 ml fresh medium containing 10% serum and a specific conjugate or free $c_{e6}$ ($c_{e6}$ equivalent concentration of approximately 4 nmoles per well) and incubated for about 3 hours at 37° C. Immediately prior to illumination, the cells were washed about 3 times with PBS with $Mg^{2+}/Ca^{2+}$ and the wells were replenished with approximately 1 ml medium containing HEPES and about 10% FCS. Light (660 nm) was delivered from beneath the wells from a diode laser at a fluence rate of about 50 mW/cm$^2$ via a fiber optic coupled microscope objective. Wells were illuminated in blocks of four defined by a black mask placed beneath the 24 well plate. Fluences were about 2, 5, and 10 J/cm2. After completion of illumination, the dishes were returned to the incubator for a further approximately 24 hour incubation. Cell survival was determined by the 3-(4,5-dimethylthiazol-2-yl)-2,5-diphenyltetrazolium bromide (MTT) assay, which measures mitochondrial dehydrogenase activity. It has been extensively used for measuring viability of cell cultures after PDT and has been shown to have close correlation with colony forming assays (McHale et al (1988) Cancer Letters 41:315). Approximately twenty-four hours post illumination, the cells were given fresh media and about 100 μl MTT (5 mg/ml) solution was added to each well and cells were incubated at 37° C. After approximately 1 hour incubation, the supernatant medium was gently aspirated and about 1 ml of DMSO was added to lyse the cells and dissolve the deep blue formazan. Plates were gently shaken on an orbital shaker in the dark for approximately 15 min to complete the dissolution of any formazan crystals and the blue DMSO solution was transferred to 96 well plates (about 200 μl per well, 5 wells per well of 24-well plate). Absorbance was read on an automated plate reader (Model 2550 EIA, Bio-Rad Laboratories, Hercules, Calif.) at 570 nm. Data points were the average of 3 wells of the 24 well plate (15 wells of 96 well plate).

The role of scavenger receptors in the uptake of these conjugates was tested by measuring the reduction in the cellular content of photosensitizer produced by competing the uptake with a ligand known to be recognized by the scavenger receptor. The reduction in cellular uptake was then related to protection of the cells from phototoxicity. Increasing amounts of unlabeled mal-BSA were added simultaneously with the conjugates to J774 and OVCAR-5 cells and incubated for about 3 hours. Approximately 0, 50, 100, and 200 μg/ml mal-BSA were used, representing a range of about 0.25 to 3 fold molar excess of the BSA contained in approximately 4 μM $BSAc_{e6}$ or mal-BSA-$c_{e6}$. The cellular uptakes and phototoxicities were measured as described above.

Figure 10:
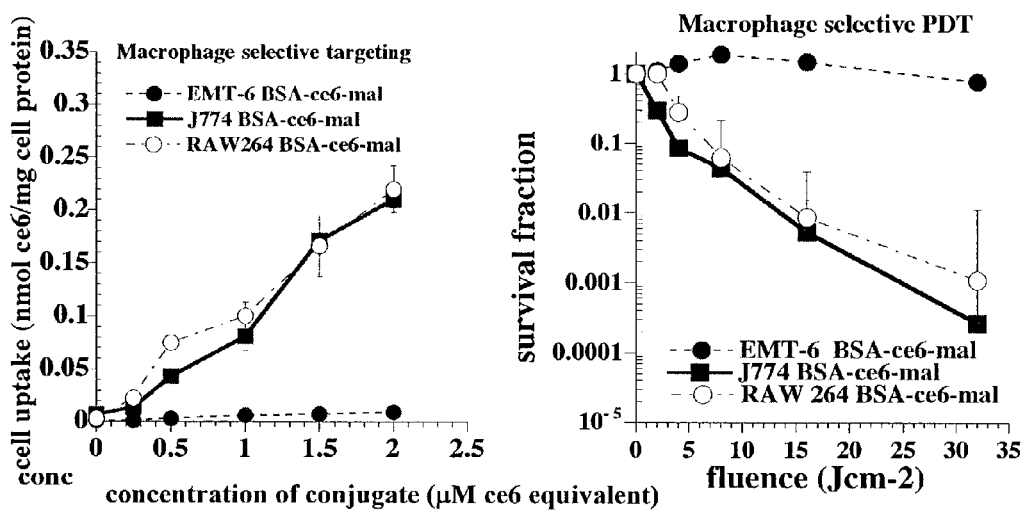
FIG. 10 shows the selective targeting and phototoxicity of maleylated BSA-$c_{e6}$ conjugates.

Mouse-macrophage cells (J774 or RAW264.7) took up more than ten times as much dye as non-target EMT-6 cells and, upon illumination with modest levels of red light, were killed approximately 1000 times as much. The maleylated conjugates had greater macrophage selectivity and, therefore, higher phototoxicity than their non-maleylated counterparts (FIG. 10).

After 1 week on the peanut oil diet, the abdominal aorta was denuded of endothelium by a modified Baumgartener technique. Briefly, each animal was anesthetized with a mixture of ketamine and xylazine and the right femoral artery was isolated. Subsequently, a 4F Fogarty embolectomy catheter was introduced via arteriotomy and advanced under fluoroscopic guidance to the level of the diaphragm. The balloon was then inflated to 3 psi above balloon inflation pressure and three passes were made down the abdominal aorta with the inflated catheter. The femoral artery was subsequently ligated and the wound closed.

Figure 11:
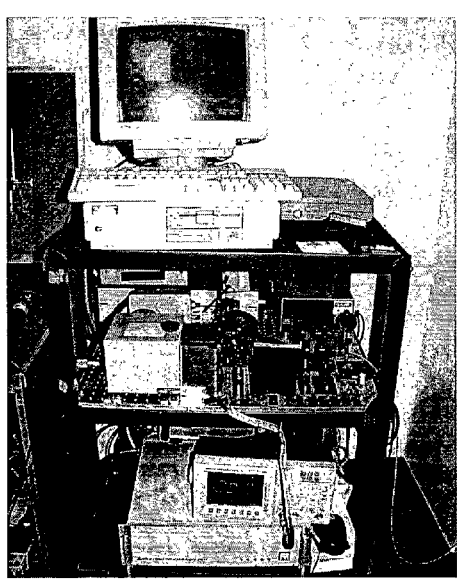
FIG. 11 shows an optical multichannel analyzer used for fluorescence localization within ex vivo aortas.
Figure 11:
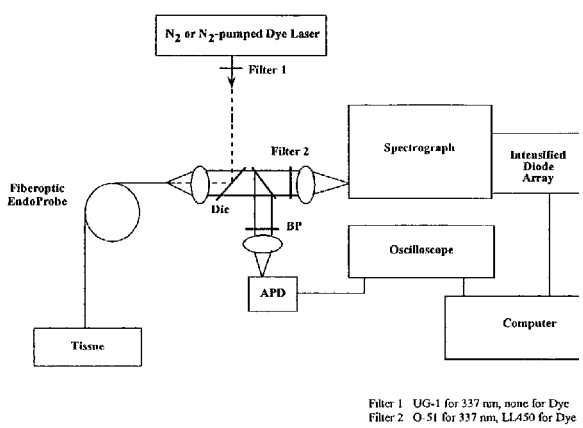

For fluorescence localization within ex vivo aortas, aortic segments were cut open and flattened and the luminal side examined by spectrofluorometry using either a fiber-bundle based double monochromator spectrofluorimeter (Skin Scan, Spex Figure), where emission spectra (excitation 400 nm, emission 580-720 nm) was collected about every 3 mm across the entire area of the exposed intimal surface, or an optical multichannel analyzer (FIG. 11).

For confocal fluorescence microscopy, selected parts of the aortas were snap frozen in liquid nitrogen and approximately 10-20 μm frozen sections were prepared. These sections underwent laser scanning confocal fluorescence microscopy to detect the tissue distribution of the $c_{e6}$. The red intracellular fluorescence from $c_{e6}$ together with green tissue auto-fluorescence was imaged in the cells in 10 μm frozen sections. Sections were examined with a laser scanning confocal fluorescence microscope. A Leica DMR confocal laser fluorescence microscope (Leica Mikroskopie und Systeme GmbH, Wetzler, Germany)(excitation 488 nm argon laser) and 4×–40× air immersion lens or a 100× oil immersion objective was used to image at a resolution of 1024×1024 pixels. Two channels collected fluorescence signals in either the green range (580 nm dichroic mirror plus 530 nm (+/−10 nm) bandpass filter) or the red range (580 nm dichroic mirror plus 590 nm longpass filter) and were displayed as false color images. These channels were overlaid using TCS NT software (Version 1.6.551, Leica Lasertechnik, Heidelberg, Germany) to allow visualization of overlap of red and green fluorescence. These sections were also stained by immunohistochemistry using macrophage specific monoclonal antibodies and conventional H&E staining. Other parts of normal and atherosclerotic aorta were cut into small pieces, weighed and dissolved in sodium hydroxide/SDS and the tissue content of $c_{e6}$ was determined by spectrofluorimetry as previously described (Hamblin et al (2000) Br. J. Cancer 83:1544).

Figure 12:
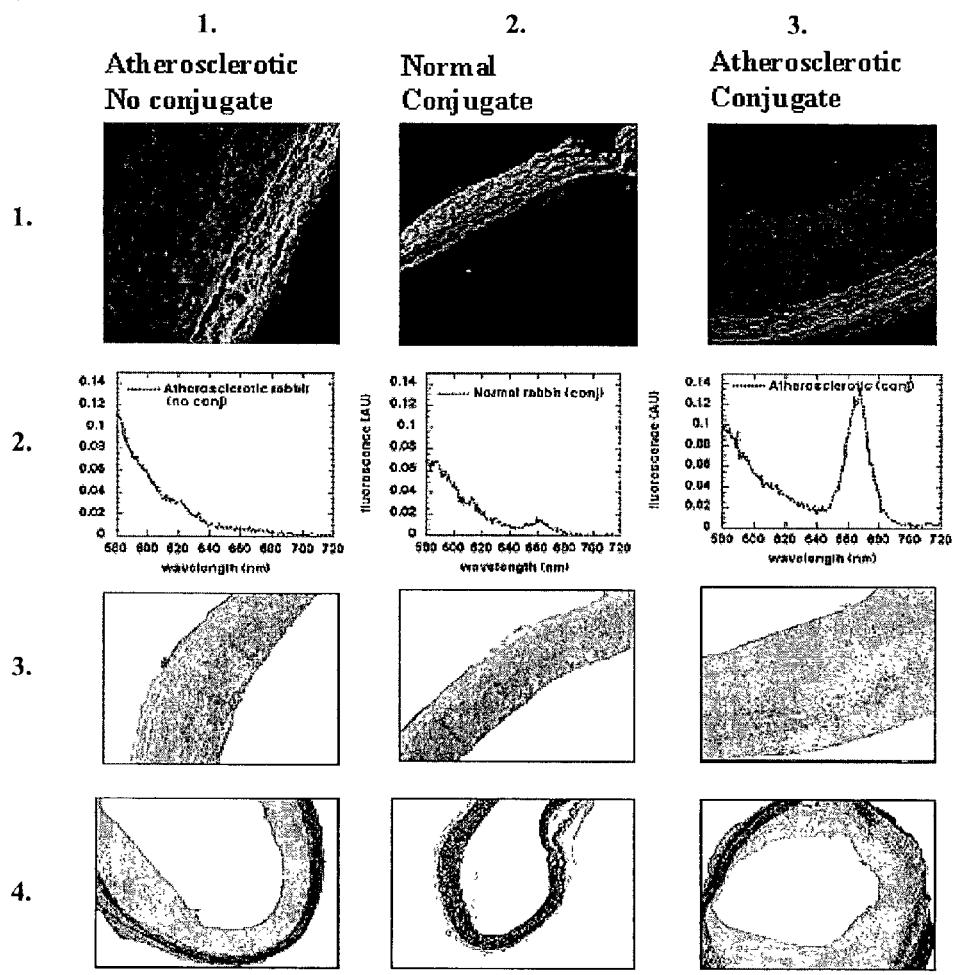
FIG. 12 shows an analysis of aortic sections from rabbits injected with or without conjugates about 24 hours after injection of the conjugate (Row 1: confocal fluorescence, Red=chlorin e6, Green=elastic lamina auto-fluorescence; Row 2: fluorescence emission spectra of intimal surface of aortic segments ex vivo; Row 3: Hematoxylin and eosin staining of formalin fixed paraffin embedded aortic segments; Row 4: Verhoeff's elastic tissue stain). Column 1 shows an atherosclerotic rabbit with no injection of conjugate. Column 2 shows a normal non-atherosclerotic rabbit injected with conjugate. Column 3 shows an atherosclerotic rabbit injected with conjugate.

FIG. 12 shows an analysis of aortic sections from rabbits injected with or without conjugate (approximately 2 mg/kg in PBS) about 24 hours after injection of the conjugate. Row 1 shows confocal fluorescence micrographs of frozen aortic sections (Red=chlorin$_{e6}$, Green=elastic lamina auto-fluorescence). Row 2 shows fluorescence emission spectra (excitation=400 nm) of initmal surface of aortic segments ex vivo. Row 3 shows Hematoxylin and eosin staining of formalin fixed paraffin embedded aortic segments. Row 4 shows Verhoeff's elastic tissue stain. The confocal micrographs showed red fluorescence from the PS ($c_{e6}$) and green auto-fluorescence principally from the elastic lamina of the arteries. Column 1 shows an atherosclerotic rabbit with no injection of conjugate. There was no red $c_{e6}$ fluorescence in the tissue section, nor any fluorescence signal from the intimal surface. Column 2 shows a normal non-atherosclerotic rabbit injected with conjugate. There is a small amount of red fluorescence visible in the adventitia rather than the intima in the fluorescence micrographs, and a small fluorescence emission signal from the intimal surface. Column 3 shows an atherosclerotic rabbit injected with conjugate. There was a large amount of red fluorescence visible in the plaque and this gave a corresponding large fluorescence emission signal from the intimal surface.

The intimal fluorescence signal was measured from different sections of aortas from atherosclerotic and normal rabbits. The areas of the abdominal aorta that received balloon injury developed greater amounts of plaque than the neighboring thoracic and lower abdominal aortas. The results from the intimal fluorescence measurements were confirmed by extracting sections of the aortas and measuring fluorescence with a spectrofluorimeter that gives a measure of the number of $c_{e6}$ molecules in the tissue sections.

Figure 13:
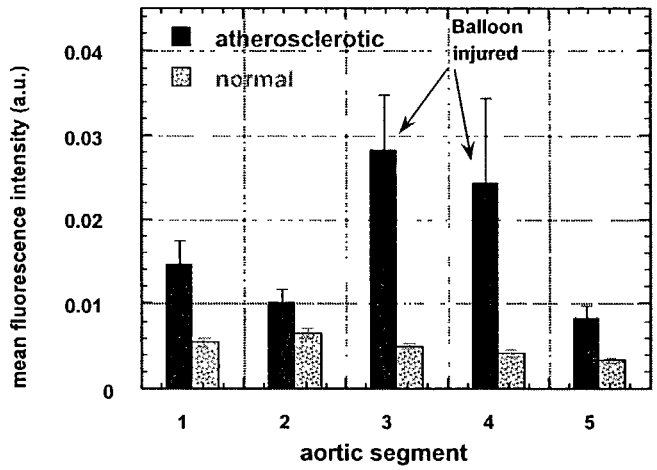
FIG. 13 shows a significant fluorescent signal from the intimal surface (determined by Skin Scan) in all sections from atherosclerotic rabbits compared to the corresponding sections of aorta from normal rabbits injected with conjugate. (Top: 1=thoracic aorta, 2=upper abdominal aorta below diaphragm, 3=mid abdominal aorta, 4=lower abdominal aorta, 5=pelvic aorta just above bifurcation; Middle: Measurement of intimal surface fluorescence made by OMA-LIF system; Bottom: Data from extraction of gross tissue samples).
Figure 13:
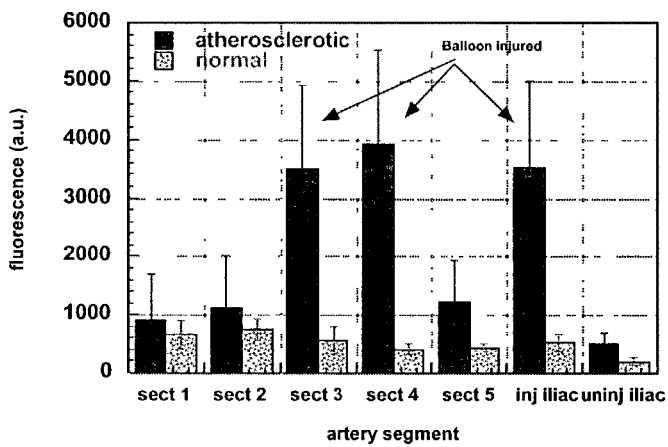
Figure 13:
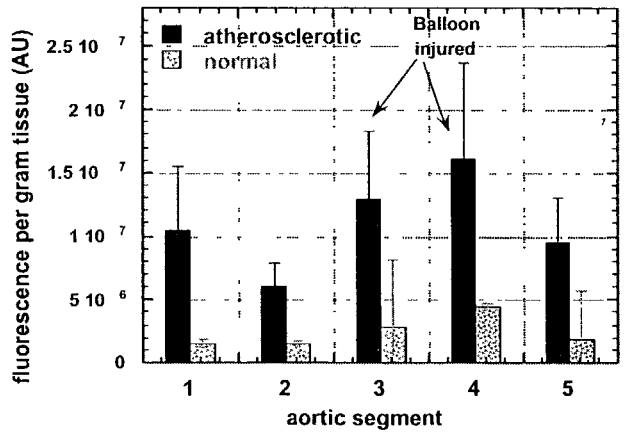

FIG. 13 shows a significant fluorescent signal from the intimal surface (determined by Skin Scan) in all sections from atherosclerotic rabbits compared to the corresponding sections of aorta from normal rabbits injected with conjugate, but particularly higher in the sections from the balloon-injured areas. The section 1 depicts thoracic aorta, section 2 depicts upper abdominal aorta below the diaphragm, section 3 depicts mid-abdominal aorta, section 4 depicts lower abdominal aorta and section 5 depicts pelvic aorta just above bifurcation. At least 6 separate measurements were taken from each artery segment. By the nature of the balloon injury, sections 3 and 4 generally sustained a more severe endothelial injury than other sections and hence developed more severe atherosclerosis. These plaques are extremely rich in marcophages and therefore, are most analogous to vulnerable plaques in humans. Such lesions represent the animal model system used by those of skill in the art to study the features of vulnerable plaques. The signal from atherosclerotic rabbit section 3 was greater than normal control section 3 ($p<0.0005$) and the signal from atherosclerotic section 4 was greater than normal control section 4 ($p<0.005$).

The second measurement of intimal surface fluorescence was made by the OMA-LIF system described above. At least 15 separate fluorescence measurements were taken from each artery segment. In addition, the iliac artery through which the balloon was passed also sustained an injury due to its relatively small diameter compared to aortic section 5 and, therefore, developed atherosclerosis compared to the uninjured iliac artery. FIG. 13 shows a similar pattern to the Skin Scan measurements that can be seen with highly significant increases in fluorescence in the arteries with inflamed plaque (i.e., balloon injured aorta and iliac). Sections 3, 4 and injured iliac of atherosclerotic compared to normal control had p values<0.0001, while section 5 and uninjured iliacs had p values<0.0005. Accordingly, the less severe plaques of section 5 are distinguishable from the macrophage-rich plaques of sections 3 and 4. Sections 1 and 2 were not significantly different in atherosclerotic and normal rabbits.

To corroborate the selectivity of the macrophage targeted conjugate for inflamed plaque, the dye molecules were extracted out of the pre-weighed tissue sections by dissolving the tissue in a solvent (1M NaOH/0.2% SDS) designed to preserve $c_{e6}$ fluorescence. These dissolved tissue sections were then measured on the spectrofluorimeter and the fluorescent signal was divided by the tissue weight to give a value per gram tissue. At least four pieces of tissue were dissolved for each data point. The differences between atherosclerotic and normal rabbits were significant ($p<0.05$) for sections 1, 2, and 4. The lower level of significance in this assay was probably due to the inability to sample as many points as was possible with the surface fluorescence measurement. In addition, it is possible that surface measurement of fluorescence was more sensitive than bulk extraction for detecting macrophage population because macrophages are more likely to be concentrated in the inflamed surface of the plaque.

Figure 14:
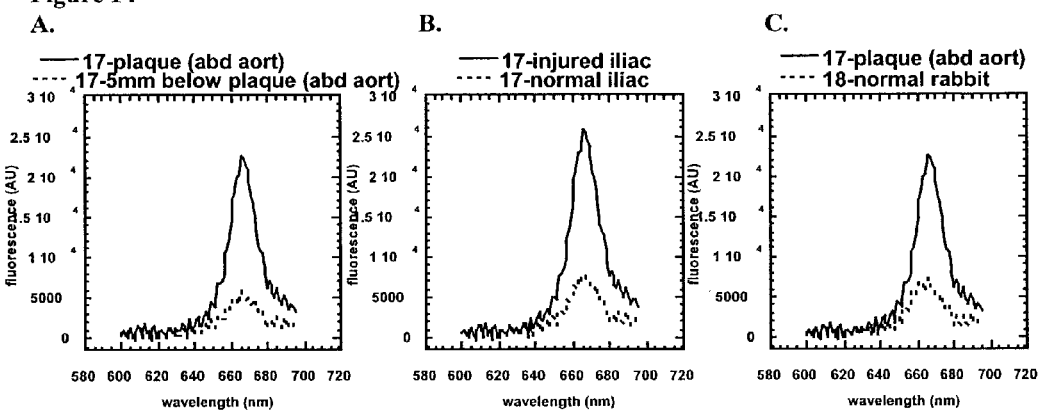
FIG. 14 shows the contrast between a large aortic plaque and an area of the abdominal aorta 5 mm beneath the plaque (14A), between the balloon injured iliac artery and the contralateral normal artery in the same rabbit (14B), and between the plaque-laden aorta of an atherosclerotic rabbit and the same area of the aorta in a normal rabbit (14C).

In FIG. 14a, a marked contrast was seen between a large aortic plaque and an area of the abdominal aorta 5 mm beneath the plaque. In FIG. 14b, another marked contrast was seen between the balloon injured iliac artery and the contralateral normal artery in the same rabbit. Similarly, FIG. 14c shows a contrast between the plaque-laden aorta of an atherosclerotic rabbit and the same area of the aorta in a normal rabbit. These spectra were obtained in a rabbit that had received an overdose of anesthesia. The rabbit received a laparotomy that exposed the abdominal aorta and iliac arteries. The rabbit also had an arterotomy in the right leg to expose the femoral artery. The fiber-optic catheter of the OMA-LIF apparatus was advanced through the femoral and iliac arteries, to the abdominal aorta, up to the thoracic aorta. Spectra were obtained and the fiber optic catheter pulled back about 5 mm each time successive spectra were obtained. By palpation of the outside of the artery, the position of the catheter in relation to plaques was determined Thus, a novel method has been developed for targeting a photosensitizer composition to the activated macrophages of a vulnerable plaque with high specificity.

Example 3

In vivo Photodynamic Therapy

An intravascular fluorescence catheter that efficiently localized a fluorescence signal from a vulnerable plaque in the rabbit coronary (although not limited to rabbit) through flowing blood was developed. In addition, a therapeutic intravascular light delivery system was developed that illuminated the vulnerable plaques through flowing blood with the appropriate wavelength, fluence and fluence rate of light, achieving the desired therapeutic effect.

Results

Figure 15:
FIG. 15 shows a laparotomy and surgical exposure of the aorta and surrounding tissues (15A) and a histological examination of the arteries (15B: Top-histopathology of PDT treated atherosclerotic aorta; Bottom-histopathology of atherosclerotic aorta that received light but no conjugate).
Figure 15:
Figure 15:
Figure 15:
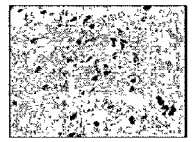
Figure 15:
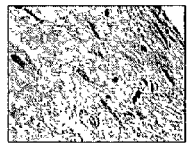
Figure 15:
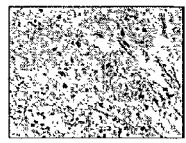
Figure 15:
Figure 15:
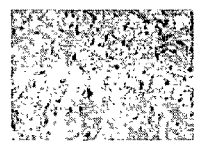

PDT in rabbit aorta was demonstrated to be possible in vivo in living rabbits through flowing blood without undue harm to the rabbits and with no short-term toxicity. The same parameters were used as above (photosensitizer composition, dose and time interval) in order to be able to correlate treatment effects with previously determined dye localization in plaque lesions. Animals (one atherosclerotic and one normal rabbit, each injected with Mal-BSA-$c_{e6}$ 24 hours previously; and one atherosclerotic rabbit that received no injection) were anesthetized as before and a cylindrical diffusing tipped fiber optic (length of tip=2 cm, diameter=1 mm) was advanced to a position midway along the balloon-injured abdominal aorta. The fiber had a SMA connector at the proximal end that can be connected to a diode laser emitting light at approximately 665 nm for Mal-BSA-$c_{e6}$. Light was delivered at a fluence rate of approximately 100 mW/cm of diffusing tip and a total fluence of approximately 100 J/cm was delivered. At the conclusion of the illumination, the fiber was withdrawn and the arteriotomy and overlying wound were closed. Animals were sacrificed 48 hours later. They received a laparotomy and surgical exposure of the aorta and surrounding tissues (FIG. 15A). The top panel of FIG. 15A shows light delivery into the abdominal aorta via a diffusing tip catheter inserted into the femoral artery, demonstrating the feasibility of intra-arterial illumination. The middle panel of FIG. 15A shows atherosclerotic aorta that is thick such that light did not penetrate to extra-aortic tissue. The bottom panel of FIG. 15A shows normal aorta that is thin such that light penetrates to give a slight but definite damage to psoas muscle. Complete aortas and iliac arteries were removed from the PDT treated normal and atherosclerotic rabbits and control (no Mal-BSA-$c_{e6}$ injection) atherosclerotic rabbit and were examined by histology using H&E, Masson Trichrome and Verhoeffs stain.

The two rabbits that received both the photosensitizer composition and light showed no ill effects of the treatment during the two days they lived before sacrifice. At necropsy, the atherosclerotic rabbit had no gross damage visible in the illuminated aortic section or surrounding tissue. By contrast, the normal rabbit had some minor damage visible in the paraaortic muscle, consisting of hemorrhage and purpura. Without being bound by theory, it is hypothesized that this damage was caused because the thickness of the normal artery was much less than the atherosclerotic aorta, and consequently, much of the light penetrated the artery and illuminated the surrounding tissue. The atherosclerotic rabbit that received light, but no conjugate was associated with any change to artery or surrounding tissue.

Histological examination of the arteries (FIG. 15B. Top panel: histopathology of PDT treated atherosclerotic aorta; Bottom panel: histopathology of atherosclerotic aorta that received light but no conjugate) showed changes in the illuminated section of the atherosclerotic rabbit that received both conjugate and light, consistent with PDT effects in the targeted tissue. There was evidence of apoptosis (pyknotic nuclei) and an inflammatory infiltrate in the plaque (FIG. 15B, left panel), together with some coagulative necrosis (FIG. 15B, middle panel), and extravasated erythrocytes that may have come from the vasa vasorum and visible damage in the plaque (FIG. 151B, right panel). Together, these histological data indicate that the treatment produced favorable modifications of plaque histology and reduced vulnerability. Histological changes were not observed in the normal rabbit that received photosensitizer composition and light, nor were any changes observed in the atherosclerotic rabbit that received light but no conjugate.

This technology satisfies the clear need for a new therapy that allows localized stabilization of vulnerable plaques in coronary arteries with the consequent reduced risk of rupture.

Example 4

In vivo Detection of Radionuclide Emitting Signals

Methods and devices of the present invention are readily employed by the skilled artisan.

Figure 18:
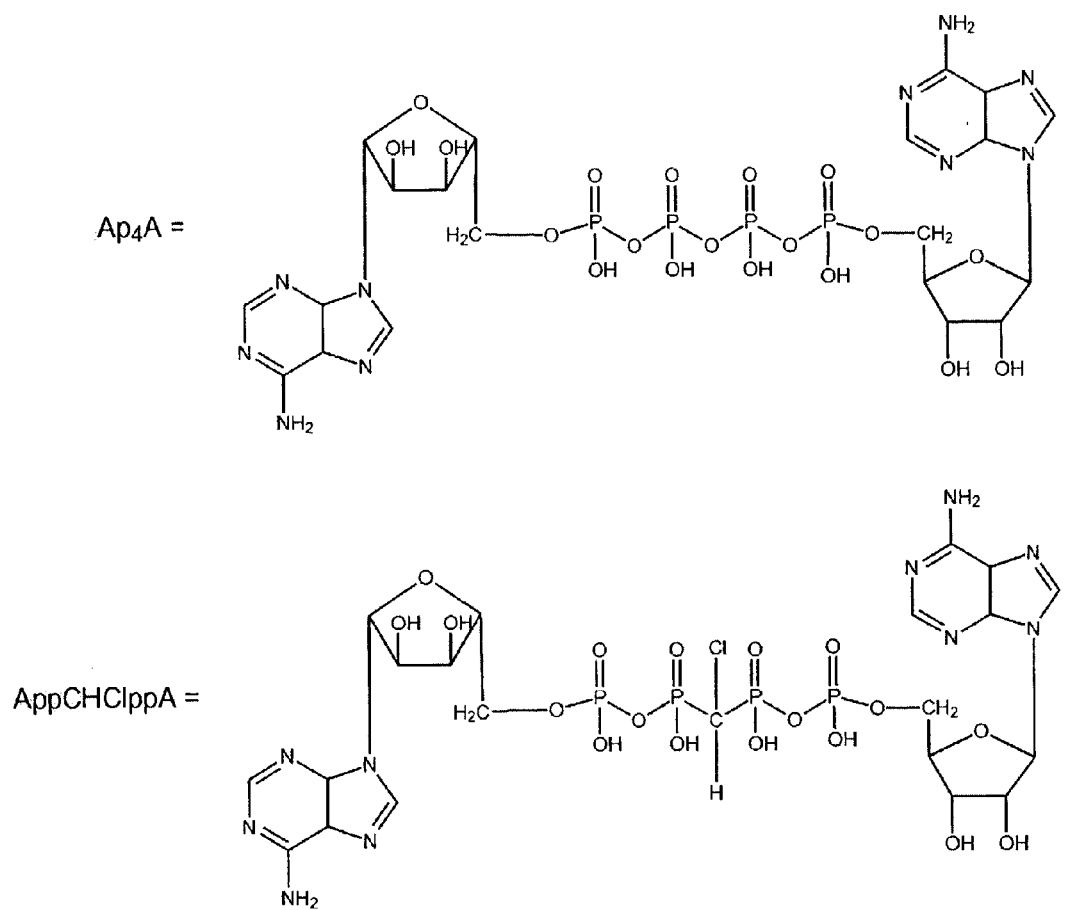
FIG. 18 depicts the chemical structure of Ap4A and AppCHCIppA.

Synthesis of $^{99m}$Tc-Labeled Ap4A Derivatives $^{99m}$Tc-labeled Ap4A derivatives (FIG. 18) were synthesized and HPLC-characterized using $TcO_4^-$ reduction with stannous chloride and mannitol as the coligand. The process was optimized for greater yield and consistency. The conveniently synthesized $^{99m}$Tc precursor $[^{99m}Tc(CO)_3(H_2O_3)]^{30}$ was also employed. By utilizing the precursor $[^{99m}Tc(CO)_3(H_2O_3)]^+$, additional Tc-Ap4A complexes were isolated from the pool of derivatives. The precursor was prepared from $^{99m}TcO_4$ in saline and CO at normal pressure. The novel one-pot synthesis of the organometellic precursor was designed for use in radiopharmacy (Schubiger et al. (1998) J Am Chem 120:7987-7988).

Generation of Experimental Atherosclerotic Lesions

Male New Zealand White rabbits weighing 2.5-3.0 kg (Charles River Breeding Laboratories) were maintained on a 2% cholesterol-6% peanut oil diet (ICN) for 3 months. After 1 week of the hyperlipidemic diet, the abdominal aorta was denuded of endothelium by a modified Baumgartener technique (Narula, J. et al. (1995) Circulation 92:474-484). Briefly, each animal was anesthetized with a mixture of ketamine and xylazine (100 mg/ml, 10:1 vol/vol; 1.5-2.5 ml sc), and the right femoral artery was isolated. A 4F Fogarty embolectomy catheter (Catalog Number 12-040-4F; Edwards Laboratories, Santa Ana, Calif.) was introduced through an arteriotomy and advanced under fluoroscopic guidance to the level of the diaphragm. The catheter was inflated to a pressure of 3 psi above the balloon inflation pressure with radiographic contrast media (Conray, Mallinckrodt), and three passes were made down the abdominal aorta with the inflated catheter. The femoral artery was then ligated, and the wound closed. The animals were allowed to recover from anesthesia and then returned to their cages.

Gamma Camera Imaging of Atherosclerotic and Normal Rabbits

Two to four millicuries of the $^{99m}$Tc-Ap$_4$A-glucoheptonate, $^{99m}$Tc-AppCHClppA-glucoheptonate, or $^{99m}$Tc-glucoheptonate (control) was injected into marginal ear veins of groups of three rabbits with experimental atherosclerotic lesions. As a control, three unlesioned animals were injected with 2-4 mCi of $^{99m}$Tc-Ap$_4$A-glucoheptonate. After radiopharmaceutical administration, serial gamma images were collected every minute for the first 5 minutes, every 2 minutes for the next 25 minutes, and every 5 minutes for the next 2.5 hours. In all of the rabbits, images were acquired in the anterior and lateral decubitus projections, including the heart and aorta, by using a standard field-of-view gamma camera (Series 100, Ohio Nuclear, Solon, Ohio) equipped with a high-resolution parallel-hole collimator and interfaced with a dedicated computer system (Technicare 560, Solon, Ohio). The pulse height analyzer was adjusted to record the 140 KeV photopeak of $^{99m}$Tc, and all images were recorded in a 256× 256 matrix.

After acquiring the final images, the animals were sacrificed with an overdose of sodium pentobarbital. The aortas were removed, opened along the ventral surface, and mounted on styrofoam blocks. The aortas then were placed on the face of the gamma camera and ex vivo images were recorded for 10 minutes.

Blood Clearance of $^{99m}$Tc-Ap$_4$A

Figure 19:
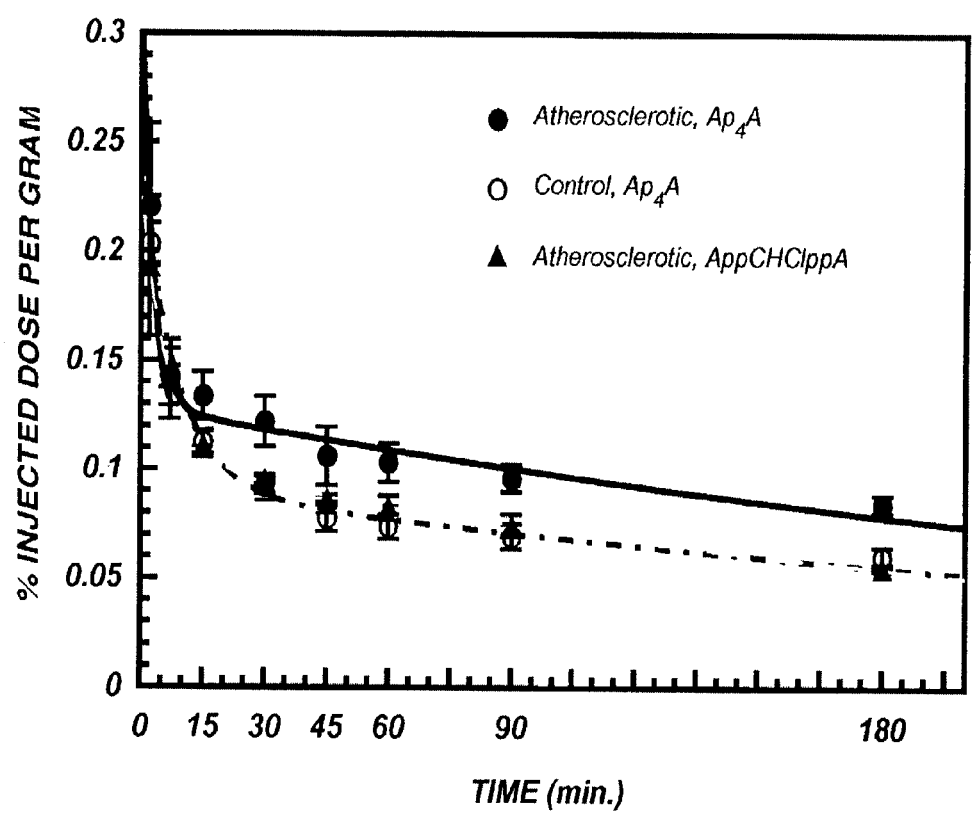
FIG. 19 depicts blood clearance of $^{99m}$Tc-labeled $Ap_4A$ and AppCHClppA in atherosclerotic and control rabbits. The biexponential fits to the data are also indicated: $^{99m}$Tc-$Ap_4A$ in atherosclerotic rabbits (solid line), $^{99m}$Tc-$Ap_4A$ in control rabbits (dot-dashed line), and $^{99m}$Tc-AppCHClppA in atherosclerotic rabbits (dashed line). Each point is the mean ±SEM for three animals.

Blood clearance of the $^{99m}$Tc-Ap$_4$A-glucoheptonate was rapid. In the control rabbits, the concentration of radioactivity (% ID/g) in the circulation averaged 0.25% at 2 minutes, after injection, decreased to 0.08% ID/g at 60 minutes and only slightly thereafter (i.e., up to 180 minutes). For all groups of rabbits, blood clearance was well described by bi-exponential functions with fast and slow components ($t_{1/2}$s) of ≈4 and ≈250 min, respectively (FIG. 19). Blood clearance was not significantly different between rabbits with artherosclerotic lesions and controls.

Results

Figure 20:
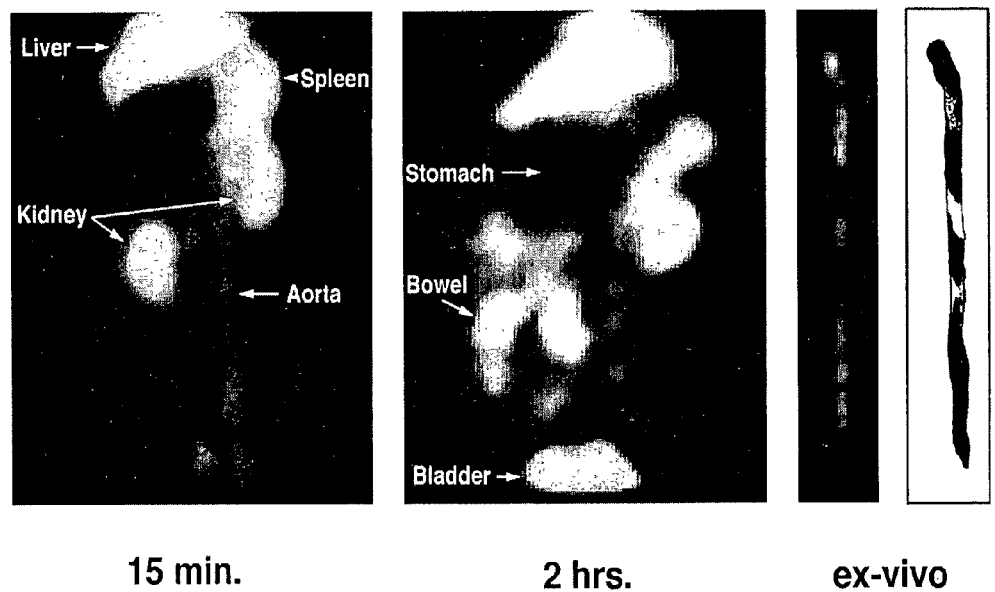
FIG. 20 depicts images of the aorta of a control rabbit. In vivo gamma camera image acquired at 15 minutes (Left) and 2 hours (Center) and after injection of $^{99m}$Tc-$Ap_4A$-glucoheptonate (Right). Corresponding ex vivo gamma camera image and sketch of the lesioned areas are also shown.
Figure 21:
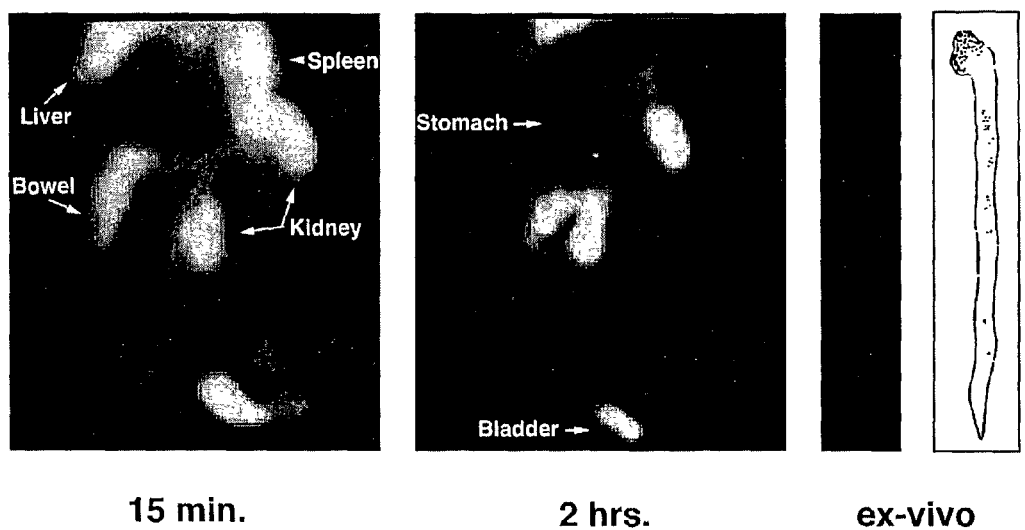
FIG. 21 depicts images of the aorta of a rabbit with experimental atherosclerosis. In vivo gamma camera images (i.e., lateral decubitus projection) acquired at 15 minutes (Left) and 2 hours (Center) after injection of $^{99m}$Tc-$Ap_4A$ (Right). Corresponding ex vivo gamma camera image and sketch of the lesioned areas are also shown.

All of the rabbits with experimental atherosclerosis showed rapid accumulation of radioactivity in the lesioned areas; representative images are shown in FIG. 20. The lesions were clearly visible within 20 minutes after injection, and radioactivity was retained in the lesions for the full 3 hours of the imaging session. When the aortas were imaged ex vivo, the pattern of radioactivity distribution closely paralleled the imaging results (FIG. 20). Inspection of the excised aortas revealed lesion patterns that were virtually identical to the results of in vivo and ex vivo imaging (FIG. 20). In contrast, both in vivo and ex vivo gamma camera imaging failed to demonstrate evidence of focal tracer accumulation in aortas of unlesioned rabbits; representative images are shown in FIG. 21. Inspection of the aortic specimens showed no evidence of vessel damage. Imaging atherosclerotic rabbits with $^{99m}$Tc-labeled glucoheptonate showed no evidence of specific accumulation in the aortic lesions, and the images were indistinguishable from those obtained in control rabbits imaged with $^{99m}$Tc-labeled Ap$_4$A or AppCHClppA (data not shown). With this tracer, radioactivity cleared rapidly from all organs ($t_{1/2}$s: 5-10 min) and accumulated in the kidneys and bladder.

Characterization of Vulnerable Plaque Using a $^{18}$F-FDG Beta Probe

Additionally, FDG was administered intravenously to two additional rabbits. FDG selectively accumulates in vulnerable plaques. Thereafter, a 1.6 mm thin, flexible beta probe, was inserted into the aorta. This probe is selectively sensitive to positron emissions, and was built by optically coupling a 1 mm diameter, 2 mm-long plastic scintillator to a PMT via a 40 cm long optical fiber. Measurements of FDG activity were made in triplicate, at 2 seconds per measurement, at grossly visible sites of plaque within areas of balloon injury; at non-injured sites in the cholesterol fed rabbits; and in corresponding areas in control aorta. Aortic segments at previously assessed sites of plaque and control areas were excised and examined for uptake of FDG by standard well counting.

Figure 22:
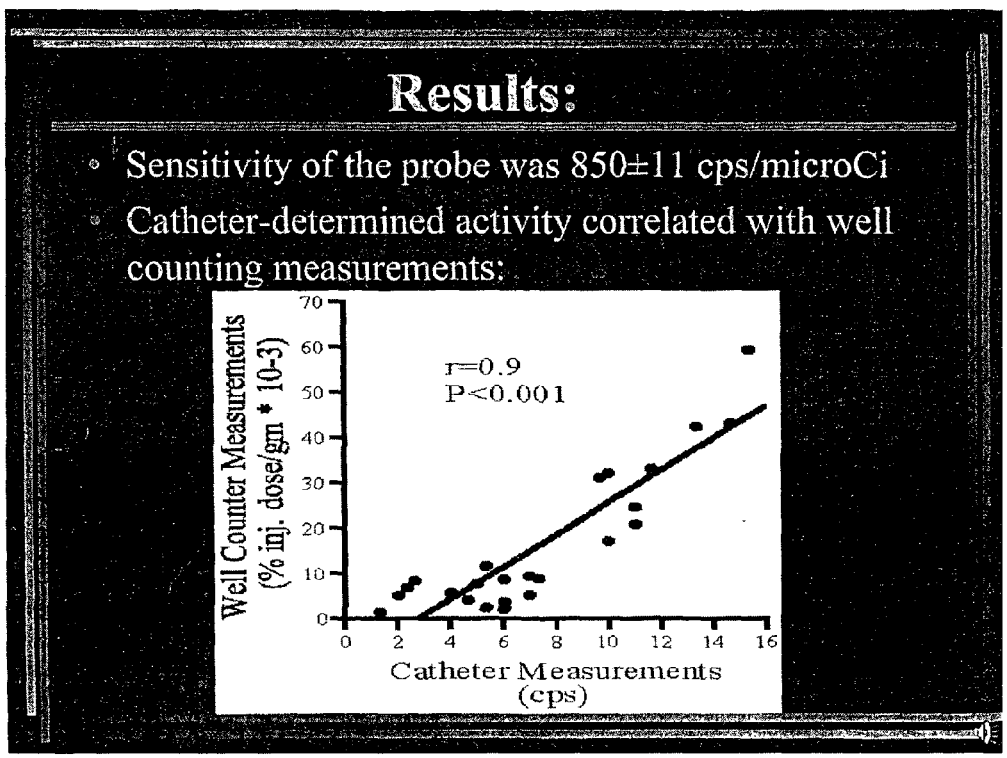
FIG. 22 depicts a graph showing the correlation between catheter-determined activity and counting measurements, (r–0.89, P<0.001).
Figure 23:
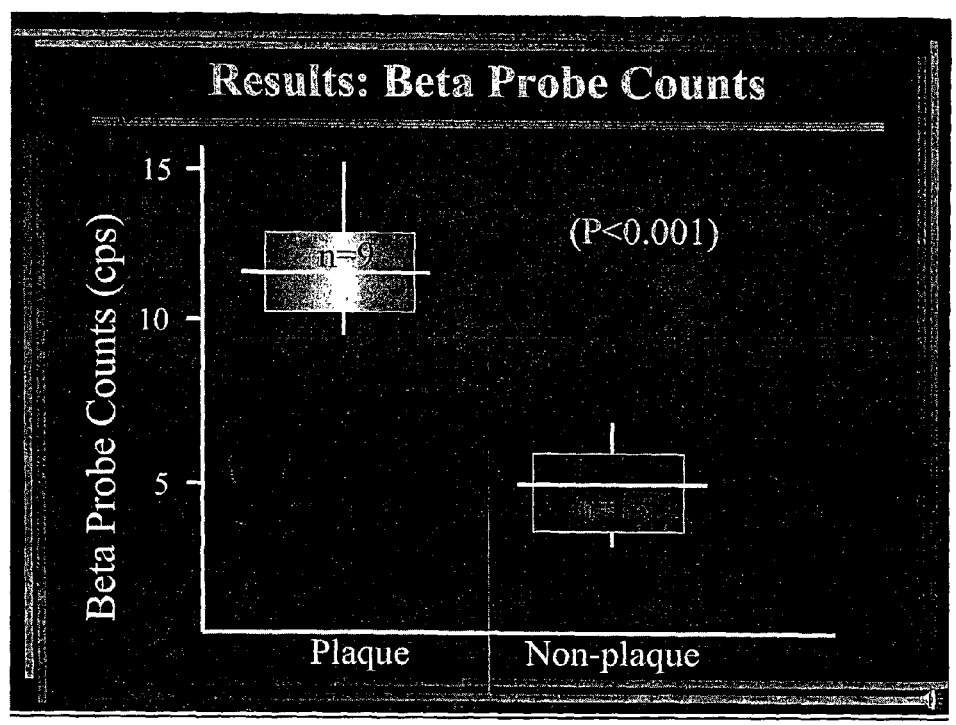
FIG. 23 depicts a bar graph showing the beta probe counts (cps) in plaque and nonplaque.

Sensitivity of the probe was 850±11 cps/microCi (mean±SD). Catheter-determined activity correlated well with well counting measurements, (r−0.89, P<0.001, FIG. 22). Moreover, atherosclerotic regions were readily distinguished from control by catheter mounted beta probe, (11.9±2.1 [n=9, range 9.7±15.3] vs. 4.8±1.9[n=14, range 1.3±7.3], cps in atherosclerotic vs. control regions, respectively, P<0.001).

The intravascular detection of positron emissions was achieved with sensitivity and specificity in an in vivo system.

We claim:

1. An apparatus for detecting and treating vulnerable plaque in a blood vessel, comprising:
   a probe operable to be inserted in the blood vessel, said probe including:
   a detector operable to detect beta rays from a composition, wherein the composition is administered and localized to the vulnerable plaque and includes a radiolabeled molecular carrier administered and localized to the vulnerable plaque; and
   a delivery unit operable to deliver a therapeutic compound to the vulnerable plaque, said therapeutic compound stabilizing the vulnerable plaque by reducing inflammatory components in the vulnerable plaque, wherein the delivery unit comprises an external unit and a stent that is retractable into and extendible out from the external unit, and wherein said external unit contains said therapeutic compound and is configured to apply said therapeutic compound onto said stent each time said stent is retracted into said external unit.

2. The apparatus of claim 1, wherein the delivery unit further includes an inflatable vessel, and the stent is moved towards a wall of the blood vessel by inflating said inflatable vessel.

3. The apparatus of claim 2, wherein said inflatable vessel contains a transparent, non-toxic fluid.

4. The apparatus of claim 1, wherein the detector is operable to detect gamma rays.

5. The apparatus of claim 4, wherein the detector includes a first predetermined sensitivity to beta rays and a second predetermined sensitivity to gamma rays.

6. The apparatus of claim 5, wherein the first predetermined sensitivity is equal to about 100 times the second predetermined sensitivity.

7. An apparatus for detecting and treating vulnerable plaque in a blood vessel, comprising:
   means for detecting beta rays from a composition, wherein the composition is administered and localized to the vulnerable plaque and includes a radiolabeled molecular carrier; and
   means for delivering a therapeutic compound to the vulnerable plaque, said therapeutic compound stabilizing the vulnerable plaque by reducing inflammatory components in the vulnerable plaque,
   wherein the means for delivering the therapeutic compound includes an external unit containing the therapeutic compound and a stent that is retractable into and extendible out from the external unit, and wherein said external unit is configured to apply said therapeutic compound onto said stent each time said stent is retracted into said external unit.

8. An apparatus for detecting and treating vulnerable plaque in a blood vessel, comprising:
   a probe operable to be inserted in the blood vessel, said probe including:
   a detector operable to detect beta rays from a composition, wherein the composition is administered and localized to the vulnerable plaque and includes a radiolabeled molecular carrier administered and localized to the vulnerable plaque; and
   a delivery unit operable to deliver a therapeutic compound to the vulnerable plaque, said therapeutic compound stabilizing the vulnerable plaque by inducing cross-linking of proteins of the plaque, wherein the delivery unit comprises an external unit and a stent that is retractable into and extendible out from the external unit, and wherein said external unit is configured to apply said therapeutic compound onto said stent each time said stent is retracted into said external unit.

9. The apparatus of claim 8, wherein the delivery unit further includes an inflatable vessel, and the stent is moved towards a wall of the blood vessel by inflating said inflatable vessel.

10. The apparatus of claim 9, wherein said inflatable vessel contains a transparent, non-toxic fluid.

11. The apparatus of claim 8, wherein the detector is operable to detect gamma rays.

12. The apparatus of claim 11, wherein the detector includes a first predetermined sensitivity to beta rays and a second predetermined sensitivity to gamma rays.

13. The apparatus of claim 12, wherein the first predetermined sensitivity is equal to about 100 times the second predetermined sensitivity.

14. An apparatus for detecting and treating vulnerable plaque in a blood vessel, comprising:
    means for detecting beta rays from a composition, wherein the composition is administered and localized to the vulnerable plaque and includes a radiolabeled molecular carrier; and
    means for delivering a therapeutic compound to the vulnerable plaque, said therapeutic compound stabilizing the vulnerable plaque by inducing cross-linking of proteins of the plaque,
    wherein the means for delivering the therapeutic compound includes an external unit and a stent that is retractable into and extendible out from the external unit, and wherein said external unit contains the therapeutic compound and is operable to apply said therapeutic compound onto said stent when said stent is retracted into said external unit.

15. A method for detecting and treating vulnerable plaque in a blood vessel, the method comprising:
    introducing a probe into the blood vessel, said probe including:
        a detector operable to detect beta rays from a composition, wherein the composition is administered and localized to the vulnerable plaque and includes a radiolabeled molecular carrier administered and localized to the vulnerable plaque; and
        a delivery unit operable to deliver a therapeutic compound to the vulnerable plaque, said therapeutic compound stabilizing the vulnerable plaque by reducing inflammatory components in the vulnerable plaque, wherein the delivery unit comprises an external unit and a stent that is retractable into and extendible out from the external unit, and wherein said external unit contains said therapeutic compound and is configured to apply said therapeutic compound onto said stent each time said stent is retracted into said external unit;
    administering the composition;
    detecting beta rays from the composition with the detector; and
    extending and retracting the stent from and into the external unit to apply the therapeutic compound to the vulnerable plaque.

16. The method of claim 15, wherein the delivery unit further includes an inflatable vessel, and the stent is moved towards a wall of the blood vessel by inflating said inflatable vessel, and wherein the method further comprises inflating said inflatable vessel.

17. The method of claim 16, wherein said inflatable vessel contains a transparent, non-toxic fluid.

18. The method of claim 15, wherein the detector is operable to detect gamma rays.

19. The method of claim 18, wherein the detector includes a first predetermined sensitivity to beta rays and a second predetermined sensitivity to gamma rays.

20. The apparatus of claim 19, wherein the first predetermined sensitivity is equal to about 100 times the second predetermined sensitivity.

21. A method for detecting and treating vulnerable plaque in a blood vessel, comprising:
    introducing a probe operable into the blood vessel, said probe including:
        a detector operable to detect beta rays from a composition, wherein the composition is administered and localized to the vulnerable plaque and includes
        a radiolabeled molecular carrier administered and localized to the vulnerable plaque; and
        a delivery unit operable to deliver a therapeutic compound to the vulnerable plaque, said therapeutic compound stabilizing the vulnerable plaque by inducing cross-linking of proteins of the plaque, wherein the delivery unit comprises an external unit and a stent that is retractable into and extendible out from the external unit, and wherein said external unit is configured to apply said therapeutic compound onto said stent each time said stent is retracted into said external unit;
    administering the composition;
    detecting beta rays from the composition with the detector; and
    extending and retracting the stent from and into the external unit to apply the therapeutic compound to the vulnerable plaque.

22. The method of claim 21, wherein the delivery unit further includes an inflatable vessel, and the stent is moved towards a wall of the blood vessel by inflating said inflatable vessel, and wherein the method further comprises inflating said inflatable vessel.

23. The method of claim 22, wherein said inflatable vessel contains a transparent, non-toxic fluid.

24. The method of claim 21, wherein the detector is operable to detect gamma rays.

25. The method of claim 24, wherein the detector includes a first predetermined sensitivity to beta rays and a second predetermined sensitivity to gamma rays.

26. The apparatus of claim 25, wherein the first predetermined sensitivity is equal to about 100 times the second predetermined sensitivity.

* * * * *